US009747099B2

(12) United States Patent
Shaw et al.

(10) Patent No.: US 9,747,099 B2
(45) Date of Patent: Aug. 29, 2017

(54) PARALLEL COMPUTER ARCHITECTURE FOR COMPUTATION OF PARTICLE INTERACTIONS

(71) Applicants: David E. Shaw, New York, NY (US); Martin M. Deneroff, Oakhurst, NJ (US); Ron O. Dror, New York, NY (US); Richard H. Larson, New York, NY (US); John K. Salmon, Chappaqua, NY (US)

(72) Inventors: David E. Shaw, New York, NY (US); Martin M. Deneroff, Oakhurst, NJ (US); Ron O. Dror, New York, NY (US); Richard H. Larson, New York, NY (US); John K. Salmon, Chappaqua, NY (US)

(73) Assignee: D.E. Shaw Research LLC, New York, NY (US)

( * ) Notice: Subject to any disclaimer, the term of this patent is extended or adjusted under 35 U.S.C. 154(b) by 867 days.

(21) Appl. No.: 13/680,962

(22) Filed: Nov. 19, 2012

(65) Prior Publication Data

US 2013/0091341 A1 Apr. 11, 2013

Related U.S. Application Data

(60) Division of application No. 13/329,852, filed on Dec. 19, 2011, which is a division of application No.
(Continued)

(51) Int. Cl.
*G06F 17/10* (2006.01)
*G06F 9/30* (2006.01)
(Continued)

(52) U.S. Cl.
CPC .............. *G06F 9/30* (2013.01); *G06F 15/76* (2013.01); *G06F 19/701* (2013.01); *G06F 19/16* (2013.01)

(58) Field of Classification Search
None
See application file for complete search history.

(56) References Cited

U.S. PATENT DOCUMENTS 5,432,718 A * 7/1995 Molvig et al. ............... 703/9
5,862,397 A   1/1999 Essafi et al.
(Continued)

FOREIGN PATENT DOCUMENTS

JP 03-204758 9/1991
JP 05-233566 9/1993
(Continued)

OTHER PUBLICATIONS

Snir A Note on N-body Computation with Cutoffs Theory Comput. Systems 37, 295-318, 2004.*
(Continued)

*Primary Examiner* — Omar Fernandez Rivas
*Assistant Examiner* — Cuong Luu
(74) *Attorney, Agent, or Firm* — Occhiuti & Rothlivek LLP

(57) ABSTRACT

A computation system for computing interactions in a multiple-body simulation includes an array of processing modules arranged into one or more serially interconnected processing groups of the processing modules. Each of the processing modules includes storage for data elements and includes circuitry for performing pairwise computations between data elements each associated with a spatial location. Each of the pairwise computations makes use of a data element from the storage of the processing module and a data element passing through the serially interconnected
(Continued)

processing modules. Each of the processing modules includes circuitry for selecting the pairs of data elements according to separations between spatial locations associated with the data elements.

9 Claims, 22 Drawing Sheets

Related U.S. Application Data

11/975,694, filed on Oct. 19, 2007, now Pat. No. 8,126,956, which is a continuation of application No. PCT/US2006/032498, filed on Aug. 18, 2006, which is a continuation-in-part of application No. PCT/US2006/014782, filed on Apr. 19, 2006.

(60) Provisional application No. 60/709,184, filed on Aug. 18, 2005, provisional application No. 60/756,448, filed on Jan. 4, 2006, provisional application No. 60/672,717, filed on Apr. 19, 2005, provisional application No. 60/709,184, filed on Aug. 18, 2005, provisional application No. 60/756,448, filed on Jan. 4, 2006.

(51) Int. Cl.
  *G06F 19/00* (2011.01)
  *G06F 15/76* (2006.01)
  *G06F 19/16* (2011.01)

(56) References Cited

U.S. PATENT DOCUMENTS

| | | | |
|---|---|---|---|
| 5,915,230 A | 6/1999 | Berne et al. | |
| 6,373,489 B1 | 4/2002 | Lu et al. | |
| 6,407,748 B1 | 6/2002 | Xavier | |
| 6,600,788 B1 | 7/2003 | Dick et al. | |
| 6,678,642 B1 | 1/2004 | Budge et al. | |
| 7,096,167 B2 | 8/2006 | Zhou et al. | |
| 7,734,456 B2* | 6/2010 | Fujita | 703/13 |
| 2003/0074402 A1 | 4/2003 | Stringer-Calvert et al. | |
| 2004/0225711 A1 | 11/2004 | Burnett et al. | |
| 2007/0276791 A1 | 11/2007 | Fejes et al. | |
| 2008/0052496 A1* | 2/2008 | Fujita | 712/220 |
| 2009/0254316 A1* | 10/2009 | Tillman et al. | 703/2 |

FOREIGN PATENT DOCUMENTS

| | | |
|---|---|---|
| JP | 07-140289 | 6/1995 |
| JP | 09-185592 | 7/1997 |

OTHER PUBLICATIONS

Cecchet, Emmanuel, "Memory Mapped Networks: A New Deal for Distributed Shared Memories? The SciFS Experience," *Proceedings of the IEEE International Conference on Cluster Computing*, Sep. 23-26, 2002, Piscataway, NJ USA, pp. 231-238 (XP010621880).

Culler et al., "Interconnection Network Design," *Parallel Computer Architecture—A Hardware/Software Approach*, Morgan Karufmann (1999) San Francisco, CA, pp. 749-778 (XP002333436).

Culler et al., "*Parallel Computer Architecture—A Hardware/Software Approach*," Morgan Karufmann (1999) San Francisco, CA, pp. 25-52; 78-79; 166-174; 513-521; 822-825 (XP002417055).

Mukherjee et al., "Efficient Support for Irregular Applications on Distributed-Memory Machines," *ACM Sigplan Notices* 30:68-79 (1995).

Oral, S. and George, A., "A User-Level Multicast Performance Comparison of Scalable Coherent Interfaces and Myrinet Interconnects," *Proceedings of the 28th Annual IEEE International Conference on Local Computer Networks*, Oct. 20-24, 2003, Piscataway, NJ, USA, pp. 518-527 (XP010666014).

Reinhardt et al., "Hardware Support for Flexible Distributed Shared Memory," *IEEE Transactions on Computers* 47(10): 1056-1072 (1998).

Shaw, David E., "A Fast, Scalable Method for the Parallel Evaluation of Distance-Limited Pairwise Particle Interactions," *J. Comput. Chem.*, 26: 1318-1328 (2005).

Snir, M., "A Note on N-Body Computations with Cutoffs," Theory of Computing Systems, Sprnger-Verlag USA, 37: 295-318 (2004).

Heffelfinger, G.S., "Parallel Atomistic Simulations," Computer Physics Communications, 128:219-237 (2000).

McCoy et al., "Parallel Particle Simulations of Thin-Film Deposition," International Journal of High Performance Computing Applications, 13:16-32 (1999).

Almasi et al., "Demonstrating the Scalability of a Molecular Dynamics Application on a Petaflops Computer," International Journal of Parallel Programming, 30:317-351 (2004).

Pande Visjay et al., "Atomistic Protein Folding Simulations on the Submillosecond Time Scale Using Worldwide Distributed Computing," Bioplymers 68:91-109 (2003).

Toukmaji et al., "Ewald Summation Techniques in Perspective: A Survey" Computer Physics Communications 95: 73-92 (1996).

Zaslaysky et al., "An Adaptive Multigrid Technique for Evaluating Long-Range Forces in Biomolecular Simulations," Applied Mathematics and Computation, 97:237-250 (1998).

Dehnen et al., "A Hierarchial 0(N) Force Calculation Algorithm," Journal of Computational Physics, 179: 27-42 (2002).

Darden et al., "New Tricks for Modelers from the Crystallography Toolkit: The Particle Mesh Ewald Algorithm and its use in Nucleic Acid Simulation," Structure with Folding and Design, vol. 7, No. 3, (ZP002358599) (1999).

Schlick et al., "Algorithmic Challenges in Computational Molecular Biophysics," Journal of Computational Physics, 151:9-48 (1999).

Sagui et al., "Molecular Dynamics Simulations of Biomolecules:Long-Range Electrostatic Effects," Annual Review of Biophysics and Biomolecular Structure, 28:155-179 (1999).

Greengard et al., "A New Version of the Fast Multipole Method for Screened Coulomb Interactions in Three Dimensions," Journal of Computational Physics, 180: 642-658 (2002).

Patent Cooperation Treaty, *PCT Notification of Transmittal of International Search Report*, PCT/US2006/032498, dated Mar. 30, 2007 (6 pages).

Patent Cooperation Treaty, *PCT Notification of Transmittal of International Search Report*, PCT/US2005/023184, dated Dec. 12, 2005 (2 pages).

Patent Cooperation Treaty, *Notification of Transmittal of International Preliminary Report on Patentability*, PCT/US2006/032498 dated Nov. 7, 2007 (14 pages).

Patent Cooperation Treaty, *PCT Notification of Transmittal of International Search Report*, PCT/US2006/014782, dated Jul. 26, 2006 (2 pages).

Deserno et al., "How to Mech Up Ewald Sum (I): A Theorhetical and Numerical Comparison of Various Particle Mesh Routines," Max-Planck-Intstitut fur Polymerforschung, pp. 1-18 (1998).

Rhee et al., "Ewald Methods in Molecular Dynamics for Systems of Finite Extent in One of Three Dimensions," The American Physical Society, 40(1):36-42 (1989).

Bowers et al., "Scalable Algorithms for Molecular Dynamics Simulations on Commodity Clusters," Proceedings of the 2006 ACM/IEEE SC 06 Conference (13 pages).

David E. Shaw, "A Fast, Scalable Method for the Parallel Evaluation of Distance-Limited Pairwise Particle Interactions," J. Comput. Chem. 26:1318-1328 (2005) XP-002417446.

Bowers et al., "Overview of Neutral Territory Methods for Parallel Evaluation of Pairwise Particle Interactions," Journal of Physics: Conference Series 16:300-3-05), 2005.

\* cited by examiner

| Decomposition | Asymptotic Scaling |
|---|---|
| Atom | $O(1)$ |
| Force | $O(p^{-1/2})$ |
| Spatial | $O(R^3)$ |
| Shaw's Neutral Territory (NT) | $O(R^{3/2}p^{-1/2})$ |
| Snir's Hybrid (SH) | $O(R^{3/2}p^{-1/2})$ |

R is the Interaction Radius
p is the Number of Processors

| | ALGORITHM |
|---|---|
| 2501 | begin send of particles to P, U and L |
| 2502 | begin receive of particles from P, U and L |
| 2503 | begin receive of forces from P, U and L |
| 2504 | do H-H interactions (special case) |
| 2505 | end receive of particles from P |
| 2506 | do H-P interactions |
| 2507 | end receive of particles from U |
| 2508 | do H-U interactions |
| 2509 | do P-U interactions |
| 2510 | begin send of forces to U |
| 2511 | end receive of particles from L |
| 2512 | do P-L interactions |
| 2513 | begin send of forces to P and L |
| 2514 | end receive of forces from P, U and L |

FIG. 25

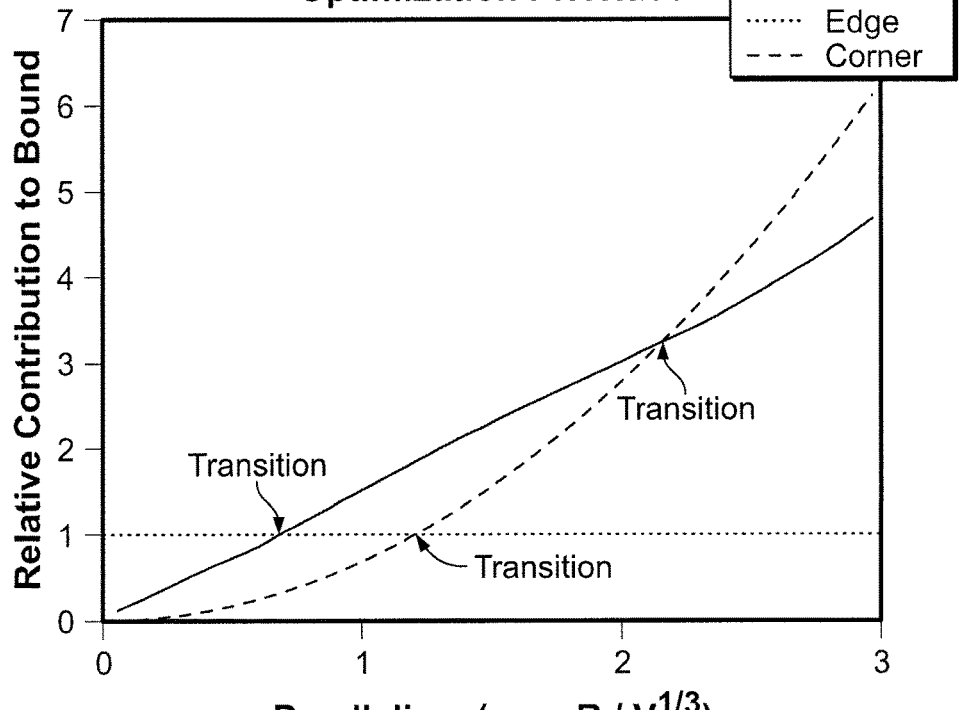

FIG. 26

| | H | FX | FY | FZ | EX | EY | EZ | C |
|---|---|---|---|---|---|---|---|---|
| H | 1* | 2 | 3 | 5 | 8 | 10 | 12 | 14 |
| FX | | 0 | 4 | 6 | 9 | 0 | 0 | 0 |
| FY | | | 0 | 7 | 0 | 11 | 0 | 0 |
| FZ | | | | 0 | 0 | 0 | 13 | 0 |
| EX | | | | | 0 | 0 | 0 | 0 |
| EY | | | | | | 0 | 0 | 0 |
| EZ | | | | | | | 0 | 0 |
| C | | | | | | | | 0 |

(column labels above table: 2710, 2720, 2721, 2722, 2730, 2731, 2732, 2740)

| | H | L | N | E | W | S | C |
|---|---|---|---|---|---|---|---|
| H | 1* | 2 | 3 | 5 | 0 | 0 | 11 |
| L | | 0 | 4 | 6 | 8 | 10 | 0 |
| N | | | 0 | 7 | 9 | 0 | 0 |
| E | | | | 0 | 0 | 0 | 0 |
| W | | | | | 0 | 0 | 0 |
| S | | | | | | 0 | 0 |
| C | | | | | | | 0 |

| | H | BA | CO | N | E | W | S |
|---|---|---|---|---|---|---|---|
| H | 1* | 2 | 3 | 5 | 7 | 0 | 0 |
| BA | | 0 | 4 | 0 | 8 | 10 | 0 |
| CO | | | 0 | 6 | 0 | 0 | 12 |
| N | | | | 0 | 9 | 11 | 0 |
| E | | | | | 0 | 0 | 0 |
| W | | | | | | 0 | 0 |
| S | | | | | | | 0 |

PARALLEL COMPUTER ARCHITECTURE FOR COMPUTATION OF PARTICLE INTERACTIONS

Under 35 USC 120, this application is a divisional of and claims the benefit of the priority date of U.S. application Ser. No. 13/329,852 filed on Dec. 19, 2011, which is a divisional of and claims the benefit of the priority date of U.S. application Ser. No. 11/975,694, filed on Oct. 19, 2007, which issued as U.S. Pat. No. 8,126,956 on Feb. 28, 2012, and which is a continuation of International Application Serial No. PCT/US2006/032498, filed on Aug. 18, 2006, which, under 35 USC 119, claims the benefit of the priority dates of U.S. Provisional Application Ser. No. 60/709,184, filed on Aug. 18, 2005, and U.S. Provisional Application Ser. No. 60/756,448, filed on Jan. 4, 2006, and which, under 35 USC 120, is a continuation-in-part of and claims the benefit of the priority date of International Application Serial No. PCT/US2006/014782, filed on Apr. 19, 2006, designating the United States, which under 35 USC 119 claims the benefit of the priority dates of U.S. Provisional Application Ser. No. 60/272,717, filed on Apr. 19, 2005, U.S. Provisional Application Ser. No. 60/709,184, filed on Aug. 18, 2005, and U.S. Provisional Application Ser. No. 60/756,448, filed on Jan. 4, 2006. The contents of all the foregoing applications are incorporated herein by reference.

This application is also related to U.S. Pat. No. 7,707,016, issued on Apr. 27, 2010, which is based on U.S. Provisional Applications Ser. No. 60/584,032, filed Jun. 30, 2004, U.S. Pat. No. 7,526,415, issued on Apr. 28, 2009, which is based on Ser. No. 60/584,000, filed Jun. 30, 2004, to U.S. Pat. No. 7,707,016, issued on Apr. 27, 2010, which is based on U.S. application Ser. No. 11/171,619, filed Jun. 30, 2005, to U.S. Pat. No. 7,526,415, issued on Apr. 28, 2009, which is based on U.S. application Ser. No. 11/171,634, filed Jun. 30, 2005, and to International Application Serial No. PCT/US2005/023184, filed Jun. 30, 2005, designating the United States, and published on Jan. 12, 2006, as WO 2006/00487, all of which are incorporated herein by reference.

This application is also related to
U.S. Provisional Application Ser. No. 60/584,032, filed Jun. 30, 2004,
Ser. No. 60/584,000, filed Jun. 30, 2004,
U.S. application Ser. No. 11/171,619, filed Jun. 30, 2005,
U.S. application Ser. No. 11/171,634, filed Jun. 30, 2005, and to
International Application Serial No. PCT/US2005/023184, filed Jun. 30, 2005, designating the United States, and published on Jan. 12, 2006, as WO 2006/004877 A2,
all of which are incorporated herein by reference.

BACKGROUND

This document relates to computation of particle interactions, including algorithms and hardware and software techniques that are applicable to such computation.

Simulation of multiple-body interactions (often called "N-body" problems) is useful in a number of problem areas including celestial dynamics and computational chemistry. Biomolecular or electrostatic particle interaction simulations complement experiments by providing a uniquely detailed picture of the interaction between particles in a system. An important issue in simulations is the simulation speed.

Determining the interaction between all pairs of bodies in the system by enumerating the pairs can be computationally intensive, and thus, alternate interaction schemes are often used. For example, all particles within a predefined radius of a particular particle are interacted with that particle while particles farther away are ignored. Special-purpose hardware has also been applied in order to reduce the overall computation time required for simulation.

SUMMARY

In one aspect, in general, a method for performing computations associated with bodies located in a computation region involves performing the computations in each subset of multiple subsets of the computations. Performing the computations in a subset includes accepting data of bodies located in each of a multiple import regions that are associated with the subset of the computations. The import regions are parts of the computation region. For each combination of a predetermined set of combinations of multiple of the import regions, computations that are associated with sets of bodies are performed. For each of these sets of bodies, at least one body of the set is located in the each import region of the combination.

Aspects can include one or more of the following features.

At least some of the combinations of multiple of the import regions each consists of a pair of the import regions.

Each of the subsets of computations is performed on a different node of a multiple node computing system.

Accepting the data for bodies from the import regions includes accepting data from a communication medium coupling at least two of the nodes of the computing system.

Each of the subsets of computations is performed in sequence on a computing system.

The subsets of computations are selected according to memory limitations of the computing system.

The method includes associating each of the subsets of computations with an iteration in an iterative sequence of computation phases.

Accepting the data for bodies from the import regions includes loading the data into a local memory associated with a processor on which the computations for the iteration are performed.

Each of the subsets of computations is associated with a separate sub-region of the computation region.

For each of the subsets of computations, the import regions are separate from the sub-region of the computation region with which the subset is associated.

The sub-regions associated with the multiple subsets of computations form a partition of the computation region. For example, the sub-regions form a regular partition of the computation region and/or a rectilinear partition of the computation region.

Performing the computations in each subset of computations further includes performing computations associated with sets of bodies. For each of these sets, each body of the set is located in the sub-region associated with the subset of computations. The method also includes performing computations associated with sets of bodies. For each of these sets, one body is located in the sub-region associated with the subset of computations and the other body or bodies of the set are located in the import regions associated with the subset of computations.

The performing of computations associated with sets of bodies in which each body of the set of bodies is located in the sub-region associated with the subset of computations is carried out while accepting the data for bodies from the import regions.

Performing the computations in each subset of computations further includes performing computations associated with sets of bodies. For each of these sets, each body of the set is located in one of the import regions associated with the subset of computations, and no body of the set is located in the sub-region associated with the subset of computations.

Performing the computations in each subset of computations includes applying a schedule of computations specified according to the import regions.

Each of the computations in the set of computations includes a computation of data characterizing an interaction of the set of bodies associated with that computation.

Each of the computations in the set of computations includes recording in a data structure an identification of the set of bodies associated with that computation.

The method further includes performing computations of data characterizing an interaction of each of the sets of bodies recorded in the data structure.

In performing the computations in all the subsets of computations, for any set of bodies, a computation for that set of bodies is performed in at most one of the subsets.

For at least some of the selected set of combinations of multiple import regions, a computation is performed for every combination of one body in each of the multiple import regions.

In performing the computations in all the subsets of computations, for any set of bodies, a computation for that set of bodies is performed in at most one of the subsets.

The steps are repeated for each of a series of time steps, the computations performed at each time step being used to update locations of the bodies in the computation region for use in a subsequent time step.

In another aspect, in general, a method is for performing a set of computations associated with bodies located in a computation region. Each of the computations in the set of computations is associated with a pair of the bodies. The method includes accepting data for bodies located in a neighborhood. The neighborhood includes a set of multiple zones. Computations associated with pair of bodies are performed such that the bodies of each pair are located in different of the zones. A spatial extent of at least one of the zones is determined to eliminate at least some points in one of the zones that are further away than a minimum distance from all points in another of the zones.

Aspects can include one or more of the following features.

The spatial extent is determined according to a threshold distance between pairs of bodies for which computations are to be performed.

A spatial boundary of one of the plurality of zones is determined according to a minimum distance to points within another of the set of zones.

At least one of the set of zones includes a non-planar boundary.

The computation region is partitioned into regular regions, and at least one of the set of zones includes some but not all of one of the regular regions.

The computation region is partitioned into regular regions and each region is associated with a subset of the computations.

The neighborhood corresponds to one of the regular regions.

In another aspect, in general, a method is for performing a set of computations associated with bodies located in a computation region. The computation region is partitioned into regular regions and each of the computations in the set of computations is associated with a set of the bodies. The method includes, for at least some of the regular regions, accepting data for bodies located in a neighborhood of the regular region, the neighborhood including a set of multiple zones. The set of zones includes at least one zone that is not contiguous with its parts being distributed in at least two dimensions of the computation region.

Each computation in the set of computations is associated with a pair of bodies.

The neighborhood consists of two zones, and for each of the pairs of bodies, one body of the pair is located in a different one of the two zones.

The set of zones includes at least one contiguous zone.

The contiguous zone is contiguous with the regular region.

At least two of the zones are elongated in one dimension of the computation region.

At least one of the zones extends over at least one other dimension of the computation region.

In another aspect, in general, a method is for performing computations associated with bodies located in a computation region. The method uses a processor coupled to a local memory. The method includes iteratively performing multiple subsets of the computations. In each iteration one subset of the multiple subsets of computations is performed. Performing the subset of computations includes loading into the local memory data of bodies located in each of a set of import regions associated with the subset of computations. The import regions are parts of the computation region. Computations associated with pairs of bodies are performed on the processor. For each pair, one body of the pair is located in a first of the import region and the other body of the pair is located in a second of the import region.

Aspects can include one or more of the following features.

The performing the computations associated with pairs of bodies is performed for each of a predetermined set of combinations of a first and a second of the import regions.

Performing the computations associate with the pairs of bodies includes performing computations associated with substantially all pairs of bodies in which one body of the pair is located in the first of the import regions and the other body of the pair is located in the second of the import regions.

In another aspect, in general, a method for performing computations associated with bodies located in a computation region includes, for each of a plurality of sub-regions of the computation region, maintaining data for bodies in that sub-region in a corresponding separate storage area. The sub-regions overlap such that at least some bodies have data maintained in multiple of the storage areas. For each of the sub-regions, accessing the data for bodies in that sub-region from the corresponding storage area and performing computations associated with sets of two or more of the bodies in that sub-region.

Each of the separate storage areas is associated with a node of a multiple node computing system.

Performing the computations associated with pairs of the bodies in the sub-region is performed on the node associated with the storage area corresponding to the sub-region.

Each of the separate storage areas is associated with a different node.

Each of the sub-regions includes a home region and a region extending at least a predetermined distance from the home region.

The home regions form a partition of the computation region.

The predetermined distance is at least half an interaction radius for pairwise interactions between bodies.

Performing the computations associated with the pairs of bodies in the sub-region includes performing computations for pairs of bodies for which a midpoint of locations of the bodies is within the home region for the sub-region.

In another aspect, in general, a method for computing interactions among sets of bodies located in a computation region includes, for each computation associated with one of the sets of bodies determining a computation unit of a set of computation units for performing the computation according to a mid location of the set of bodies determined from a location of each of the bodies.

Aspects can include one or more of the following features.

The mid location is determined according to a geometric midpoint of the locations of each of the bodies.

The mid location is determined according to a center of a minimal sphere bounding the locations of each of the bodies.

Each of the computation units is associated with a node of a multiple node computing system.

Each of the computation units is associated with a different node.

Each of the computation units is associated with one of the nodes.

The computation region is partitioned into regular regions each associated with a different one of the computation units.

Determining the computation unit for performing a computation associated with at least some of the sets of bodies is according to whether the mid location of the set is within the regular region associated with the computation unit.

Determining the computation unit for performing a computation associated with at least some of the sets of bodies includes selecting a computation unit from a set of computation units that include the computation unit for which the mid location of the set falls within the regular region associated with the computation unit.

The set of computation units further includes at least one other computation unit such that each of the bodies in the set belongs to at least one other set of bodies with a mid location falling in the regular region of the at least one other computation unit.

Selecting the computation unit is performed in part according to distribution of computation load across the computation units.

In another aspect, in general, a method is for performing a set of computations associated with bodies located in a computation region. Each of the computations in the set of computations is associated with a set of bodies. The method includes, for at least some of the subsets of computations, performing the computations in that subset of computations. This performing of the computations in that subset includes accepting data of bodies located in a vicinity of the sub-region associated with the subset of computations and performing computations for the sets of bodies. Each body of the set is located in the vicinity of the sub-region or in the sub-region. The locations of the bodies of the set and the sub-region satisfy a specified criterion. The specified criterion for the locations of the bodies in a set and the sub-region requires that a mid locations of the bodies in the set fall within the sub-region.

Aspects can include one or more of the following features.

The mid locations of the bodies in the set is determined according to the center of a bounding sphere enclosing the locations.

The mid locations of the bodies in the set is determined according to an average of the locations.

At least some of the sets of bodies consists of two bodies.
At least some of the sets of bodies consists of three bodies.
At least some of the sets of bodies include more than three bodies.

In another aspect, in general, a method is for performing a set of computations associated with bodies located in a computation region. Each of the computations in the set of computations is associated with a pair of bodies. The method includes, for at least some of the subsets of computations, performing the computations in that subset of computations. The performing of the computations in that subset includes accepting data of bodies located in a vicinity of a sub-region associated with the subset of computations and performing computations for pairs of bodies. Each body of the pair is located in the vicinity of the sub-region or in the sub-region. The locations of the bodies of the pair and the sub-region satisfy a specified criterion.

Aspects can include one or more of the following features.

The specified criterion incorporates information about a distribution of bodies of pairs in a vicinity of neighboring sub-regions.

The specified criterion for the locations of the bodies in a pair and the sub-region requires that a midpoint of the locations of the bodies in the pair fall within the sub-region.

In anther aspect, in general, a method for computation of molecular dynamics simulation of a plurality of processing nodes arranged in geometric grid includes exchanging particle data between processing nodes such that data for all pairs of particles separated by less than an interaction radius are available on at least one processing node. Two or more types of computations are performed for pairs of particles available at a processing node.

Aspects can include one or more of the following features.

The two or more types of computations include at least two of: electrostatic interaction, bonded force, particle migration, charge spreading, and force spreading computation.

The two or more types of computations includes electrostatic interaction computation.

In another aspect, in general, a method for performing computations involving sets of items includes associating each of a multiple items with a set of groups to which the item belongs. Multiple sets of the items are identified as candidates for performing a computation associated with each set. Sets are excluded from the computation according to the group membership of the items in the set.

Aspects may include one or more of the following.

Excluding the sets includes excluding a set if multiple of its items are associated with a common group.

Excluding the sets includes excluding a set if all of its items are associated with a common group.

The items are associated with bodies in a simulation system.

The bodies form linked sets of bodies and at least some of the groups are each associated with a linked set of bodies.

Each of the items associated with the bodies in the set of bodies is associated with the group associated with the linked set.

The linked sets of bodies include bonded sets of bodies.

Identifying the plurality of sets of the items as candidates includes identifying the sets such that the associated bodies fall within a prescribed interaction radius.

In another aspect, in general, a software product is adapted to perform all the steps of any of the above methods. The software product can include instructions for performing the steps embodied on a computer-readable medium.

In another aspect, in general, a parallel processing system is applied to computing particle interactions. The system includes multiple computation nodes arranged according to a geometric partitioning of a simulation volume. Each of the nodes includes a storage for particle data for particles in a region of the simulation volume. The system also includes a communication system including links interconnecting the computations nodes. Each of the nodes includes a processor subsystem, the processor subsystems of the computation nodes together, in a distributed manner, coordinate computation of the particle interactions.

Aspects can include one or more of the following.

The communication system forms a toroidal mesh.

The communication system includes separate components each linking a different neighborhood of computation nodes.

Each separate component of the communication system includes a point-to-point link between a two of the computation nodes.

Sending at least some of the particle data to the other of the computation nodes includes passing that data via other computation nodes over multiple of the separate components of the communication system.

Each of the computation nodes further includes a communication subsystem of the communication system.

The communication subsystem is configurable to pass particle data from one computation node to another computation node without intervention of the processor subsystem Each node is configured to perform one or more of:

(i) send particle data to other of the computation nodes requiring that data for computation, (ii) accept particle data sent from other of the computation nodes, (iii) perform computations using the accepted particle data producing first results, (iv) send the first results to other of the computation nodes, (v) accept the first results send from other of the computation nodes, and (vi) perform further computations using the accepted first results producing second results.

The system is configured to perform all steps (i) through (vi).

The system is configured to perform some or all of steps (i) through (vi) in sequence.

The system is configured to repeat steps (i) through (vi) in each iteration of a simulation.

The communication system is configured to accept the particle data from a computation node, and to distribute that particle data to a neighborhood of other of the computation nodes.

The communication system includes storage for configuring the neighborhood for distributing the particle data.

Each of the computation nodes further includes a communication subsystem of the communication system, the communication subsystem being configurable to pass particle data from one computation node to another computation node without intervention of the processor subsystem.

Each of the computation nodes further includes a computation subsystem for performing the computations using the accepted particle data producing the first results.

The computation subsystem is further for sending the first results to other of the computation nodes, without intervention of the processing subsystem at that node.

Each of the computation nodes further includes a memory subsystem for accepting the first results send from other of the computation nodes, without intervention of the processing subsystem.

The memory subsystem is further for accumulating the accepted first results for particular of the particles.

The memory subsystem is further for providing data based on the accepted first results to the processing subsystem.

The processor subsystem is further for performing further computations using the accepted first results and producing the second results.

The particle data includes particle location data.

The first results include particle force data.

The second results include particle location data.

In another aspect, in general, a processing node for use in a parallel processing system includes a group of subsystems. This group of subsystems includes a processor subsystem, a computation subsystem, and a memory subsystem. The system also includes a communication subsystem linking the subsystems of the group of subsystems and providing at least part of a link between subsystems of the node and subsystems of other processing nodes of the processing system. The computation subsystem includes circuitry for performing pairwise computations between data elements each associated with a spatial location.

Aspects can include one or more of the following features.

The processor subsystem includes is programmable for substantially general computations.

The processor subsystem includes a plurality of independently programmable processors.

The communication subsystem includes a set of interface units each linked to a subsystem of the group of subsystems, the communication subsystem also including one or more interface units for linking with interface units of other processing nodes.

The communication subsystem includes a communication ring linking the subsystems of the group of subsystems.

The communication system provides addressable message passing between subsystems on the same and on different processing nodes.

The computation subsystem is adaptable for computations involving pairs of particles in a particle simulation system.

The computation subsystem is adaptable for performing computations each involving a particle and a grid location in a particle simulation system.

The group of subsystems and the communication subsystem are integrated on a single integrated circuit.

The memory subsystem includes an interface to a storage device external to the integrated circuit.

The communication subsystem includes an interface for communicating with the communication subsystems on other integrated circuits.

In another aspect, in general, a computation system includes an array of processing modules arranged into one or more serially interconnected processing groups of the processing modules. Each of the processing module includes a storage for data elements and includes circuitry for performing pairwise computations between data elements, each of the pairwise computations making use a data element from the storage of the processing module and a data element passing through the serially interconnected processing modules.

Aspects can include one or more of the following.

The array of processing modules includes two of more serially interconnect processing groups.

At least one of the groups of the processing modules includes a serial interconnection of two or more of the processing modules.

The system further includes distribution modules for distributing data elements among the processing groups.

The system further includes combination modules for combining results of the pairwise computations produced by each of the processing groups.

In another aspect, in general, a processing module includes a set of matching units, each unit being associated with a storage for a different subset of a first set of data elements. The processing module also includes an input for receiving a series of data elements in a second set of data elements, the input being coupled to each of the matching units for passing the received data elements to the matching units. The module also includes a computation unit coupled to the matching units for receiving pairs of data elements selected by the matching units, for each pair, one data element coming from the first set and one data element coming from the second set, and an output for transmitting results produced by the computation unit.

Aspects can include one or more of the following features.

The module includes an output for transmitting the received series of data elements to another module.

The module includes an input for receiving results produced by other modules.

The module includes a merging unit for combining the results produced by the computation unit and the results received on the input for receiving results.

The merging unit includes circuitry for merging results according to a data element of the first set that is associated with each of the results.

In another aspect, in general, a method includes receiving a first set of data elements, distributing the first set of data elements to the storages of an array of processing modules that are arranged into one or more serially interconnected processing groups of the processing modules, receiving a second set of data elements, and passing the data elements through the serially interconnected processing groups. At each of at least some of the processing modules, a pairwise computation is performed involving a data element from the first set that is stored in the storage of the processing module and a data element passing through the processing group, and a result of the pairwise computation is passed through the serially interconnected processing group. The method further includes combining the results of the pairwise computations passed from each of the processing groups and transmitting the combined results.

Aspects can include one or more of the following.

The data elements of the first set and of the second set are associated with bodies in a multiple body simulation system.

The pairwise computation is associated with a force between a pair of the bodies.

The method further includes, at each of the at least some of the processing modules, selecting some but not all of the data elements data elements passing through the processing group for the performing of the pairwise computations.

Selecting the data elements includes selecting the pairs of data elements for the performing of the pairwise computations.

Selecting the pairs of data elements includes selecting the pairs according to separation between spatial locations associated with the data elements.

Distributing the first set of data elements to the storages of the array includes, at each of the modules, distributing data elements to a plurality of matching units, each matching unit receiving a different subset of the data elements.

The method further includes at each of the at least some of the processing modules at each of the matching units selecting some but not all of the data elements data elements passing through the processing group for the performing of the pairwise computations.

The method further includes at each of the at least some of the processing modules combining the outputs of the matching units, and passing the combined outputs to a computation unit for executing the pairwise computation.

In another aspect, in general, a software product is adapted to perform all the steps of any of the above methods. The software product can include instructions for performing the steps embodied on a computer-readable medium.

Other aspects and features are apparent from the following description and from the claims.

DESCRIPTION OF DRAWINGS

FIG. 25 is an algorithm corresponding to the computation schedule in FIG. 24.

FIG. 26 is a graph of computational contributions versus degree of parallelism.

DESCRIPTION

Figures 1, 2:
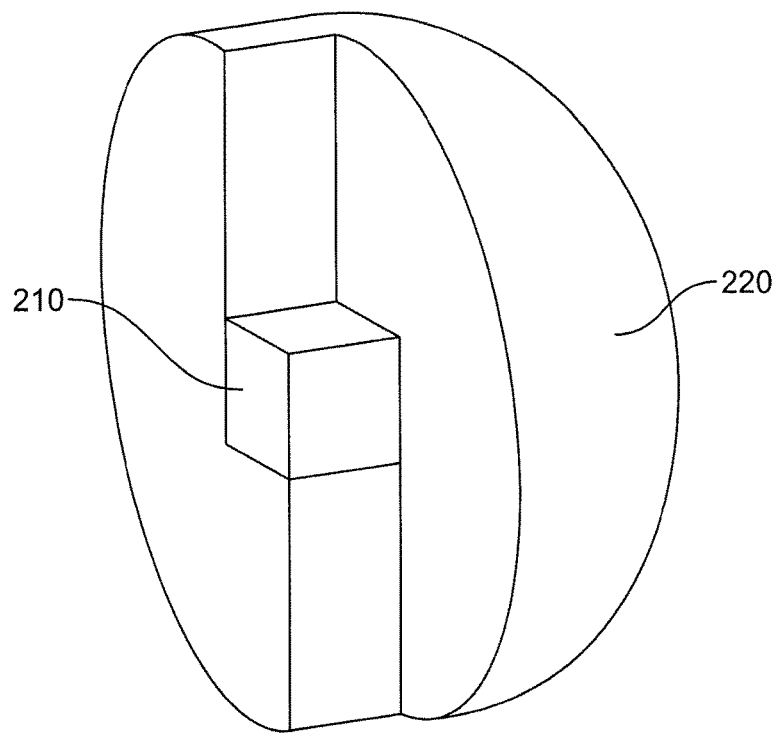
FIG. 1 is a table of asymptotic scaling for various decomposition methods.
FIG. 2 is perspective view of regions for the Half-Shell (HS) method.

Section headings below are provided as an aid to the reader, and should not be construed to limit the description. For example, approaches described in different sections should not be construed to be incompatible based on the section headings. A listing of the section headings is as follows:

1 Overview 24
1.1 Molecular dynamics 24
1.2 Molecular force fields 26
1.3 Pairwise interactions 28
1.4 Mesh based computations 31
1.5 Document organization 33
2 NT, SH, and HS Methods 33
2.1 HS method 35
2.2 NT method 36
2.3 SH method 37
3 Generalized Decompositions 37
3.1 The convolution criterion 40
3.2 Assignment rules 42
  3.2.1 Assignment rules for HS, NT and SH analog methods 42
  3.2.2 Midpoint assignment rule 43
  3.2.3 Pseudo-random assignment rule 45
  3.2.4 Computational load balancing 46
  3.2.5 Translational invariance 50
3.3 Commutative interactions 52
3.4 The rounding criterion 53
3.5 Decompositions in higher dimensions 55
4 Shared communication 59
5 Pair-lists and exclusion groups 63
6 Multiple Zone Methods 66
6.1 A Lower Bound for Import Volume 72
6.2 Optimization Priorities 73
7 Applications of generalized decompositions 74
7.1 Eighth Shell Method 74
7.2 Sliced Half Shell Method 76
7.3 Multiple Zone NT and SNT methods 76
7.4 Foam Method 78
7.5 Comparison of Communication Bandwidth Requirements 79
7.6 Multiple-particle interactions 80
8 Serialized implementation 82
9 Cluster architecture 88
10 Parallel implementation 89
11 Applications 107
12 Alternatives 108

1 Overview

Simulation of multiple-body interactions (often called "N-body" problems) is useful in a number of problem areas including celestial dynamics and computational chemistry. For example, biomolecular or electrostatic particle interaction simulations complement experiments by providing a uniquely detailed picture of the interaction between particles in a system. A significant issue in simulations is the simulation speed.

1.1 Molecular Dynamics

One approach to molecular simulation is primarily physics-based, predicting structure based on a mathematical model of the physics of a molecular system. Proteins may be modeled at the atomic level, with individual atoms or groups of atoms represented as point bodies in an N-body system. One of these methods is molecular dynamics (MD), in which the force on each particle is calculated and Newton's laws are numerically integrated to predict the physical trajectory of each atom over time. An alternative is a class of Monte Carlo methods, which stochastically sample the potential energy surface of a system. Physics-based methods can either be used to refine homology models or be applied on their own, to determine protein structure from scratch. MD can also be used to study the process of protein folding.

One factor in applying physics-based methods to protein structure prediction and other structure-based problems in computational biochemistry is that often these problems are not concerned with any single molecule or molecular event, but rather with the statistical properties of a very large collection of molecules. For instance, when predicting protein structure, we may not necessarily be interested in the structure that one particular protein molecule may happen to fold into, but rather the most probable structure for molecules of that protein, the structure that will be the norm among a large collection of molecules of that protein. When studying binding, the question may not be whether a particular protein and ligand will bind in a particular instance, but the concentration of bound ligands in the steady state, when a large number of proteins and ligands are put together.

A useful quantity to compute for these problems is the free energy of a molecular system. Free energy is not a property of a single state of a system, but rather of an ensemble of states. In very general terms, the lower the free energy of an ensemble of states, the higher the probability that a molecular system will be found in one of those states at any given time. The free energy of an ensemble is computed by summing probabilities over all states in the ensemble. The probability of a state is an exponential function of its potential energy that depends on the temperature of the system (specifically, the calculation uses a Boltzmann distribution). In practical terms, this means that for protein structure prediction, it is insufficient to perform a single run of an MD simulation, stop at some point, and take the end conformation as the native state. At a minimum, many conformations near the end of such a simulation should be sampled. More likely, multiple separate simulations may need to be run and the results compared.

Once the structure of a target protein has been obtained—through either computational or experimental methods—computational methods can be used to predict the protein's interactions with ligands, a task loosely referred to as "the docking problem."

Screening ligands for activity could in theory be done with physics-based methods. Owing to the enormous computational burden of that approach, other methods have been developed. Generally, different configurations of a protein and ligand are generated and a score is calculated for each according to a heuristic scoring function. To reduce the number of configurations that must be tested, the protein is held rigid or allowed a small degree of flexibility; the ligand is tested in various poses and orientations at various points near the protein. To further reduce the configuration space, it is necessary (or at least very helpful) to know the active site on the protein.

This heuristic screening may identify ligands that are likely to bind to a target protein, but it may not quantify that binding or predict other properties of the interaction, such as the concentration of the ligand necessary to produce a certain effect. For this purpose, the binding free energy of the interaction, the free energy difference between the unbound and bound states of the system, can be used. Too small a binding energy can make the required dosage of a drug too high to be practical; too high an energy can cause toxicity or other side effects. Accurate calculation of binding free energy is a significantly more computationally intensive task than simply determining whether two molecules are likely to bind, and relies heavily on accurate structural models of these interactions.

1.2 Molecular Force Fields

In physics-based methods for structure-based problems, the "inner loop" of these computational methods can be chosen to solve the following problem: given a molecular system, calculate either (a) the potential energy of the system as a whole or (b) the force on each particle due to its interactions with the rest of the system. (Note that the force in (b) is simply the three-dimensional vector gradient of (a), making the two variations of the problem similar computationally.) These forces and energies are generally computed according to a particular type of model called a molecular force field.

Force fields can model molecular systems at the atomic level, with atoms or groups of atoms typically represented as point bodies. Each point body has a set of associated parameters such as mass and charge (more specifically a partial charge, so that the complicated electron distribution caused by atomic bonding can be modeled with point charges). These parameters are determined at initialization according to the atom's type and, in standard force fields, remain constant throughout the simulation. Atom type is not as simple as an atomic number on the periodic table: an atom's parameters can depend upon what particles are near it and, in particular, what other atoms are bonded to it. For example, a hydrogen atom bonded to a nitrogen atom (an amine) may have a partial charge that is different than one bonded to an oxygen atom (an alcohol). There can easily be several types each of carbon, hydrogen, oxygen, and nitrogen. The set of atom types and the parameters used for them are one of the characteristics that define a particular force field.

The interactions among atoms can be broken into several components. The bonded terms model the interaction between atoms that are covalently bonded. One such term effectively models a bond between two atoms as a harmonic oscillator, reflecting the tendency for two atoms to settle at a certain distance from each other, known as the bond length. Another term reflects the tendency for two bonds to "bend" towards a certain angle. Yet another term takes into account the effect of torsion, the "twisting" of a bond owing to the relative angles it makes with two bonds on either side of it. Several other types of terms are possible, many of them cross-terms, which take into account the interaction between the basic types of terms. Each term contains one or more parameters, and each parameter must have a value for each combination (pair, triplet, quartet, etc.) of atom types, leading to a profusion of parameters from all of the terms and cross-terms.

The non-bonded terms in a force field model all-to-all interactions among atoms. One of the non-bonded terms calculates the electrostatic interaction of charges attracting and repelling each other according to Coulomb's law. Another type of non-bonded term models the van der Waals interaction, a shorter-range interaction that comprises an attractive component and a repulsive component. The repulsive component dominates at very short distances of a few angstroms (abbreviated Å, , equal to $10^{-10}$ meters). In a rough sense, the repulsive force can be thought of as keeping atoms from overlapping or crashing into one another. There are various ways to model the van der Waals potential. The attractive component is usually modeled as dropping off as the inverse sixth power of the distance between two particles, or $1/r^6$; the repulsive component can be modeled with a similar power function (usually $1/r^{12}$, for computational convenience on general-purpose processors) or with an exponential. Such forces are in contrast the electrostatic potential which drops off more slowly, as $1/r$.

1.3 Pairwise Interactions

Simulations in many fields require computation of explicit pairwise interactions of particles. In addition to the molecular dynamics and Monte Carlo simulations in biochemistry discussed above, similar simulations may be applied to materials science, N-body simulations in astrophysics and plasma physics, and particle-based hydrodynamic and equation of state simulations in fluid dynamics. To reduce the computational workload of such simulations, instead of computing interactions between all pairs of particles, one approach is to compute interactions only between pairs separated by less than some interaction radius, R. These interactions are referred to as "near interactions." The remaining interactions ("distant interactions") are either neglected or handled by a less computationally expensive method. Even with the savings associated with limiting the interaction radius, the near interactions still frequently dominate the computational cost. Methods for decomposing this computation for parallel and/or serial processing can be useful in reducing the total time required and/or computation or communication required for these simulations.

Traditional methods for parallelization are described in a number of review papers, including Heffelfinger, "Parallel atomistic simulations," *Computer Physics Communications*, vol. 128. pp. 219-237 (2000), and Plimpton, "Fast Parallel Algorithms for Short Range Molecular Dynamics," *Journal of Computational Physics*, vol. 117. pp. 1-19 (March 1995).

They include atom, force, and spatial decomposition methods. Spatial decomposition methods can offer an advantage over atom and force decomposition methods because they can exploit spatial locality to only consider pairs of nearby particles rather than all pairs in the system. Force decomposition methods, on the other hand, can offer an advantage over spatial and atom decomposition methods in that the communication bandwidth required by each processor decreases as the number of processors increases.

Two recently developed methods—Snir's hybrid (SH, "hybrid") method, published as "A Note on N-Body Computations with Cutoffs," by Marc Snir (*Theory Comput. Systems* 37, 295-318, 2004) and Shaw's Neutral Territory (NT) method, to be published as "A Fast, Scalable Method for the Parallel Evaluation of Distance-Limited Pairwise Particle Interactions" by David E. Shaw, combine spatial and force decompositions. They have a property that the communications required decreases as the interaction radius decreases. They also have a property that the communication required per node decreases as the number of processors increases. Referring to FIG. 1, a comparison of asymptotic scaling properties of the SH and NT methods with those of traditional methods shows that the SH and NT methods have the same scaling properties, which are significantly better than those of traditional methods. Specifically, both of these two methods have asymptotic complexity of $O(R^{3/2}p^{-1/2})$, which grow more slowly with the number of processors, p, than all but the force method, which does not exploit spatial locality and therefore does not improve as the interaction radius, R, is reduced.

Both the SH and NT methods can offer advantages over traditional methods for practical machine and simulation sizes. For instance, the NT method can be shown to always requires less communication that the SH method, but that the SH method can be optimized using features of the NT method such that the difference was small. An optimized version of the SH method that makes use of features of the NT method is referred to below as the SNT method.

The NT, SNT, and SH methods involve different import regions. That is, the set of particles imported by each processor differs from one method to another. The methods, however, share a number of features. In both the NT method and the SH method, each processor stores the particles falling in some rectangular box. In both methods, the processor that computes the interaction between a pair of particles typically is not the one on which either particle resides, but instead a third processor that imports both of the particles of the pair. In both methods, each processor imports particles from two interaction zones and considers all pairs of particles such that one particle is in one interaction zone and the other particle is in the other interaction zone.

The description below addresses a general class of methods that includes traditional spatial decompositions, the SH method, the NT method, and the SNT method as special cases. The communication requirements of a variety of specific instances of the general class are analyzed taking into account both latency and bandwidth of the interprocessor communication network.

A criterion for selecting parameters of a particular method can depend on the properties of both the physical system to be simulated (e.g., system dimensions, interaction radius) and the hardware available for the simulation (e.g., number of nodes, network topology, and memory structure including cache structure and sharing between nodes). For most practical parameter settings, the method that delivers the best performance according to such a criterion generally is not necessarily one of the specific methods described above, but rather is a different instance of the general class of methods.

1.4 Mesh Based Computations

As introduced above, distant interactions between particles, for example, between particles separated by more than the maximum interaction radius, can be computed using less computationally expensive methods. One such approach is based on the Ewald Method, as described in detail in copending applications U.S. application Ser. No. 11/171,619, U.S. application Ser. No. 11/171,634, International Application No. PCT/US2005/023184.

The essence of the Ewald method is to split the electrostatic potential field into two main parts, one of which can be computed efficiently in real space (by calculating pairwise interactions) and the other of which can be handled efficiently in the Fourier domain using computations on a regular grid on the simulation region. (Note, however, that not all variations on Ewald use the Fourier domain.)

Implementation of the part involving the Fourier domain calculations can be divided into three phases. First, a discrete charge distribution $$\rho(r) = \sum_{i=1}^{N} \sum_{n} q_i \delta(r - r_i - nL)$$

that is defined on the (infinite and periodic) continuous three-dimensional space r, is mapped to a charge distribution $\rho^S(r_m)$ defined on the finite three-dimensional mesh according to $$\rho^S(r_m) = S \otimes \rho = \int_{-\infty}^{\infty} S(r_m - r)\rho(r)d^3r = \sum_{i=1}^{N} \sum_{n} q_i S(r_m - r_i - nL) \approx \sum_{i=1}^{N} q_i S(r_{im}^{min})$$

where S is a charge spreading function, the operator $\otimes$ denotes spatial convolution, m is an index for mesh points that lie within the primary box, and the vector $r_{im}^{min}$ is the vector from mesh point m to the nearest image of particle i.

In a second phase, a potential function $\phi^*(r_m)$ is computed at the grid locations using a convolution operation on the charge distribution $\rho^S(r_m)$. This convolution can be implemented using Fast Fourier Transform (FFT) techniques.

In the third phase, energy or force quantities defined at the particle locations are found using a convolution approach that maps the mesh-based potential function to those locations. In particular, the force on the $i^{th}$ particle can be computed as $$F_i^\sigma = q_i F^\sigma(r_i)$$

where $F^\sigma = T' \otimes \phi^*$ and $$T'(r) = \frac{d}{dr} T(r).$$

This third phase can be implemented as a sum $$F_i^\sigma = q_i h^3 \sum_{m(r_i, T)} \phi^*(r_m) T'(r_{im}^{min}).$$

Note that computationally, the first phase and the third phase involve sums involving pairs of locations, with one location of each pair being a particle (i) location and the other location of the pair being a location of a mesh point (m).

1.5 Document Organization

The remainder of this document is organized as follows. Sections 2 through 7 generally relate to algorithms that are applicable to computing range-limited pairwise interactions between particles, or more generally, to performing range-limited computations associated with pairs of points in space, where the pair may correspond to a pair of particles in an N-body problem, or the pair may correspond to one grid point and one particle point, for example, as part of a charge spreading or force interpolation method.

Sections 8 through 10 relate to software and hardware techniques, which may be applicable to the algorithms presented in Sections 2 through 7, or to an overall n-body simulation implementation. Note that the hardware techniques described, for example in Section 10, have aspects that are applicable to a much broader range of applications than n-body simulation.

Possible applications of the algorithms and software and hardware techniques are discussed briefly in Section 11.

2 NT, SH, and HS Methods

The recently presented NT and SH methods, as well as an example of a conventional spatial decomposition method, the "Half-Shell" or HS method, can be described in the following framework. We assume that the system of particles (bodies) being simulated resides within a rectangular box called the global cell. In all three methods, we divide the global cell into a regular, rectangular, three-dimensional grid of smaller boxes. We refer to these smaller boxes as homeboxes. In one parallel implementation, we assign a one-to-one correspondence between homeboxes and processors, and we refer interchangeably to a processor and its homebox. The methods are described below in the content of such an implementation, with some alternative implementations being presented after this discussion.

Also, when we refer to a homebox or processor importing particles, this should be understood to include a processor receiving information characterizing those particles, such as their location, physical attributes, identities, etc. Each processor is responsible for updating the position of the particles that lie within its homebox at any point in time. As a convention, the base coordinates of a given home box (or of any particle within that homebox) are defined as the coordinates of the low-coordinate corner of that homebox. The logical coordinates of a homebox or particle are the integer mesh coordinates of the homebox. The dimensions of each homebox are $h_x \times h_y \times h_z$.

Each home box has an associated import region consisting of the region of space from which the processor must import particles. Each home box imports all particles not already present within that homebox that are to be interacted in the home box. The NT, SH, and HS methods each use different import regions.

The NT, SH, and HS methods each interact all particles in one volume of space with all particle in another volume of space. We refer to these volumes as "interaction zones" or simply "zones." In each of these methods, the intersection of the two zones is the homebox.

We use the volume of the import region associated with each homebox as a simple model for (i.e., a proxy for or an estimate of) the communication bandwidth required by pairwise particle interaction method. Such a proxy is most accurate for a fully connected network topology.

2.1 HS Method

In conventional decompositions, generally, two particles are interacted in the homebox in which one of them resides. In the HS method specifically, the location where a pair of particles are interacted follows the following rule: the particles are interacted in the homebox with the smaller x base coordinate; if the two particles have the same x base coordinate; the particles are interacted in the homebox with the smaller y base coordinate; if they also have the same y base coordinate, they are interacted in the homebox with the smaller z base coordinate. If they also have the same base z base coordinates, they are in the same homebox and the interaction is computed there. Interactions between particles on the same homebox are referred to as "local interactions" while interactions between particles on different homeboxes are referred to as "remote interactions."

Referring to FIG. 2, as a result of the rule, each homebox has an import region that consists of half the points external to the homebox within a distance R of the boundary. Every particle in the import region 220 interacts with every particle in the homebox 210. Every particle in the homebox 210 also interacts with every other particle in the homebox 210. Equivalently, the two interaction zones are the homebox and the union of the homebox with the half shell.

The conventional HS method is guaranteed to consider all unique pairs separated by less than R. The method also could interact some pairs whose separation exceeds R due to the finite volume of the homebox. These "excess interactions" can be eliminated ("filtered") at the pair level as necessary. Local interactions will also need filtering to avoid double counting interactions between local particles. Such filtering can be accomplished by a test within an inner loop of a nested computational iteration of particles.

2.2 NT Method

In the NT method, two particles interact in a homebox that has the x and y base coordinates associated with one particle and the z base coordinate associated with the other particle. More specifically, the x and y base coordinates of the homebox in which the particles interact are those of the particle with the smaller x base coordinate or, if both particles have the same x base coordinate, those of the particle with the smaller y base coordinate. The z base coordinate of the homebox in which the particles interact is the z base coordinate of the other particle. If two particles have the same x and y base coordinates, they are interacted on the homebox of the particle with the lower z coordinate.

Figure 3:
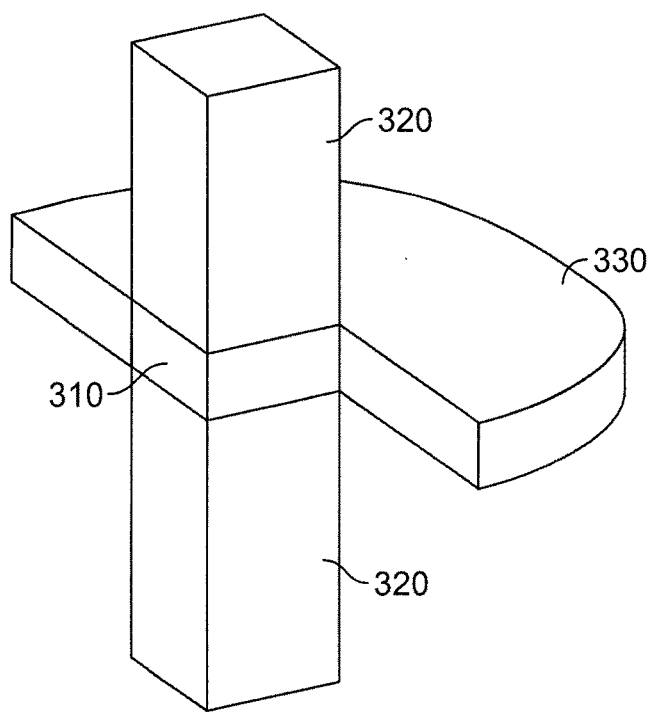
FIG. 3 is perspective view of regions for the Neutral Territory (NT) method.

Referring to FIG. 3, the resulting import region of each homebox is the union an "outer tower" 320 and an "outer plate" 330. The outer tower comprises all points that lie directly above or below the homebox 310 within a distance R of the boundary. The outer plate 330 comprises half the points external to the homebox 310 that lie in its z-plane within a distance R of the boundary. The interaction zones are the "tower," which consists of the union of the homebox 310 and the outer tower 320, and the "plate," which consists of the union of the homebox 310 and the outer plate 330.

By interacting the tower (310, 320) with the plate (310, 330), all near interactions are guaranteed to be computed at least once. However, to ensure that each near interaction is computed only once, a filtering criterion is used that is not required in the HS method. Namely, local (i.e., homebox) plate particles should only interact with local tower particles and remote (i.e., non-homebox) particles in the upper half of the outer tower (or lower half, but not both).

The import requirements of the NT method can be reduced by an appropriate choice of the aspect ratio of the homebox appropriately. An optimum occurs when $h_x = h_y > h_z$.

That is, an optimum occurs when the homeboxes are "flattened" in the z dimension by an amount that depends on the interaction radius and the homebox volume, and generally corresponds to the tow interaction zones having equal or approximately equal volumes.

2.3 SH Method

Figure 4:
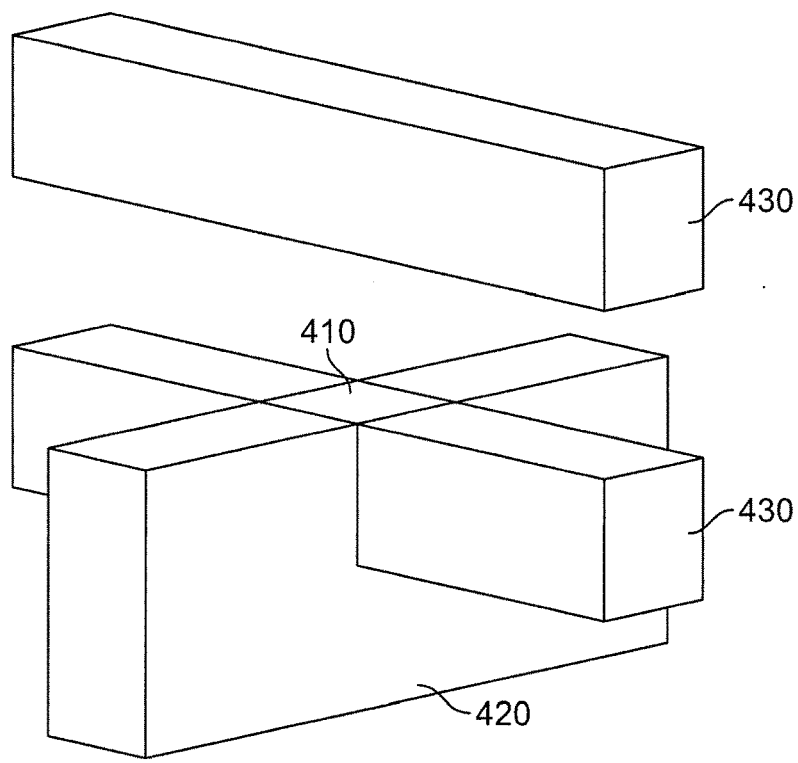
FIG. 4 is perspective view of regions for the Snir's Hybrid (SH) method.

The SH method assumes a cubical homebox of side length h. We define $r=\lceil R/h \rceil$ and $r \% = \lceil \sqrt{r+1} \rceil$. Referring to FIG. 4, the import region of the homebox 410 with logical coordinates (i, j, k) (including the homebox) consists of the union of two interaction zones. The first interaction zone is a contiguous region that we refer to as the "base" 420 and consists of the set of homeboxes with logical coordinates $(i+u, j, k-w_1)$ where $u \in [-r, r]$ and $w_1 \in [0, r^0/-1]$. The second interaction zone is a set of non-contiguous regions that we refer to as the "comb" 430. It consists of the set of boxes with logical coordinates $(i, j+v, k+w_2 r^0/)$, where $v \in [-r, r]$ and $w_2 \in [0, \lfloor r/r \% \rfloor]$. Note that both the comb 430 and the base 420 include the homebox 410. Interacting the comb 430 and base 420 ensures that all near interactions will be computed at least once. As for the HS and NT methods, filtering can be used to ensure that all near interactions are computed exactly once and that only near interactions are computed.

3 Generalized Decompositions

In a generalized class of methods, each processor imports particles from two interaction zones and interacts particles from one zone with particles from the other zone. The pairs of zones are chosen for the implementation of the method to ensure that all near interactions are computed. Both the case where each particle interacts with other particles in a surrounding cube, and the case where each particle interacts with other particles in a surrounding sphere are considered. Because a spherical region of radius R has roughly half the volume of the circumscribing cube of side length 2R, "rounding" allows reduction in communication bandwidth requirements.

For clarity of exposition, we initially consider a simplified problem in which:

A. The particles are restricted to the two-dimensional x-y plane.
B. A pair of particles interact if and only if they are separated by a distance less than R in the x-dimension and by a distance less than R in the y-dimension (that is, the Euclidean distance may be greater than R)
C. The homeboxes are square with side length h, and R is an integer multiple of h. Likewise, the interaction zones consist only of complete homeboxes ("voxelized method").
D. The interactions are non-commutative. Thus, for a pair of particles a and b, we must separately compute the influence of a on b and the influence of b on a. (Note that the force between two particles is usually treated as a commutative interaction as by Newton's Third Law, the force due to an interaction on particle a is equal and opposite the force on particle b. Non-commutative interactions are also of practical interest; for example, one might want to compute the influence of each particle on nearby mesh points.)

These simplifications are progressively relaxed below after an initial discussion of the simplified problem.

The interaction neighborhood of a homebox is defined to be the smallest region of space that is guaranteed to contain all particles with which any arbitrary local particle (i.e., any particle in the homebox) could interact. In this simplified problem, the interaction neighborhood is a square of side length 2R+h extending a distance R beyond the homebox in the positive and negative x and y directions. Particles in the homebox influence particles in the interaction neighborhood and vice versa.

Figure 5:
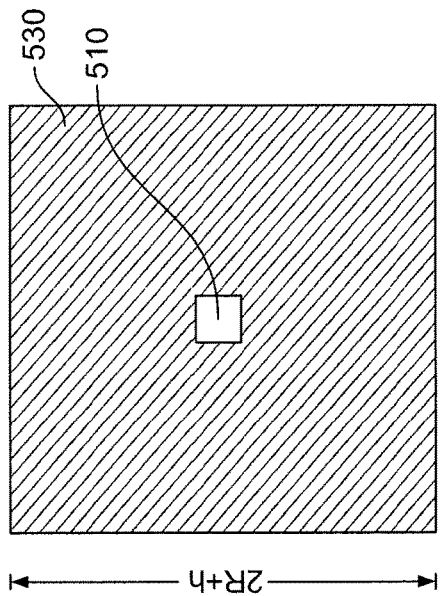
FIG. 5 is a view of regions in a simplified two-dimensional analog of the Half-Shell (HS) method.

Referring to FIG. 5, a simplified analog to the HS method (more of a "full" shell than a "half" shell approach in view of the non-commutative assumption D above) involves each homebox 510 computing the influence on its own particles of all particles in its interaction neighborhood 530. This method requires that each homebox import all the particles in its interaction neighborhood, except of course for those that already reside in the homebox.

Figure 6:
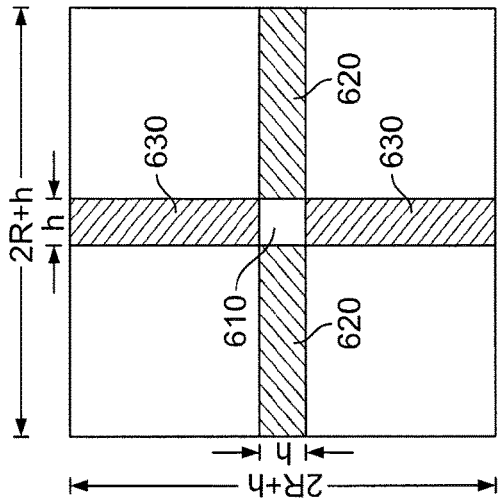
FIG. 6 is a view of regions in a simplified two-dimensional analog of the Neutral Territory (NT) method.

Referring to FIG. 6, a simplified analog to the NT method involves each homebox 610 computing the influence of all particles in a row of neighboring boxes 620 that span the interaction neighborhood horizontally on all particles in a column of neighboring boxes 630 span the interaction neighborhood vertically. Each homebox imports both the remote particles in the row of boxes 620 and the remote particles in the column of boxes 630. The import requirements for this method are significantly lower than those of the HS analog, even though the total number of interactions computed is the same.

Note that in both of these methods, each homebox computes the influence of all particles in one region of space, the interaction zone consisting of homebox 510 and boxes 620, on all particles in another region of space, the interaction zone consisting of neighborhood 530 and boxes 630. In these examples, the two zones of each method overlap. Their intersection is the homebox 510, 610. The zones are translationally invariant in the sense that each homebox 510, 610 has the same relative spatial relationship with its two associated zones.

Figure 7:
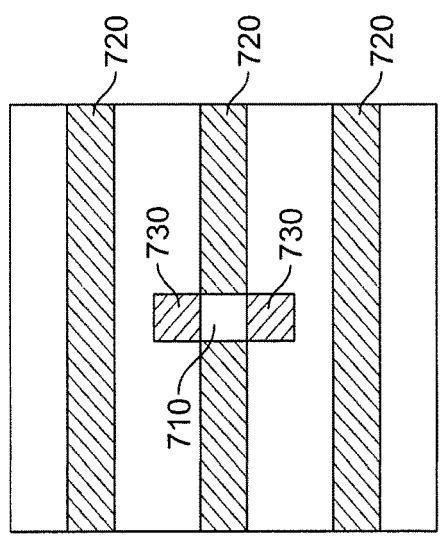
FIG. 7 is a view of regions in a two-dimensional decomposition that shares some characteristics with the Snir's Hybrid (SH) method.

Other choices for the two interaction zones lead to alternative decompositions. Referring to FIG. 7, a decomposition (referred to below as the "SH analog") that shares some characteristics with the SH method has one zone comprised of a set of equally spaced horizontal slabs 720, while the other zone that is comprised of a vertically oriented block 730 whose height is equal to the spatial period of the slabs. Again, each homebox 710 imports the particles in the two zones (720, 730) and computes the influence of particles in the one zone 720 on particles in the other zone 730.

Figure 8:
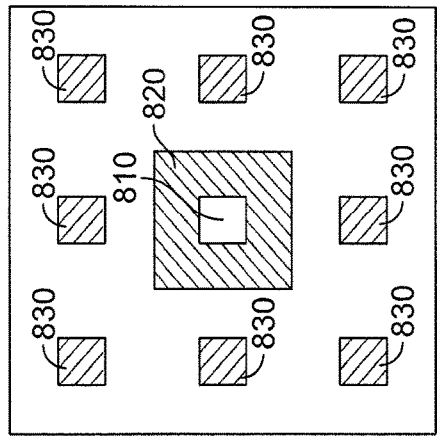
FIG. 8 is a view of regions in a two-dimensional decomposition.

Referring to FIG. 8, in another decomposition, one zone 820 comprises a square area, a "brick," centered on the homebox 810. The other zone 830 is a "foam"-like structure that consists of boxes the size of the homebox positioned such that their period in each dimension is equal to the width of the zone 820. The homebox 810 computes the influence of each particle in the zone 820 on each particle in the zone 830.

3.1 The Convolution Criterion

Given a pair of translationally invariant zones associated with each homebox, verification that all required interactions are computed can be performed using a convolution-based criterion. We define the reception region of a method as the region of space that influences the homebox. Specifically, the reception region is the smallest volume of space that is guaranteed to contain all remote particles that influence local particles if no additional filtering at the pair level is employed. The criterion is based on ensuring that the reception region of a homebox includes its entire interaction neighborhood.

To find the reception region, assume each homebox has two translationally invariant types of interaction zones associated with it, its "blue" zones and its "red" zone. The homebox computes the influence of each particle in its red zones on each particle in its blue zones. We first find the set of homeboxes whose associated blue zone includes the designated homebox. We then take the union of the red zones for all homeboxes in this set to obtain the reception region of the designated homebox.

To compute the reception region graphically, we first reflect the blue zone about the designated homebox to show the set of homeboxes whose blue zones include the designated homebox. In two dimensions, reflection about the designated homebox is equivalent to a 180° rotation about the designated homebox. We then translate the red zone such that it has the same spatial relationship to each homebox in the reflected blue zone that it initially had to the designated homebox. The reception region is the union of these translated red zones.

This process is similar to a convolution operation. Technically, the reception region is the support of the discretized convolution of an indicator function over the reflected blue zone with an indicator function over the red zone. For that reason, we term the criterion that the reception region includes the entire interaction region the "convolution criterion." For the four decompositions illustrated in FIGS. 5 through 8, the reception region of the homebox is identical to its interaction neighborhood.

Figure 9:
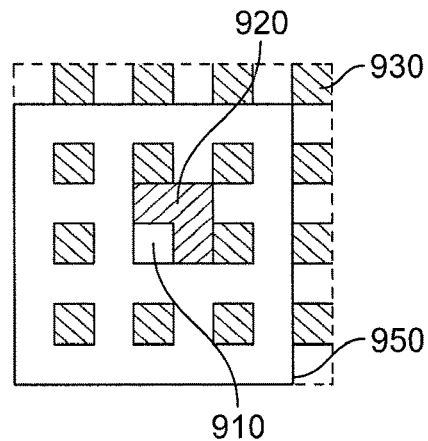
FIG. 9 is a view of regions in a two-dimensional decomposition.
Figure 10:
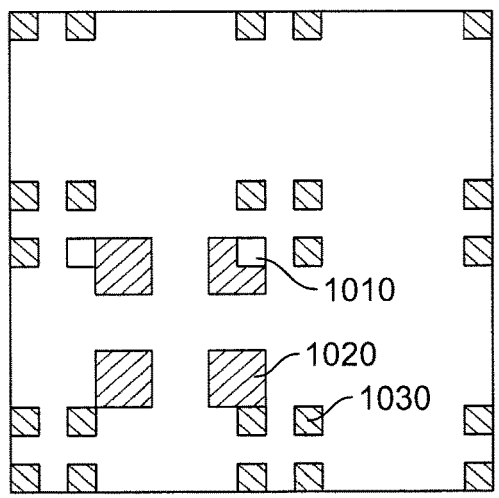
FIG. 10 is a view of regions in a two-dimensional decomposition
Figure 11:
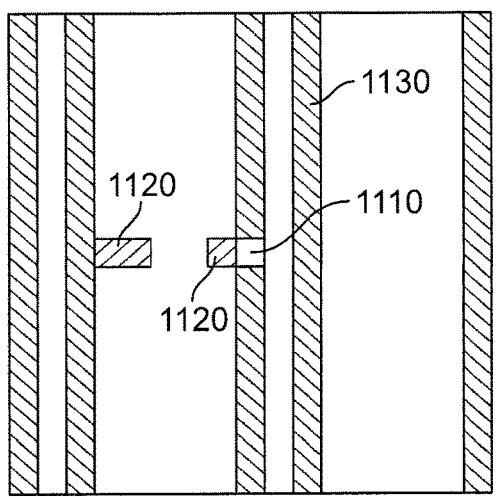
FIG. 11 is a view of regions in a two-dimensional decomposition

Referring to FIGS. 9-11, several other decompositions that also satisfy the convolution criterion. The decomposition shown in FIG. 9 is similar to that of FIG. 8, but here, the two interaction zones 920 and 930 associated with a particular homebox 910 are not centered on that homebox 910. Symmetry of the zones about the homebox is not required. The zone 920 extends up and to the right of the homebox 910. Note that when reflected, the zone 920 extends down and to the left of the homebox. The decomposition of FIG. 9 also differs from those of FIGS. 5-8 in that the reception region of the homebox is larger than its interaction neighborhood and in that parts of the zone 930 lie outside the interaction neighborhood 950 (indicated by the solid outlined square). If one were to eliminate the parts of the zone 930 that are outside the interaction neighborhood 950, the reception region would no longer cover the entire interaction neighborhood, so the decomposition would no longer ensure that all required interactions were computed.

FIGS. 10 and 11 show two other decomposition schemes that also satisfy the convolution criterion. In FIG. 10, neither of the zones 1020 or 1030 for the homebox 1010 is contiguous. Similarly, in FIG. 10, the zones 1120 and 1130 of homebox 1130 are not contiguous.

3.2 Assignment Rules

Decompositions can be described in terms of interaction zones associated with each homebox. An alternative description takes the form of an assignment rule, which specifies the processor that will compute the influence of one particle on another as a function of their locations or on the processors on which they initially reside. Such a description was informally used in describing some of the methods, including the previously presented HS and NT methods above.

Suppose that particles a and b are separated by a distance no greater than R in each dimension. We denote the spatial coordinates of particles a and b by $(x_a, y_a)$, and $(x_b, y_b)$, respectively, and denote the logical coordinates of the homebox of particle a, the homebox of particle b, and the homebox that computes the influence of a on b by $(i_a, j_a)$, $(i_b, j_b)$, and $(i_{a \to b}, j_{a \to b})$, respectively. An assignment rule can be specified as $(i_{a \to b}, j_{a \to b})$ in terms of the homeboxes $(i_a, j_a)$ and $(i_b, j_b)$ that contain the particles, or in terms of the locations $(x_a, y_a)$, and $(x_b, y_b)$ of the particles.

3.2.1 Assignment Rules for HS, NT and SH Analog Methods

For the simplified analog of the HS method, which is illustrated in FIG. 5, the assignment rule can be represented as $(i_{a \to b}, j_{a \to b}) = (i_b, j_b)$. For the simplified analog of the NT method, which is illustrated in FIG. 6, the assignment rule can be represented as $(i_{a \to b}, j_{a \to b}) = (i_a, j_b)$.

To specify the assignment rules for the decomposition schemes illustrated in FIGS. 7 and 8, we define the functions r and g, which are used in the specification of the assignment rule, for integer arguments as:

$$r(m) = \begin{cases} 1 & \text{if } \exists k \in Z \text{ such that } m = 3k + 1 \\ 0 & \text{if } \exists k \in Z \text{ such that } m = 3k \\ -1 & \text{if } \exists k \in Z \text{ such that } m = 3k - 1 \end{cases}$$

$$g(m, n) = m + r(n - m)$$

The assignment rule for the decomposition scheme of FIG. 7, the SH analog, can be represented as $(i_{a \to b}, j_{a \to b}) = (i_b, g(j_b, j_a))$. The assignment rule for the foam-like scheme, which is illustrated in FIG. 8, can be represented as $(i_{a \to b}, j_{a \to b}) = (g(i_b, i_a), g(j_b, j_a))$.

3.2.2 Midpoint Assignment Rule

The assignment rule can also be specified in terms of the locations of the particles a and b. For example, if mid(a, b) is used to denote a point at the geometric midpoint between the coordinates of a and b (i.e., $x_{mid(a,b)} = (x_a + x_b)/2$), then the assignment rule can be represented as $(i_{a \to b}, j_{a \to b}) = (i_{mid(a,b)}, j_{mid(a,b)})$. More generally, a midpoint mapping m(a, b) from the coordinates of the particles to another point ("a mid location") in the space can be used that is not necessarily the geometric midpoint of the points, and a midpoint rule can be applied to three or more points with a suitable definition of a "midpoint." For example, a midpoint of a set of points may be defined as the center of the smallest sphere containing all the points. As another example, an average location (e.g., for each coordinate direction averaging the coordinates of the points in the set).

Given an assignment rule and the interaction radius R, the import region necessary to satisfy the rule can be determined based on the rule. The assignment rule is a many-to-one mapping from pairs of particle locations to logical homebox coordinates. For any homebox in the range of the mapping, the inverse in the domain of pairs of particle locations is well defined. This inverse defines the import region for the homebox through the union of the domain of each coordinate of the pairs in the inverse. The inverse can be specified either according to the coordinates of the particles, or in terms of their logical (homebox) coordinates. The existence of an assignment rule that is defined on the entire domain of pairs of particle locations with the global cell guarantees that each pair of particles will interact on some processor, so application of the convolution criterion is not necessary in this case.

Note that in the case of the midpoint assignment rule using the geometric midpoint mid(a,b) above, the import region extends at most a distance R/2 away from the homebox, because if one of the particles is further than R/2 away from the homebox and the particles are geometrically separated by at most R, then the midpoint necessarily falls outside the homebox.

Figure 36:
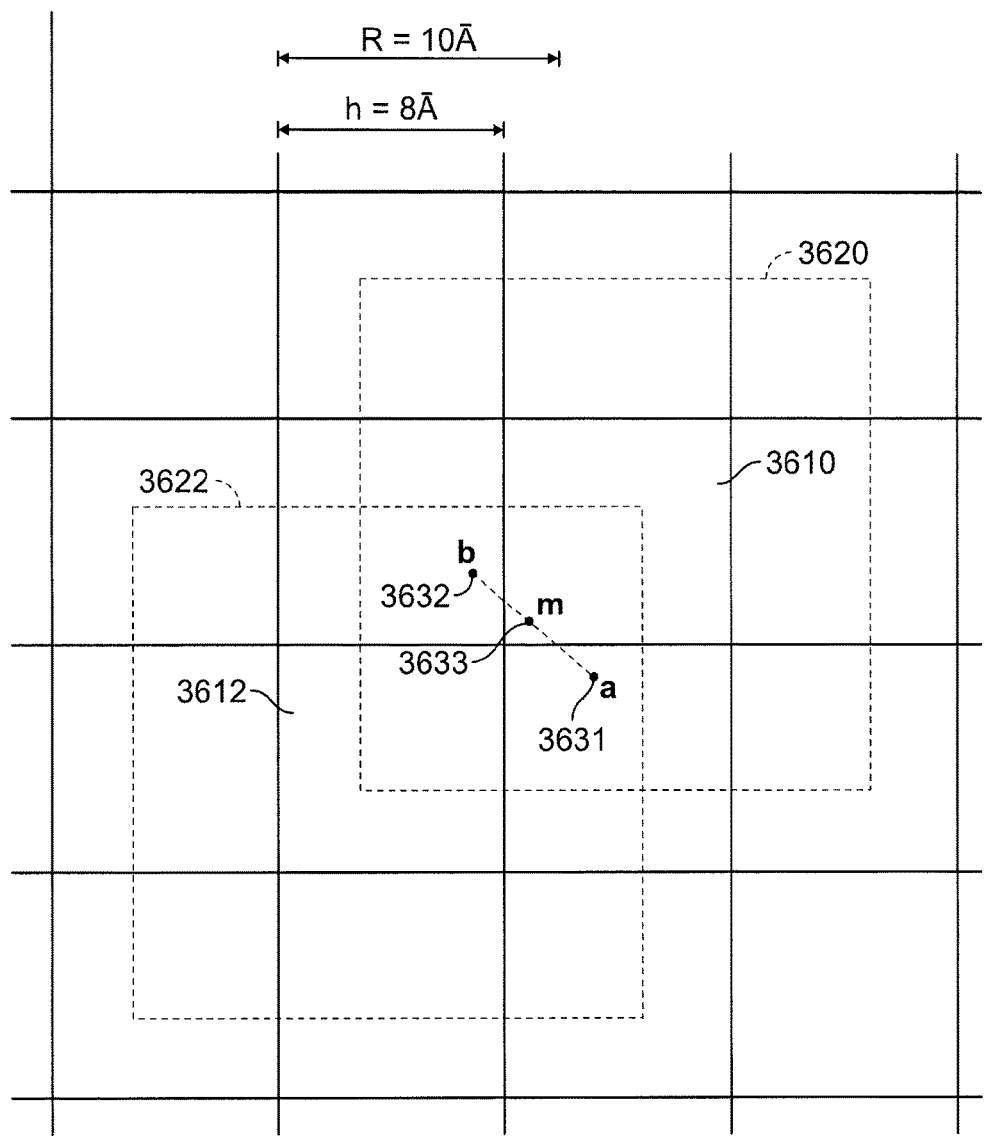
FIG. 36 is a view of regions in a two-dimensional pseudo-random assignment method.

Referring to FIG. 36, a two-dimensional example uses an array of square homeboxes, each of which is h=8 Å on each side. A homebox 3610 is a representative homebox, with the solid lines delineating the homeboxes. In this example, the interaction radius is R=10 Å. As presented above, the interaction region 3620 extends R/2=5 Å around homebox 3610. A representative pair of particles, a 3631 and b 3632 has a geometric midpoint m 3633 that falls within the homebox 3610, and therefore the computation of the interaction between a and b is computed by the processor assigned to that homebox.

The midpoint method can also handle interactions that involve sets of three or more particles. Suppose that we wish to compute interactions between all sets of m particles that fall within some sphere of radius R/2 (if m=2, this is equivalent to the statement that we wish to compute interactions between all pairs of particles separated by less than a distance R). In the midpoint method, the interaction between a set of m particles is computed on the processor that contains their midpoint, defined, for example, as the center of the smallest sphere that contains all m particles. The import region of the midpoint method in the m-particle case is identical to that for the two-particle case.

3.2.3 Pseudo-Random Assignment Rule

For a particular import region defined for each homebox, quite frequently the necessary particle data for an interaction is imported to or already available on more than one node. For example, in the example shown in FIG. 36 with a homebox size of h=8 Å with a R=10 Å interaction radius, the data required for the interaction between particles a 3631 and b 3632 is also available to the processor with homebox 3612, which has an import region 3622. In general, in this example, data for any pair of particles is available to nodes associated with up to $9=3^2$ homeboxes (in a three dimensional version, $27=3^3$ homeboxes). For most of the interactions in this particular case, there are at least two nodes that could perform the interaction and there are quite frequently many, many more.

An approach to assigning the computation to one of the nodes that has the data for a pair of particles does not necessarily use the midpoint node. Rather, in this approach, the computation is assigned in a generally uniform pseudo-random manner from a set of possible nodes such that at least one node and preferably only one node performs the calculation. For example, each processor that has the data for those particles makes a pseudo-random determination using little if any communication between the nodes to determine whether it should perform the calculation. In the case where only one node can compute the interaction, in this example, that node contains the midpoint of the particle locations.

A specific way of implementing the pseudo-random determination involves the data for a particle that is distributed by its homebox including a bitvector which indicates which nodes have copies. For a particular pair of particles, the logical AND of the bitvectors provides the indication of the nodes that have copies of the data for both the particles. The number of such nodes that has the data for both particle a and b is defined to be the n_cc(a,b). Using a same random number generator, each node with copies of the particles generates the same pseudo-random number in the range 0 to n_cc(a,b)−1. This random number is used to identify the node that will perform the computation based on the ANDed bitvectors (e.g., identifying the bit position of the n_cc$^{th}$ set bit). One way of implementing the pseudo-random number generator uses quantities associated with the specific particles as seeds. For example, each particle has a global index, $index_a$, $index_b$, respectively, and the pseudo-random number generator is implemented as symmetric_hash($index_a$, $index_b$) MOD rank(a, b), where symmetric_hash(n, m) can be a hash function implemented using any of a number of well-known techniques As another variant, of this approach, the pseudo-random function is not necessarily uniform. For example, if a goal is the spread out the computations on available nodes that have the needed data, the random function is biased to nodes that have relatively few pairs of particles to choose from. This type of bias can be incorporated by providing shared load information to the nodes, or by providing information from the sending nodes related to the number of particles for which data is being sent to other nodes.

3.2.4 Computational Load Balancing

In an approach related to the pseudo-random assignment rule discussed above, the fact that multiple nodes in general are available to perform each pairwise computation is used for load balancing, with the nodes cooperating to determine which computations are performed at which node in such a way that each computation is performed only once, and a desirable balancing of computational load is achieved. We refer to a class of methods as "midpoint assured methods" where each processor imports the same data as would be imported in the midpoint method described above, but the assignment of interaction computations to processors is adjusted in such a way that the computation load is more even across the processors.

For expository simplicity, we first describe this method for a one-dimensional space where each "box" is simply an interval of length b. We also assume that R is no greater than b, where a set of m particles interact if they all fall within some sphere of radius R/2. We number the processors such that the home box of processor i is the ith box from the left. The computation proceeds in the following manner:

First, each processor imports all remote particles within a distance R/2 of its home box.

Each processor then finds its set of locally computable interactions, consisting of all combinations of m particles available to that processor that fall within a sphere of radius R/2. Each processor i divides its set locally computable interactions into three nonoverlapping subsets: interactions that are also computable on its left neighbor (processor i−1), interactions that are also computable on its right neighbor (processor i+1), and interactions that are only computable on processor i. We denote these subsets $L_i$, $R_i$, and $C_i$, respectively, and we denote their sizes by $l_i$, $r_i$, and $c_i$. $R_i$ and $L_{i+1}$ contain exactly the same elements, namely all combinations of m particles that are within a distance R/2 of the boundary between box i and box i+1, so $r_i = l_{i+1}$.

Each processor i then sends the value of $c_i$ to its left and right neighbors. This is the only communication required by this parallelization method beyond that required by the basic midpoint method. Each processor i now has the values of $c_{i-1}$ and $c_{i+1}$ as well as $c_i$, $l_i$, and $r_i$.

Each processor i then determines which of the interactions in $L_i$ and which of the interactions in $R_i$ it will compute, and which of these interactions it will leave to its neighbors to compute. In order to ensure that each interaction is in fact computed somewhere, neighboring processors must make consistent decisions about the division of labor between them. Processors i and i+1 both have access to the values of $c_i$, $c_{i+1}$, and $r_i$ (because $r_i = l_{i+1}$). Processor i will compute the first $k_i$ interactions in $R_i$, while processor i+1 will compute the last $r_i - k_i$ interactions, where processors i and i+1 independently compute identical values for $k_i$ based on $c_i$, $c_{i+1}$, and $r_i$. To avoid missing or duplicating computation of any interaction, processors i and i+1 agree on the order of the interactions in the equivalent sets $R_i$ and $L_{i+1}$; such a consistent ordering might be based on the positions of the particles involved in each interaction, with ties broken by other particle characteristics such as charge. In the absence of prior statistical information about the spatial distribution of particles, we might compute $k_i$ as $$k_i = \max\left(0, \min\left(r_i, \text{round}\left(\frac{r_i}{2} + \frac{c_{i+1} - c_i}{3}\right)\right)\right)$$

That is, if $c_{i+1}$ and $c_i$ are identical, then we assume that processors i and i+1 have a comparable load, and we therefore split the interactions in $R_i$ evenly between them. If $c_{i+1} > c_i$, then we assign more than half the interactions in $R_i$ to processor i, in an attempt to balance the load. The max, min, and round operations in the above equation are necessitated by the fact that $k_i$ can only take on integer values between 0 and $r_i$. In the absence of such restrictions, distributing interactions according to the formula $$k_i = \frac{r_i}{2} + \frac{c_{i+1} - c_i}{3}$$

for all i would result in the assignment of an identical number of interactions to processors i and i+1, if $c_{i-1}$ and $c_{i+2}$ were both equal to the average of $c_i$ and $c_{i+1}$. This average represents a reasonable estimate of $c_{i-1}$ and $c_{i+2}$ based on information to which processors i and i+1 both have access. Better load balancing could be achieved if both processors had access to $c_{i-1}$ and $c_{i+2}$, or if processors had some prior statistical information about the particle distribution (e.g., the average particle density).

Generalizations of this method to higher dimensions can take several forms. A computationally efficient and easily implemented generalization is available if we expand the import region slightly such that its outer boundary is a rectangular parallelepiped extending a distance R/2 beyond the interaction box in the positive and negative directions along each coordinate axis. We describe this generalization in the two-dimensional case, where the outer boundary of the import region will be a rectangle (a square if the interaction box is a square). Assuming that the side lengths of the interaction box are all larger than the import radius R, an individual interaction may be computable on four boxes that share a common corner, on two boxes that share a common edge, or only on a single box. Our strategy is first to assign each interaction that can be computed by two or four boxes in neighboring columns to a unique column, and then to assign interactions that can be computed by boxes in neighboring rows to a unique row. We perform these assignments by repeated application of a procedure similar to that used to split $R_i$ in the one-dimensional case, with appropriate values substituted for $r_i$, $c_i$, and $c_{i+1}$ in Equation 1.

More specifically, we assume that processor (i,j) is in the ith row and the jth column. After importing particles in its import region, processor (i,j) divides its set of locally computable interactions into nine subsets, based on which other processors can compute them. We denote these subsets by $S_{i,j}^{a,b}$, where a and b can each take on the values −1, 0, or 1. The value of a indicates whether the interactions in $S_{i,j}^{a,b}$ can be computed by processor (i−1, j) (in which case a=−1), by processor (i+1,j) (in which case a=1), or neither (in which case a=0). The value of b indicates whether the interactions can be computed by processor (i,j−1) (in which case b=−1), by processor (i, j+1) (in which case b=1), or neither (in which case b=0). The shape of the import region implies that an interaction is in $S_{i,j}^{1,1}$ if and only if it is computable in both processors (i,j) and (i+1,j+1) (this would not be the case if the import volume were restricted to that of the midpoint method). Neighboring processors agree on their set of shared elements; for example, $S_{i,j}^{1,1}$ contains the same elements as $S_{i+1,j+1}^{-1,-1}$, $S_{i+1,j}^{-1,1}$, and $S_{i,j+1}^{1,-1}$. We denote the size of $S_{i,j}^{a,b}$ by $s_{i,j}^{a,b}$.

Each processor (i,j) sends the values $s_{i,j}^{1,0}$, $s_{i,j}^{0,0}$, and $s_{i,j}^{-1,0}$ to processors (i,j−1) and (i,j+1). For each a in {−1, 0, 1}, we assign the first $k_{i,j}^{a,1}$ interactions in $S_{i,j}^{a,1}$ to processors in column j and the last $s_{i,j}^{a,1} - k_{i,j}^{a,1}$ to processors in column j+1, where $k_{i,j}^{a,1}$ is computed by Equation 1 with $s_{i,j}^{a,1}$ substituted for $r_i$, $s_{i,j}^{a,0}$ substituted for $c_i$, and $s_{i,j+1}^{a,0}$ substituted for $c_{i+1}$. Processor (i, j+1) independently computes identical column assignments for all interactions in $S_{i,j}^{a,1}$. Processors (i+1,j) and (i+1, j+1) independently compute identical column assignments for interactions in $S_{i,j}^{1,1}$, and processors (i−1, j) and (i−1,j+1) independently compute identical column assignments for interactions in $S_{i,j}^{-1,1}$. At this point, all interactions have been uniquely assigned to a column. Interactions are then distributed between processors within each column using a procedure identical to that described previously for the one-dimensional case.

One could formulate multi-dimensional midpoint-ensured methods that would require only the import volume of the basic midpoint method, at the cost of a more complex algorithm for assigning interactions to processors. The midpoint-ensured method described above generalizes in a straightforward manner to the case where R is greater than one or more of the box side lengths if one requires that an interaction between a set of particles always be computed either in the box containing their midpoint or in a neighboring box (i.e., a box that shares at least a corner with it). Other midpoint-ensured methods that remove this restriction can lead to further improvements in load balance.

3.2.5 Translational Invariance

The decomposition schemes we have described thus far are translationally invariant. That is, each homebox has the same spatial relationship with its associated interaction zones. Assignment rules allow the description of decompositions that are not necessarily translationally invariant.

As an example of an assignment rule that is not translationally invariant, consider an assignment rule where $i_{a \to b} = i_a$, the least significant bit of the binary representation of $j_{a \to b}$ is the least significant bit of $j_a$, and the other bits of $j_{a \to b}$ are identical to those of $j_b$. This decomposition is similar to that of the SH analog illustrated in FIG. 7, but the import region of homeboxes with an odd j coordinate is different from that of homeboxes with an even j coordinate.

Such non-translationally invariant assignment rules may enable better performance in tree-like networks than restriction to translationally invariant approached. In a tree-like network, communication between certain sets of neighboring homeboxes is less expensive or more preferable than communication between other sets of neighboring homeboxes. It is possible that translationally invariant schemes will give optimal performance in translationally invariant networks, including toroidal networks and networks with all-to-all interconnection schemes, while non-translationally-invariant schemes may be preferable when the network itself is not translationally invariant.

We now devote our attention primarily to translationally invariant decompositions, recognizing that many of the approaches can be applied directly or with some modification to non-translationally invariant decompositions.

A subset of translationally invariant schemes are separable in the sense that the logical x coordinate of the interaction homebox depends only on the logical x coordinates of the particles and similarly for they coordinate. Most of the schemes discussed in this paper are separable, again recognizing that many of the approaches can be applied directly or with some modification to the non-separable case as well.

3.3 Commutative Interactions

One of the assumptions (labeled D above) in the simplified problem that is presented above was that for any pair of particles a and b, we separately compute the influence of a on b and the influence of b on a. In many, if not most applications, these influences possess symmetry such that only one interaction needs to be computed. Even if the interactions are not commutative, the computations may require the same inputs, such as particle positions. We can take advantage of this to reduce communication requirements by computing both non-commutative interactions at the same homebox.

The convolution criterion is modified for commutative interactions to include not only the reception region but also a "transmission region." The transmission region of a method is the smallest volume of space that is guaranteed to contain all particles that are influenced by particles in the homebox. We need to ensure that the union of a homebox's reception region and transmission region includes its entire interaction neighborhood. The transmission region and reception region are closely related. One can determine the transmission region with a procedure similar to that used to determine the reception region, but with the roles of the "red" zone and "blue" zone reversed. The result is that the transmission region is simply the reception region reflected about the homebox. The union of the two regions includes the entire interaction neighborhood if and only if the reception region includes a "symmetric half" of the interaction neighborhood. That is, the two regions include the entire interaction neighborhood if for any point in the interaction neighborhood that does not fall within the reception region, the point obtained by reflecting it about the homebox falls within the reception region.

If assignment rules are being used to specify the decomposition method, one way to generalize an assignment rule to take advantage of interaction symmetry is to order the particle pairs before applying the assignment rule. That is, a new assignment rule can be defined as the original assignment rule applied to the result of a function that orders the two arguments in a canonical order. For example, the ordering could be such that the first particle in a pair has the minimal x-coordinate with ties broken by y. Some assignment rules (such as the rule for the eighth shell method described later in this paper) require no additional ordering to utilize the commutative nature of the interaction computations.

Figure 15:
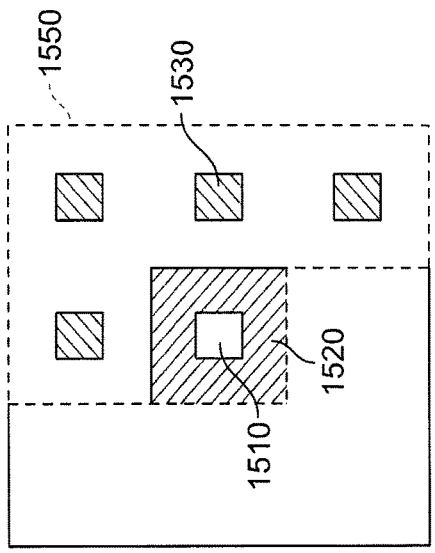
FIG. 15 is a view of regions in a two-dimensional decomposition for commutative interactions.
Figure 12:
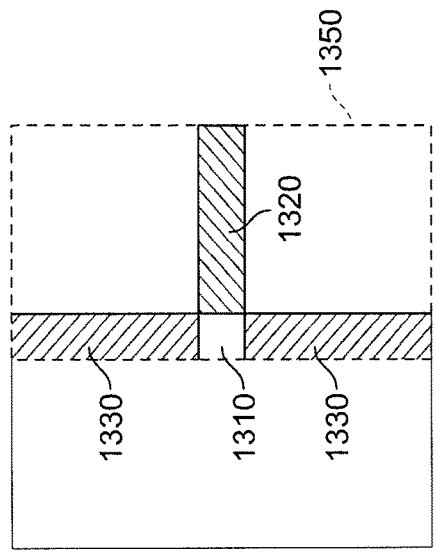
FIG. 12 is a view of regions in a simplified two-dimensional analog of the Half-Shell (HS) method for commutative interactions.

FIGS. 12 and 15 illustrate modifications that take advantage of commutative interactions for the import regions of HS and foam-like analogs of FIGS. 5 and 8, respectively. In each case, we have roughly cut one of the two interaction zones in half. The reception region for each scheme is enclosed within a dashed line, 1250 and 1550, respectively. In each case, the reception region includes at least half the interaction neighborhood and the union of the reception region and the reflection of the reception region about the homebox covers the entire interaction neighborhood. Note that in these decompositions, if we simply interact all particles in each zone with all particles in all other zones, then some near interactions will be computed and some excess interactions for pairs that are separated by a Euclidean distance greater than R might be computed. While pair level filtering mechanisms can be used, for example, by introducing a test in an inner loop of a computation iteration, an alternative method that avoids such double-counting without necessarily requiring such a test is introduced below in Section 6.

3.4 The Rounding Criterion

As introduced above, the approaches above relate to computation of interactions between particles that are separated by a Euclidean distance less than R, the interaction radius. In the simplified two-dimensional problem, each particle therefore interacts with particles falling within a circle of radius R rather than a square of side length 2R, as set out in assumption B above. Likewise, the interaction neighborhood of a homebox is a subregion of the square region considered above (as a consequence of assumption B) with the corners of the subregion being "rounded" rather than extending to the limits of the homeboxes that fall at least in part within the interaction neighborhood. Use of such an interaction neighborhood that reduces in volume through this rounding is taken advantage of to reduce the size of the import region and thereby reduce the amount of communication needed to import information for the particles to be interacted. This technique to reduce the size of the import region is referred to as "rounding."

The criterion that specifies the degree to which the boundaries of the import region can be rounded can be expressed as follows: a point in an interaction zone v may be discarded from a zone if it is further than R away from the closest point in the set of zones with which v interacts. For the two-zone methods considered in this section, this means that points in the red zone may be discarded if they are further than R away from all points in the blue zone, and points in the blue zone may be discarded if they are further than R away from all points in the red zone.

Figure 13:
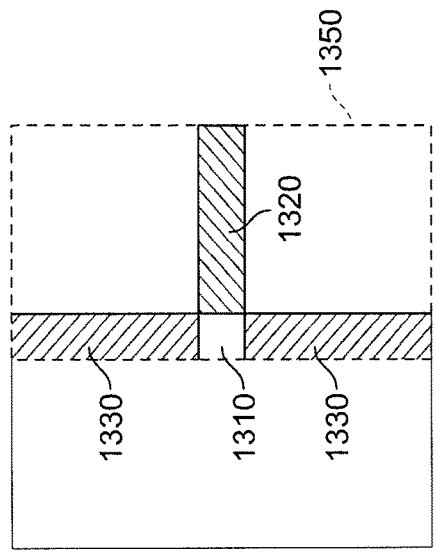
FIG. 13 is a view of regions in a simplified two-dimensional analog of the Neutral Territory (NT) method for commutative interactions.
Figure 14:
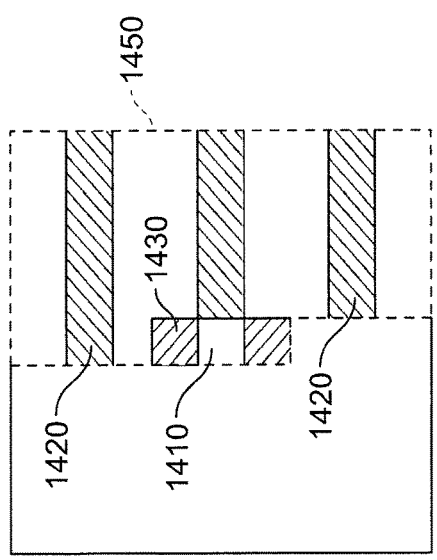
FIG. 14 is a view of regions in a two-dimensional decomposition that shares some characteristics with the Snir's Hybrid (SH) method for commutative interactions.
Figure 16:
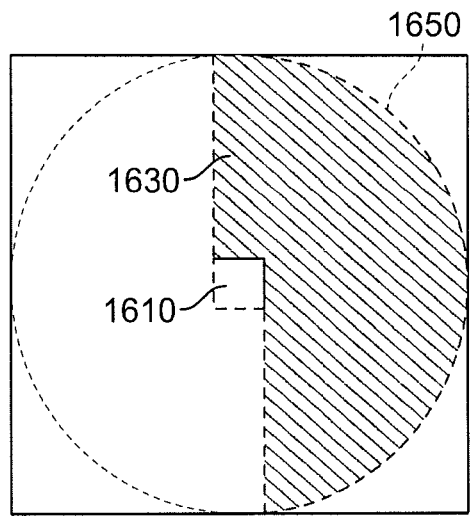
FIG. 16 is a view of regions in a simplified two-dimensional analog of the Half-Shell (HS) method for commutative interactions with rounding.
Figure 17:
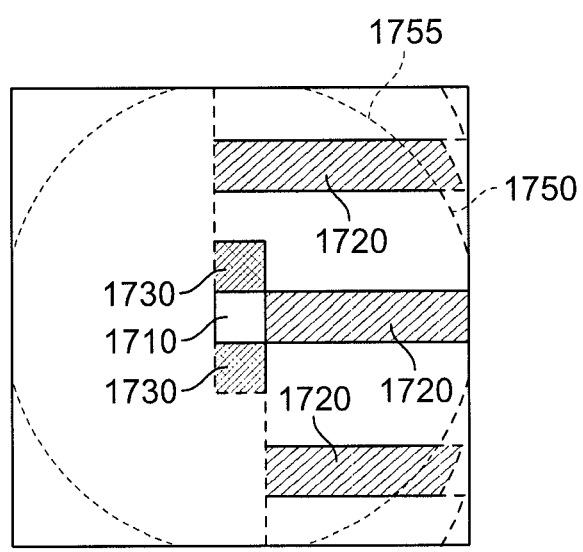
FIG. 17 is a view of regions in a two-dimensional decomposition that shares some characteristics with the Snir's Hybrid (SH) method for commutative interactions with rounding.

In FIGS. 16-17, rounded versions of the HS and SH analogs, respectively, show reduced import regions determined according to the rounding criterion presented above as compared to corresponding FIGS. 12 and 14, which do not employ rounding. In FIGS. 16-17, the interactions regions 1650 and 1750, respectively, are enclosed by the dashed line. Note that in FIG. 17, the rounded reception region 1750 expends beyond the interaction neighborhood 1755, which is enclosed by the dotted line. While rounding never increases import volume, it does not always reduce it. For example, the import regions of the particular instances of the foam-like analog in FIG. 15 or the NT analog in FIG. 13 are not reduced in volume by rounding.

The rounding criterion also allows us to generalize the techniques of the previous section to arbitrary R (for example that are not an integral multiple of the side dimension of a homebox) and is applicable to arbitrary home box aspect ratios. In such cases, the interaction zones may contain fractional homeboxes.

In a voxelized method the interaction zone consists of complete homeboxes (assumption C above), without making use of rounding, all local particles are tested for near interactions against the set of particles in that method's reception and transmission regions. When a method is rounded such that zones contain fractional homeboxes, assuming that entire homeboxes in the interaction neighborhood are imported, this is no longer true. For example, a local particle near the corner of a homebox may be tested for a near interaction against a different set of particles than a local particle in the opposite corner. The importing itself is preferably limited to the rounded regions, such that a homebox in the import region provides only particles located in a rounded subregion to the homebox performing the computation. In this way, fewer pairs of particles that are separated by more than R are considered by the homebox performing the computation, and for some pairs of zones being interacted, no test in the computation loop is required to avoid considering pairs of particles separated by more than R.

3.5 Decompositions in Higher Dimensions

The simplified techniques described above generalize to the higher dimensional cases (relaxing of assumption A above). Given a method where each homebox interacts particles in one translationally invariant interaction zone with particles in another zone, we can use the convolution criterion or an assignment rule to determine whether all particle pairs within a distance R will be interacted and then round the interactions zones with the rounding criterion. The three-dimensional HS, SH, NT and SNT methods described above are specific instances of this general class of schemes.

A class of decompositions that we have found useful in practice uses translationally invariant separable decompositions. Recall that a decomposition is termed "separable" if the logical x coordinate of the interaction homebox depends only on the logical x coordinates of the particles and similarly for the coordinates in other dimensions. A separable decomposition can be described by specifying a separate decomposition for each dimension. As one example of such a separable decomposition, one can use either of two decompositions for each dimension:

A. A decomposition where one zone contains only a single homebox, while the other contains a row of homeboxes spanning the interaction neighborhood. This is the case for both dimensions of the HS analog illustrated in FIG. 12 and of the NT analog illustrated in FIG. 13, and for the horizontal dimension of the SH analog illustrated in FIG. 14.

B. A decomposition where one zone consists of several contiguous homeboxes, while the other consists of a set of non-contiguous individual homeboxes spaced regularly across the interaction neighborhood. This is the case for both dimensions of "foam" analog illustrated in FIG. 15, and for the vertical dimension of the SH analog illustrated in FIG. 14.

Decomposition A above can be viewed as a special case of the decomposition B, but in terms of the properties of the resulting methods, it is worthwhile to treat them separately.

We can construct one zone of such a method by selecting one of the following four choices for each dimension:

a. All homeboxes a'. A single homebox b. A set of individual homeboxes spaced regularly across the dimension b'. A block of multiple contiguous homeboxes The other zone will then be uniquely determined by the requirement that it be complementary to the first zone. In each dimension, a and a' are complementary, as are b and b'.

In three dimensions, there are 20 unique decompositions that fit this description, assuming we take advantage of interaction commutativity by halving one of the interaction zones along one dimension.

Without loss of generality, we require that the "red" zone be halved along the first dimension. This restricts the options for the first dimension of the red zone to a and b. We can select any of the four choices for the second and third dimensions of the red zone. Because there is no distinction between these two dimensions, however, we impose an ordering a>a'>b>b' on the choices and require that the choice for the second zone be no larger than the choice for the third zone. Thus we can select the decompositions for the second and third zones in 4+3+2+1=10 ways, so there are a total of 2×10=20 decompositions in this class. Note that we have ignored details such as the exact positioning of each zone relative to the home box when counting unique decompositions.

Figure 18:
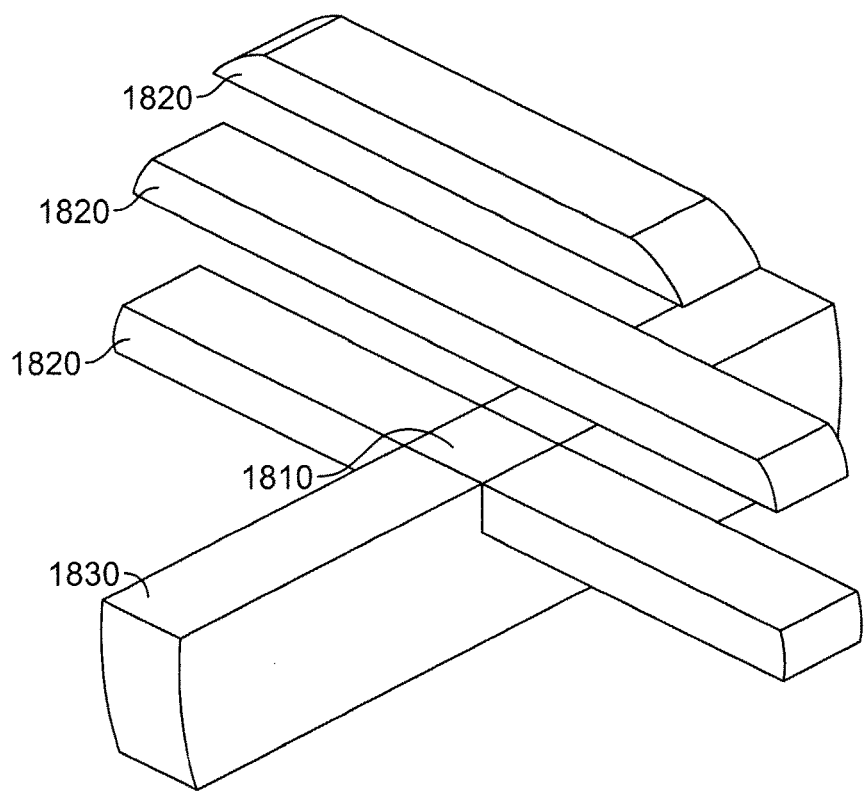
FIG. 18 is a perspective view of regions for the (SNT) method with rounding.
Figure 19:
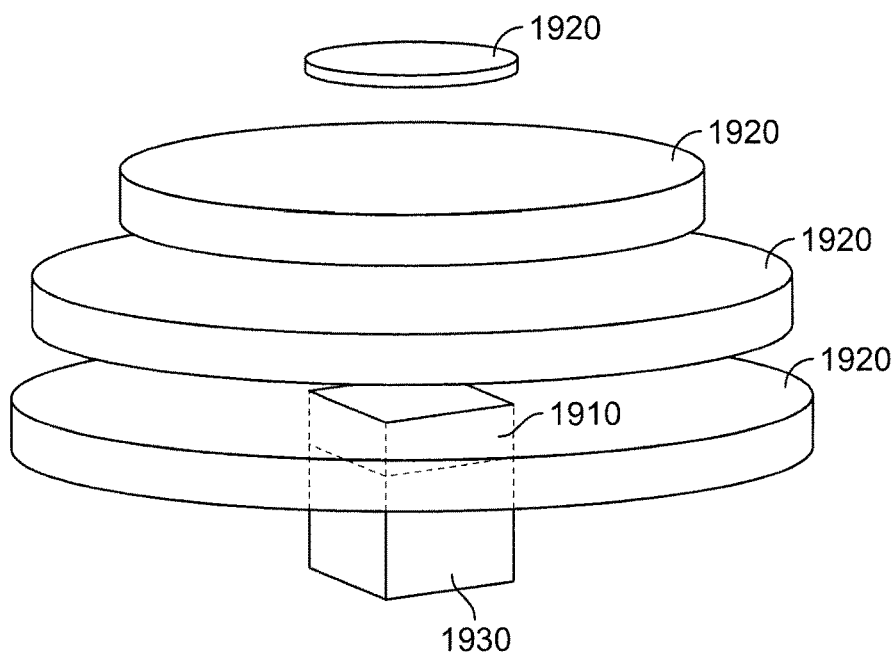
FIG. 19 is a perspective view of regions for the "clouds" method.
Figure 20:
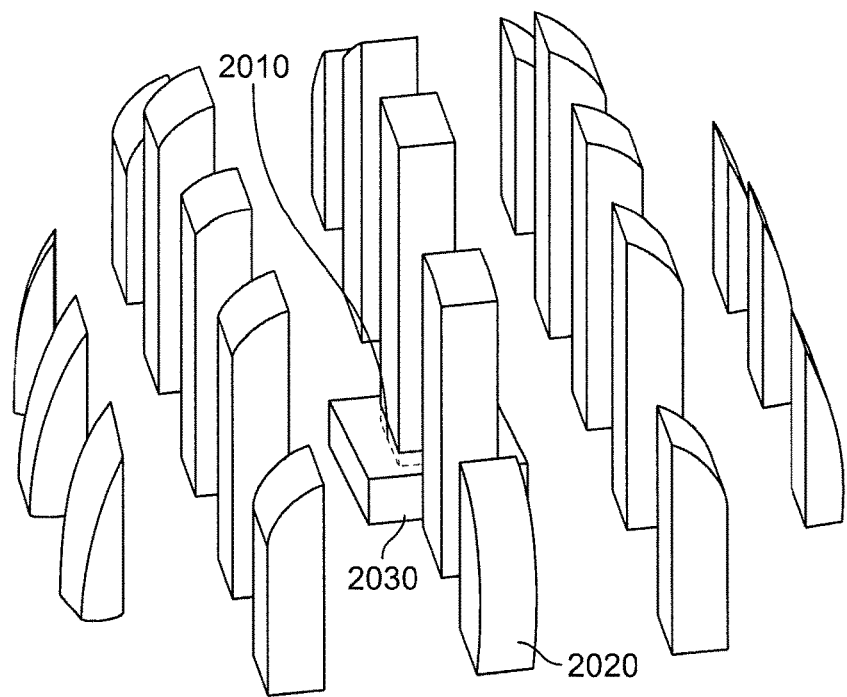
FIG. 20 is a perspective view of regions for the "city" method.
Figure 21:
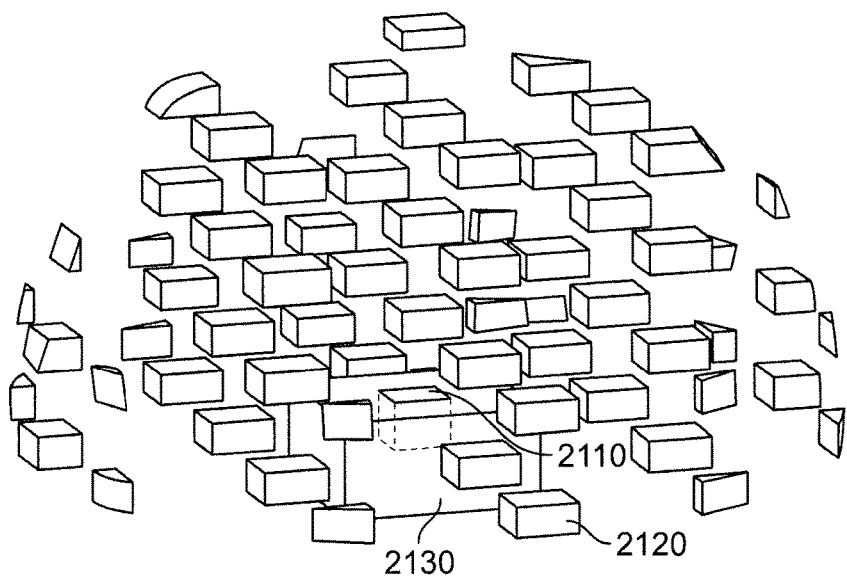
FIG. 21 is a perspective view of regions for the "foam" method.

The HS and NT methods, which are illustrated in FIGS. 2 and 3, respectively, are two of these unique decompositions. The SNT is another; as illustrated in FIG. 18 in which zones 1820 and 1830 of the homebox 1810 are rounded. FIGS. 19-21 show three further methods in this class. Referring to FIG. 20, a "clouds" method has one zone 1920 of the homebox 1910 that consists to a series of circular plates of successively smaller radius resulting from the rounding criterion and a second zone 1930 that is continuous with the homebox. Referring to FIG. 20, a "city" method has one zone 2020 of a homebox 2010 (hidden from view) that consists of a set of vertical towers that are truncated according the rounding criterion and a second zone 2030 that is continuous with the homebox 2010. Referring to FIG. 21, a "foam." method has one zone 2120 that consist of a set of subzones that are regularly arranged in a three-dimensional grid and truncated according to the rounding criterion, and a second zone 2130 that is continuous with the homebox 2110.

Rounding can be taken advantage of to different extents with the methods illustrated in FIGS. 18-21. The NT and SNT methods illustrated in FIGS. 3 and 18, respectively take advantage of two-dimensional rounding. That is, they round one or both interaction zones in order to eliminate parts of the zone that lie more than a distance R from the homebox when projected onto the plane. Such rounding guarantees that each particle will be tested against all particles in a surrounding region approximately shaped as a cylinder of radius R and height 2R. When homeboxes are very small relative to R, for example in the high parallelization limit, two-dimensional rounding reduces the size of the rounded zone and of the reception region by a factor of $\pi/4$ compared to the unrounded case. Other decompositions, including the HS, clouds, city and foam methods, illustrated in FIGS. 2 and 19-21, respectively, allow three-dimensional rounding. That is, they allow one to reduce one of the interaction zones in order to eliminate most parts of the reception region lying more than a distance R from the homebox in three-dimensional space. Such rounding guarantees that each particle will interact with all particles in a region shaped approximately as a sphere of radius R surrounding it, rather than some larger region. The size of the rounded zone and of the reception region can be reduced by a factor of $\pi/6$ compared to the unrounded case and by a factor of $2/3$ compared to the two-dimensional rounded case. Three dimensional rounding of a zone is possible when it uses decompositions a or b in all three dimensions.

As discussed below, it is desirable to balance the volume of the import zones in order to minimize import bandwidth requirements. This is more easily accomplished in systems with an even number of dimensions, where we can select two interaction zones with the same shape (e.g., FIG. 6). Even in this case, we typically halve one zone along one dimension due to symmetry considerations which introduces a difference in volume between the zones which could be balanced via other means. An odd number of dimensions introduces an inherent asymmetry between the two zones. We can still balance their volumes, for example, in one of two ways:

Use non-cubical homeboxes, making one of the zones larger than it would have been otherwise and the other smaller. This is the technique employed by the NT method.

In methods where one or both zones involve multiple non-contiguous pieces (e.g., decomposition b above), choose the spacing between the pieces appropriately. This is the technique employed by the SH method.

These optimization strategies can be combined. We return to the topic of optimization later.

4 Shared Communication

The midpoint method described above is particularly well-suited for parallelization of molecular dynamics simulations because it allows several different components of the computation to utilize the same communicated particle data, thereby reducing total communication requirements more than it would if each component were parallelized separately. It can be used to parallelize the evaluation of bonded force terms, which commonly involve the interaction of up to four particles, as well as pairwise electrostatic and van der Waals terms. Moreover, it allows several components of the MD computation, including the evaluation of the bonded force terms, to rely on the same data that is communicated for the evaluation of electrostatic and van der Waals forces between pairs of nearby atoms.

The total force on a particle in most biomolecular force fields can be expressed as a sum of bonded force terms, which depend on the covalent bond structure of the molecules, and non-bonded force terms, which comprise electrostatic and van der Waals interactions between all pairs of particles in the system. Bonded force terms include bond length terms, involving two particles connected by a bond; bond angle terms, involving three particles, two of which are bonded to a third; and dihedral angle terms, involving four particles connected by three bonds. We denote by $r_1$ the maximum radius of a sphere required to enclose the particles involved in any bonded term. In common biomolecular force fields, $r_1$ is no larger than 4 Å.

The non-bonded force terms, on the other hand, involve all pairs of particles in the system and therefore represent a much larger computational burden. Van der Waals forces fall off sufficiently quickly with distance that they can typically be neglected for pairs of particles separated by more than some cutoff radius $r_2$, typically chosen between 9 and 12 Å. An ever-mounting body of evidence shows that neglecting electrostatic interactions beyond a cutoff is inadequate for explicit solvent simulations, so electrostatic forces are typically computed by one of several efficient, approximate methods that take long-range interactions into account without requiring the explicit interaction of all pairs of particles. Examples of these methods include mesh-based Ewald methods such as Particle-Particle Particle Mesh (PPPM), Particle Mesh Ewald (PME), Lattice Gaussian Multigrid (LGM), and Gaussian Split Ewald (GSE), which use the Fast Fourier Transform (FFT) or a multigrid solver to compute electrostatic potential on a mesh given a charge distribution on that mesh. These methods require that modified electrostatic interactions be computed explicitly within some cutoff radius; we will assume that this cutoff radius is chosen to be identical to the van der Waals cutoff radius $r_2$, as is typically the case. These methods also require that charge be mapped from particles to nearby mesh points before the Fourier-domain or multigrid computation, and that forces on particles are computed from potentials at nearby mesh points afterwards. In the charge spreading computation, the charge on each mesh point is determined as a sum over nearby particles, while in the force spreading computation, the force on each particle is computed as a sum over nearby mesh points. We denote by $r_3$ the maximum distance between any particle and a mesh point that "interacts" with it in either charge spreading or force spreading. The value of $r_3$ depends on the parameters of the long-range electrostatics method employed, but is typically around 5 Å.

When one parallelizes the computation of explicit pairwise electrostatic and van der Waals interactions using the midpoint method, each processor must import data for particles lying within a distance of $r_2/2$ from the boundary of its home box. Each processor computes interactions that exert force on the particles in its import region, so once it has completed computation of pairwise interactions, it must export a force for each of these particles to the respective particle's home box.

If $r_3 < r_2/2$, then no additional communication is required to support charge spreading and force spreading. The import requirements of the explicit nonbonded force computation ensure that each processor will import all remote particles within a distance $r_2/2$ of any mesh point lying in the home box. Likewise, the export requirements ensure that each processor will export forces to this set of remote particles (a remote particle is a particle that does not reside on the interaction box). The force contribution on each remote particle due to mesh points in the home box can be combined into each of these forces before inter-chip communication. In MD runs using common biomolecular force fields, $r_3$ is usually approximately equal to $r_2/2$. Parameters of the mesh-based Ewald method employed can be tuned to guarantee that $r_3 < r_2/2$; alternatively, the import region can be expanded to include all particles within a distance $r_3$ of the home box boundary.

Likewise, if $r_1 < r_2/2$—as is typically the case for MD simulations using common biomolecular force fields—then no additional communication is required to support computation of the bonded terms. This computation can also be parallelized using the midpoint method, which specifies that each bonded term be computed by the processor that contains the midpoint of the particles involved in that term. The import requirements of the explicit nonbonded force computation ensure that data for each particle will be available on any processor that needs it to compute a bonded force term, while the export requirements ensure that that a force contribution will be exported back to the processor on which that particle resides.

In an MD simulation parallelized via a spatial decomposition, particles migrate from one home box to another as they move. As long as the maximum distance $r_4$ that a particle moves in a time step—typically under 0.1 Å—is less than $r_2/2$, no extra communication will be required to migrate the particles; their new positions will be communicated as part of the import data required by the midpoint method for explicit non-bonded interactions (in certain cases data will need to be imported from more boxes than if particle migration had been performed separately, because the data to be imported might reside on any box including points within a distance $r_2/2+r_4$ of the interaction box, rather than only on boxes including points within a distance $r_2/2$ of the interaction box). Note that this is not generally the case for the NT, HS, or ES methods, in which proximity of a particle to an interaction box does not guarantee that the particle will be imported by that interaction box.

Consider a molecular dynamics simulation with a cubic global cell measuring 64 Å on a side, running on a system with 512 processors and partitioned into an 8×8×8 mesh of boxes. Suppose that we use an interaction radius of $r_2=12$ Å for explicit pairwise non-bonded interactions. If we use the midpoint method to parallelize these interactions, the import volume will be 5923 Å$^3$; no additional communication is required for charge spreading, force spreading, particle migration, or bonded force computation, provided that bonded force computation is also parallelized using a midpoint method. Using the HS method to parallelize the explicit pairwise non-bonded interactions, on the other hand requires an import volume of 11352 Å$^3$. This import volume does not ensure, however, that all remote particles near a mesh point on a particular home box are imported onto that home box. If $r_3$=4.5 Å, charge spreading will require an additional import volume of 2164 Å$^3$, and force spreading will require a comparable amount of additional data export. Traditional parallelization strategies for bonded forces, in which each term is computed either on a fixed processor or on the processor containing a specific particle, will require additional communication, as will particle migration.

We expect that all method with the import region of the midpoint method allow communication to be shared in the same manner. Also, while a mesh-based Ewald methods is presented above, the midpoint method also allows communication sharing between components of the computation for other long-range electrostatic methods. Essentially all of these methods (including the Fast Multipole Method and related tree code methods) require that some pairwise particle interactions between nearby particles be computed explicitly; at a minimum, the communication required for this computation can be shared with the communication required for bonded interactions.

5 Pair-Lists and Exclusion Groups

In approaches that involve identifying pairs of particles that are to be interacted, computation can be arranged such that the interaction computations are performed at the time that the pairs of particles are identified. As an alternative, approaches such as the NT approach are used to identify the pairs of particles to be interacted, but rather than performing the computations as the pairs are identified, a list of the pairs is generated. The list is then used to iterate through the required computations. For example, the pair list is completely calculated before any pairwise computations begin, or alternatively, a pipelined approach is used in which another software or hardware module receives the list and computes the interactions while more pairs are being computed. In some hardware architectures, separation of the generation of the pairlist from the pairwise computations may increase computation efficiency, for example, by allowing simpler hardware or a more efficiently coded inner software loop to be used to compute the pairwise interactions.

Another aspect of computation of pairwise particle interactions, whether using pairlists or performing the computations was appropriate pairs are identified, is that some particle pairs within the specified interaction radius must effectively be excluded from the computation. For example, in a molecular dynamics simulation, the computation of Van der Waals and near electrostatic interactions (non-bonded interactions) for all particles that are within a cutoff radius R and that are not covalently bonded is performed. If a pair of particles with the cutoff radius are covalently bonded, then a near electrostatic force term is not included. A pair of particles within radius R but that does not have a non-bonded interaction is termed an excluded pair.

Approaches to dealing with exclusion of computations involving bonded pairs of particles include (1) including the electrostatic force contributions for all pairs of particles within the interaction radius, and later subtracting out (i.e., "correcting") the force contributions for pairs that are covalently bonded, and (2) identifying the excluded pairs during the identification of pairs of particles with the interaction radius to avoid introducing the electrostatic force terms in the first place.

Neutral territory methods described above allow interactions between all pairs within R to be found and distributed efficiently, for example, on a parallel machine. However, in order to take into account exclusions efficiently during this computation, a means to quickly detect whether or not a pair of particles is excluded can increase the efficiency of the computation.

One solution is to create a Boolean matrix indexed by particle whose entries indicate whether or not a pair is excluded—conceptually, is excluded(i,j). However, even for a modest number of particles, direct storage of this matrix (or half the matrix as the matrix is transpose symmetric) is likely prohibitive. Since the number of exclusions usually scales proportional to the number of particles, the matrix is sparse and could be stored in a compressed format.

Exclusion groups provide an alternative means for specifying a set of excluded pairs. Each particle has an associated value that indicates the exclusion group to which the particle is assigned. If two particles belong to the same exclusion group, they are considered an excluded pair and discarded during the matchmaking process of a neutral territory method.

This test is efficient and maps nicely onto both neutral territory method implementations and the physical properties of many problems involving range limited pairwise interactions. For example, in molecular dynamics again, all the non-bonded interactions between particles belonging to the same water molecule are commonly excluded for example. If there is an exclusion group that corresponds to each water molecule then, no additional handling of water exclusions is necessary.

To demonstrate their usage and assignment, consider a simulation with 12 particles. These 12 particles represent a methane molecule (particles 0,1,3,6,9), two water molecules (particles 2,4,5 and 7,8,10) and a sodium ion (particle 11). All pairwise non-bonded interactions between particles that belong to the same molecule are excluded.

Particles 0,1,3,6 and 9 could be assigned to exclusion group 2, particles 2, 4 and 5 could be assigned to exclusion group 5, particles 7,8,10 could be assigned to exclusion group 0 and particle 11 could be assigned to exclusion group 1. This demonstration also shows that particles and exclusion group assignments have no special ordering requirements.

6 Multiple Zone Methods

In general, in the methods considered above, two overlapping zones are interacted—the homebox/shell, tower/plate, base/comb, brick/foam or, generically, blue/red. In this section, we consider methods involving multiple zones, any pair of which may be selected to interact depending on the particular method being used. In such a multiple zone method, the import region and homebox are treated as the union of a set of several potentially overlapping zones. Particles in a zone are interacted with all particles in a subset of the other zones.

Figure 22:
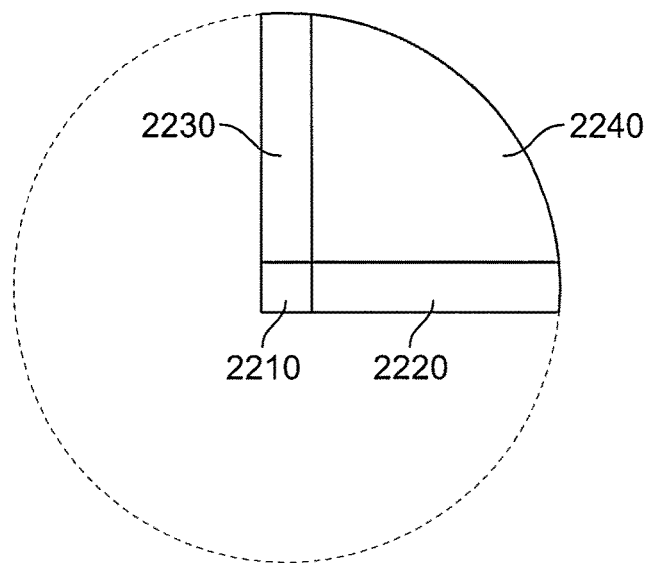
FIG. 22 is a view of regions of a two-dimensional multiple zone method.

To demonstrate a multiple zone method for a simple two-dimensional case, consider the import region shown in FIG. 22. The homebox 2210 imports a rectangle 2220 adjacent to the homebox extending R in +x direction, a rectangle 2230 adjacent to the homebox 2210 extending R in the +y direction and a quarter of a circle 2240 of radius R adjacent to both rectangles 2220 and 2230. The homebox 2210 is treated as a distinct zone. Homebox 2210 particles are interacted with the particles in the each of the other three zones (2220, 2230, and 2240), and particles in the vertical rectangle 2230 are interacted with particles in the horizontal rectangle 2220. Completing the specification, pairs of particles are filtered by interaction radius R and local interactions (which occur exclusively in the homebox-homebox zone interaction) are to be filtered to avoid double counting.

Note that the filtering operation can be implemented in a number of ways. If the homeboxes are smaller than an excluded volume about the particles such that there is at most only one particle per homebox, then there will be no local interactions to consider at all. If there are many local interactions, they could be filtered by particle ID or other means. Alternatively, they could be handled by a special case loop construct. If it is desirable to treat the homebox like any other zone and the number of particles per homebox is modest, a fix-up loop could be done to subtract off redundant interactions. Still another possibility for certain kinds of near interactions is to treat homebox-homebox zone interactions like regular zone-zone interactions but scale the results by half.

The import volume of this method is always less than that of the HS analog, which is illustrated in FIG. 16. When R is small relative to the home box side length, the import volume is also less than that of the NT analog, which is illustrated in FIG. 13.

The validity of a multiple zone method can be checked by either determining an assignment rule or by applying the convolution criterion. The convolution criterion can be generalized to multiple zones using geometric considerations as follows. Each zone-zone interaction generates a reception and transmission region. The union of all the zone-zone reception and transmission regions must cover the interaction neighborhood of the homebox.

This method illustrated in FIG. 22 corresponds to the following assignment rule:

$$(i_{a \leftrightarrow b}, j_{a \leftrightarrow b}) = (\min(i_a, i_b), \min(j_a, j_b))$$

Alternatively, the convolution criterion can be applied. The reception and transmission regions of the interaction between the homebox 2210 and the other zones 2220, 2230 and 2240 cover all but two quarter circle portions of the interaction neighborhood. The interaction of the rectangular zones 2220 and 2230 covers the remainder.

Note that for any particular multiple zone method, the set of combinations (pairs) of zones for which particle interactions are considered is selected, for instance, to avoid double counting. The order or schedule in which to consider combinations of zones can also be specified, for example, selected according to computations or communication considerations. The order of considering combinations of zones is not important to insure that all near interactions are computed, as long as all the selected combinations are considered. However, the schedule can be selected to overlap communications with computation.

For commutative interactions, the specification of a schedule can be thought of as an upper triangular matrix whose size is the number of zones in the method. The entries in this matrix are non-negative integers giving the order in which the zone-zone interactions are computed. A zero entry indicates that the zone-zone interaction is not computed at all.

Figure 23:
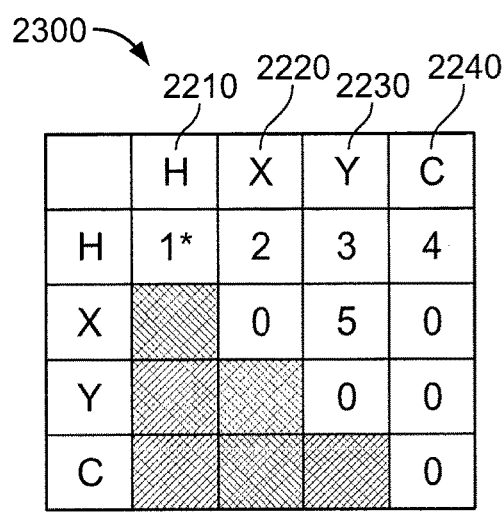
FIG. 23 is a computation schedule for the regions illustrated in FIG. 22.

A schedule for the method in FIG. 22 is shown in FIG. 23. A multiple zone method is specified according to the definitions of the zones, the zone interaction schedule, and any additional redundancy filtering mechanisms.

An optimal schedule is influenced by characteristics of the network and processor on which the method is implemented. As one approach to determining schedules, and the approach generally used in this description involves filling the schedule matrix by row and then by column. This order allows the maximum number of zone-zone interactions to be performed with zones already received as the computation progresses. Having selected an order for the rows and columns of the matrix, a remaining degree of freedom is the ordering of the zones. While a selection of an optimal order may in general be hardware dependent, in the schedules shown in FIG. 23 import zones that participate in more zone-zone interactions are scheduled before those that participate in fewer zone-zone interactions.

The order of interactions that allows maximal overlap of computation and communication depends on details of the available computational hardware. A procedure for determining a schedule is as follows. First, we determine the order in which the zones will be imported, requiring that zone u be imported before zone v if zone u participates in more zone-zone interactions than zone v. We then number the zones according to the order in which they are imported, with zone 1 representing the interaction box, zone 2 representing the first zone imported, zone 3 representing the second zone imported, and so on. We set schedule entries corresponding to pairs of zones that should not be interacted to zero. We then number the remaining entries in column-major order; that is, the interaction in row $i_1$ and column $j_1$ will be computed before the interaction in row $i_2$ and column $j_2$ if $j_1 < j_2$, or if $j_1 = j_2$ and $i_1 < i_2$. This ensures that computation of the interactions between a pair of zones that have already been imported never has to wait for the computation of an interaction involving a zone that has not yet been imported.

Multiple zone methods can have a number of practical benefits. First, they can reduce bandwidth requirements relative to previously known methods. Increasing the number of zones allows more near interactions to be computed for a given import volume, because interactions are computed between zones rather than within a zone. Increasing the number of zones allows more potential pairs to be considered for a given import volume because a given particle could be tested against particles from more than two zones. An additional effect is that multiple zone methods can expose additional rounding opportunities.

Second, multiple zone methods can be used to simplify or even eliminate many of the filtering criteria required to avoid redundant computations and/or double counting. For example, in the two-zone NT method, which is illustrated in FIG. 3, without redundancy filtering, interactions between particles whose x and y base coordinates are the same (i.e., are in the tower consisting of the home box 310 and zone 320) are computed twice. However, the NT method can be reformulated as a multiple zone method in a manner that eliminates the need for this testing. This reformulation is given below.

Third, using more zones allows more opportunities to concurrently perform communication for later-scheduled zone combinations while performing earlier zone combinations, thereby "hiding" communication delays with computation. For example, zones could be assigned in the schedule based on latency to import data from that processor. The order in which zone-zone interactions are performed would then allow some interactions to be performed earlier while more remote zones are imported.

Figure 24:
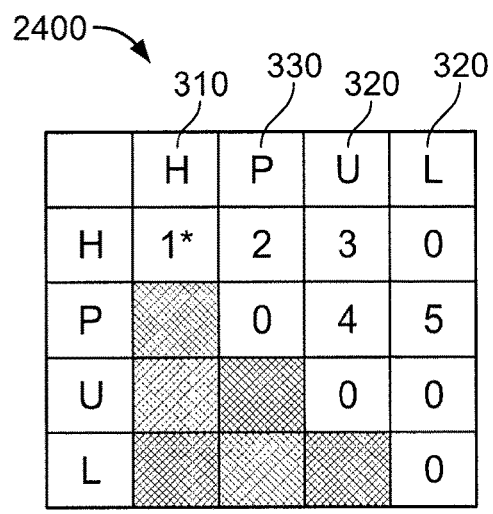
FIG. 24 is a computation schedule for a multiple zone version of the decomposition shown in FIG. 3.
Figures 27, 28:
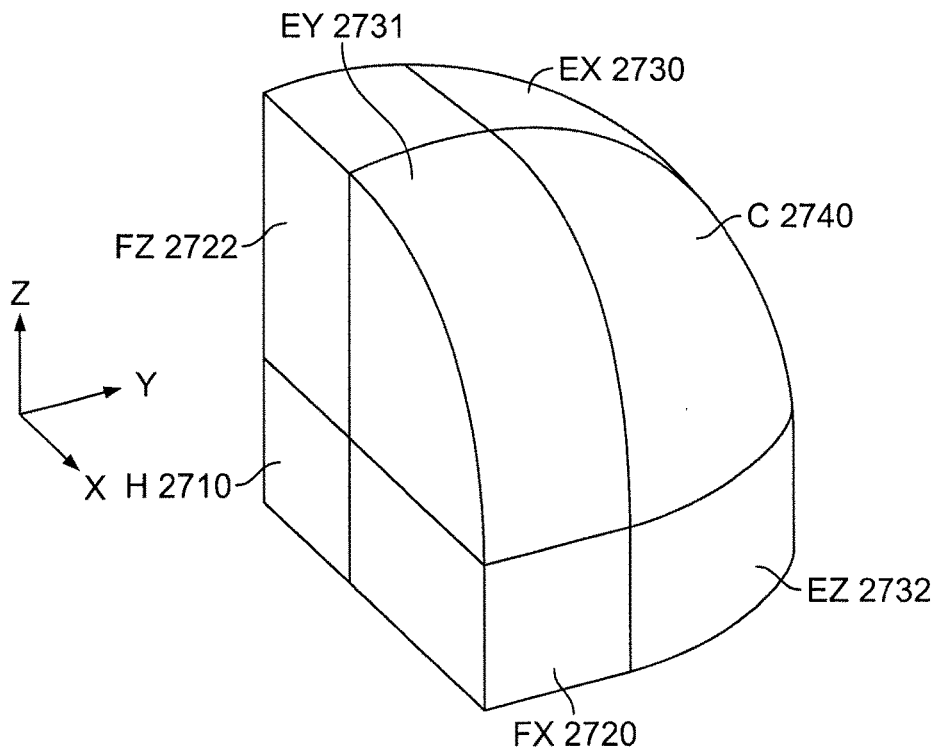
FIG. 27 is a perspective view of regions for the "eighth shell (ES)" method.
FIG. 28 is a computation schedule for the decomposition shown in FIG. 27.

To demonstrate these advantages on a three-dimensional method, consider the original NT method reformulated using four zones. The zones are denoted the homebox (H) 310, the lower tower (L), which forms a portion of zone 320, the upper tower (U), which forms another portion of zone 320, and the outer plate (P) 330. The zone interaction schedule is shown in FIG. 24. The schedule eliminates the homebox-tower interaction redundancies; in particular, the homebox is not interacted with the lower tower. Consequently, the rounding criterion applied to the lower tower indicates that the corner furthest from the outer plate can be trimmed, reducing communication bandwidth Note that the lower tower is trimmed by the intersection of two perpendicular cylinders of radius R; the impact on bandwidth is small for large R but significant for small R.

Additionally, interaction filtering is simplified as there is no longer a need to filter interactions between the particles in homebox and particles in the lower tower. Referring to FIG. 25, an algorithm for implementing communication and communication corresponding to the schedule in FIG. 24 gives a communication sequence based on the schedule appropriate for MPI-style cooperative message passing systems for a force computation. The algorithm has partially overlapped both particle import and force export. At the beginning of computation cycle (one time step of the simulation), the data characterizing the particles are sent from the homebox to other homeboxes that will need that data for computations at those homeboxes (step 2501). The other homeboxes similarly begin sending their data and the homebox begins receiving data for zones P, U, and L (step 2502). As the other homeboxes compute forces on particles in the homebox, they start sending the computed forces to the homebox, which begins receiving them (step 2503). The homebox already has all the data for particles in the homebox, so it can perform the homebox-homebox interactions without waiting for the completion of any of the communication that is in progress (step 2504). After the homebox ends the step of receiving data for particles in the plate (P) that was initiated in step 2502 (step 2505), the homebox computes the homebox-plate (H-P) interactions (step 2506). After the homebox ends the step of receiving data for particles in the upper tower (U) that was initiated in step 2502 (step 2507), the homebox computes the homebox-upper tower (H-U) interactions (step 2508) and computes the plate-upper tower (P-U) interactions (step 2509). At this point, the homebox begins sending the computed forces for particles in the upper tower (U) to their respective homeboxes (step 2510). After the homebox ends the step of receiving data for particles in the lower tower (L) that was initiated in step 2502 (step 2511), the homebox computes the plate-lower tower (P-L) interactions (step 2512). At this point, the homebox begins sending the computed forces for particles in the plate and lower tower to their respective homeboxes (step 2513). Finally, the homebox finishes receiving the forces computed for its particles form other homeboxes (step 2514).

Another way a multiple-zone schedule approach can be used is to break up each of the types of interaction zones described above into a collection of uniform voxels. The voxels can have the same shape as the homeboxes, but this is not necessary. The schedule is then specified according to which pairs of voxels are to be interacted, achieving the same result as a schedule define on the larger interaction zones, with an added advantage that better rounding can be achieved by only scheduling pairs of voxels for which some pairs of particles may be within the interaction radius.

6.1 A Lower Bound for Import Volume

A lower bound on the import volume ($V_{import}$) of a multiple zone method can be established by considering the number of pairwise interactions that need to be computed. This bound takes the form:

$$V_{import} \geq \frac{V_h}{\left(1 - \frac{1}{N_{zr}}\right)} \left[ \sqrt{\left(1 - \frac{1}{N_{zr}}\right) \frac{V_{ir,remote}}{V_h} + 1} - 1 \right] \text{ for } N_{zr} > 1$$

-continued $$V_{import} \geq \left(\frac{1}{2}\right) V_{ir,remote} \text{ for } N_{zr} = 1$$

Above, $N_{zr}$ is the number of zones that import remote particles, and $V_h$ is the volume of a homebox. $V_{ir,remote}$ is the expected volume of the portion of the interaction region that resides on other processors for a randomly selected particle. $V_{ir,remote}$ depends on R, $V_h$, and the homebox aspect ratio. The lower bound decreases as the number of zones increases, as $V_h$ increases, or as R decreases.

The bound for the import volume of a method is met when the remote import zones are balanced in volume, the interaction schedule is dense in the sense that every zone interacts with every other zone, and the method is efficient in the sense that every pair considered is a non-redundant remote interaction. Geometrically, this is often not feasible, particularly when the interaction radius is small compared to homebox dimension. One can approximate finite homebox size effects by replacing $V_{ir,remote}$ in the above bounds with the volume of the remote portion of a homebox interaction neighborhood. For spherical interaction regions, this volume ($V_{ir,remote,eff}$) can be expressed as $$\frac{V_{ir,remote,eff}}{V_h} = \frac{4\pi\alpha_R^3}{3} + \pi\alpha_R^2(\alpha_x + \alpha_y + \alpha_z) + 2\alpha_R(\alpha_x^{-1} + \alpha_y^{-1} + \alpha_z^{-1}).$$

Above, the normalized homebox aspect ratios $\alpha_x = h_x/V_h^{1/3}$, $\alpha_y = h_y/V_h^{1/3}$, $\alpha_z = h_z/V_h^{1/3}$ and the parallelization parameter $\alpha_R = R/V_h^{1/3}$ are used. This effective interaction region volume is exact in the limit of large $\alpha_R$ for any $N_{zr}$ and in the limit $N_{zr} = 1$ for any $\alpha_R$.

6.2 Optimization Priorities

By symmetry, the volume of the effective remote interaction region is minimized for cubic homeboxes ($\alpha_x = \alpha_y = \alpha_z = 1$). This gives a less tight approximate lower bound that is independent of homebox aspect ratio:

$$\frac{V_{import}}{V_h} \geq \left(1 - \frac{1}{N_{zr}}\right)^{-1} \left\{ \sqrt{\left(1 - \frac{1}{N_{zr}}\right)\left[\frac{4\pi\alpha_R^3}{3} + 3\pi\alpha_R^2 + 6\alpha_R\right] + 1} - 1 \right\}$$

This bound does not indicate that cubic homeboxes are optimal; it is simply a bound that is independent of homebox aspect ratio. There are three terms involving $\alpha_R$ in the bound. These terms geometrically originate from the 8 corners (the cubic term), the 12 edges (the quadratic term) and the 6 faces (the linear term) of the interaction neighborhood.

Referring to FIG. 26, the magnitude of the three terms is illustrated as a function of $\alpha_R$. The magnitudes of the three terms are normalized so that the magnitude of the corner term is 1.0. In the low parallelism limit, the face terms dominate the import volume, followed by edge terms and then corner terms. In this limit, a method should strive to minimize the volume of imports required to cover the faces of the interaction neighborhood followed by the import of edges. As the parallelization parameter increases though, these priorities change. The first transition point occurs at $\alpha_R > 2/\pi \sim 0.64$. After this transition, the priorities are ordered edge, face, corner. The next transition occurs at $\alpha_R > (9/(2\pi))^{1/2} \sim 1.20$; the priorities are then ordered edge, corner, face. The final transition occurs at $\alpha_R > 2.25$ when the priorities become ordered corner, edge, face.

These optimization priorities are approximate and meant to serve as guidelines in designing methods. Depending on the exact homebox aspect ratio and the details of the system running the methods, the exact transition points between various methods could be different.

7 Applications of Generalized Decompositions

In this section, specific instances of the generalized approach are presented. While most methods are not proven to be optimal in any particular sense, in many cases the methods are believed to be optimal or very close to optimal in terms of bandwidth for their intended regime. In most methods described, the only interaction filtering that needs to be applied is interaction radius and local interaction filtering. That is, filtering is not generally required to avoid considering pairs of particles more than one in the system, other than for pairs of particles that come from the same homebox.

7.1 Eighth Shell Method

The import region for a HS method consists of 4 corner, 6 edge and 3 face import sub-regions. A face subregion includes homeboxes that differ in one dimension, an edge subregion differs in two dimensions, and a corner subregion differs in all three dimensions. Intuitively, the half-shell method might seem to be the best that could be achieved in the low parallelism limit ($\alpha_R < 0.64$). This is not the case.

The eighth-shell (ES) method is the three-dimensional generalization of the two-dimensional method illustrated in FIG. 22. The ES method import region consists of 7 remote zones of the homebox H 2710: 3 face zones (+x import subregion denoted FX 2720, and similarly for y (FY is hidden in FIG. 22) and z, FZ 2722), 3 edge zones (+y+z import subregion denoted EX 2730, +x+z region denoted EY 2731, +x+y region denoted EZ 2732) and 1 corner zone (+x+y+z import subregion denoted C 2740). Referring to FIG. 23, an interaction schedule corresponds to the regions shown in FIG. 22. The eighth shell method is so named because asymptotically, its import region consists of one-eighth the full shell surrounding the homebox.

The ES import region is smaller than the HS import by 3 edges and 3 corners. The edge-face interactions (interactions 9, 11 and 13) cover the interactions that are handled in the HS method by the interaction of the homebox with the 3 removed corners. Likewise, the face-face interactions (interactions 4, 6 and 7) cover interactions that were handled by the interaction between the homebox and the 3 removed edges. Like its two-dimensional counterpart, the method can be described by an assignment rule $(i_{a \leftrightarrow b}, j_{a \leftrightarrow b}, k_{a \leftrightarrow b}) = (\min(i_a, i_b), \min(j_a, j_b), \min(k_a, k_b))$.

The total import volume is:

$$\frac{V_{import,es}}{V_h} = \frac{\pi \alpha_R^3}{6} + \frac{\pi \alpha_R^2}{4}(\alpha_x + \alpha_y + \alpha_z) + \alpha_R(\alpha_x^{-1} + \alpha_y^{-1} + \alpha_z^{-1})$$

Figure 29:
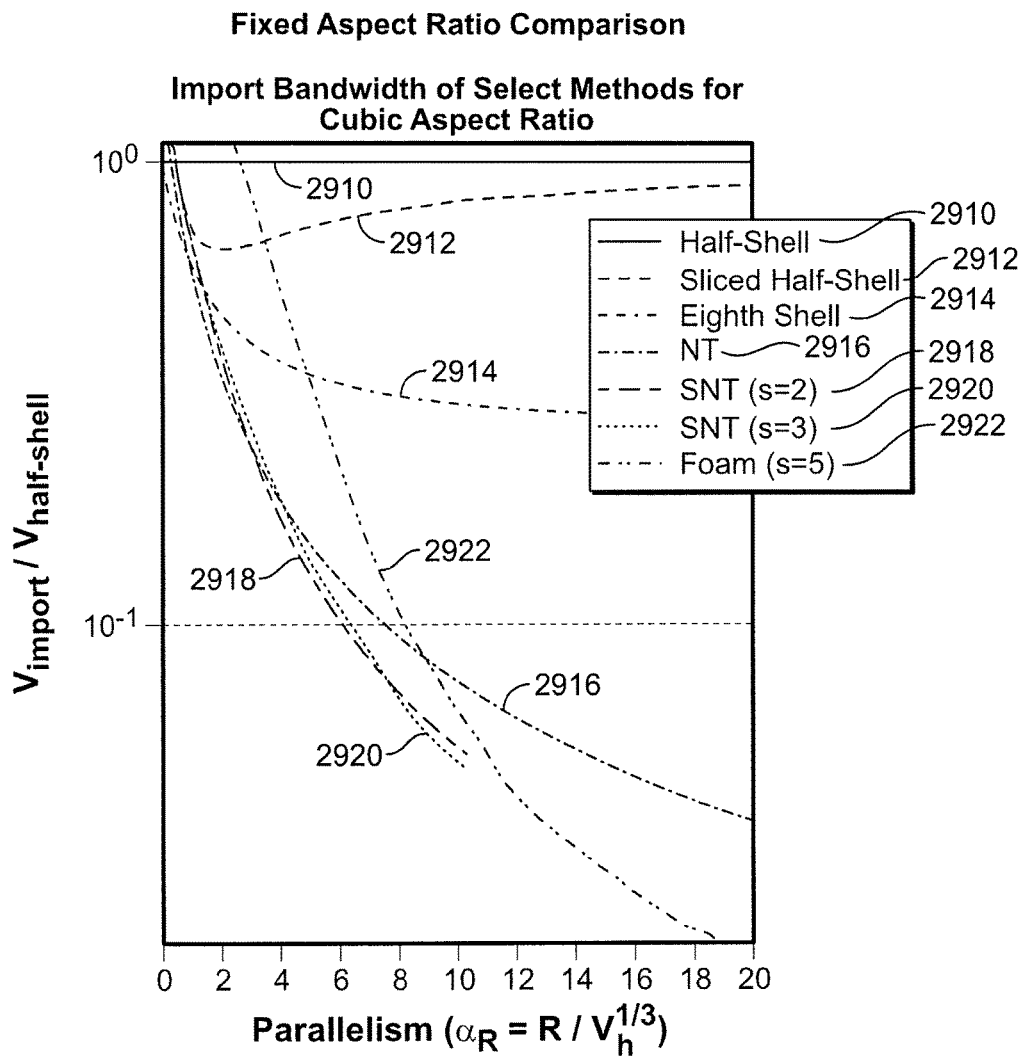
FIG. 29 is a graph of import volume versus degree of parallelism.

This method may be an optimal bandwidth method in the low parallelism limit. It is also highly symmetric which can have additional benefits on various network topologies. Referring to FIG. 29, the bandwidth of a number of methods is compared to the standard of the half-shell (HS) method 2910. The eighth-shell 2914 method is compared against several other methods and the approximate lower bound when using cubical homeboxes. The eighth-shell method conforms to the low parallelism optimization priorities of minimizing face, edge, and corner regions. The optimization priorities indicate the origin of the contributions to the import volume in terms of different geometric categories as a function of the degree of parallelism. For example, at a low degree of parallelism, face imports dominate the import region and therefore would be preferable to address as a priority for further optimization.

7.2 Sliced Half Shell Method

Figures 30, 31:
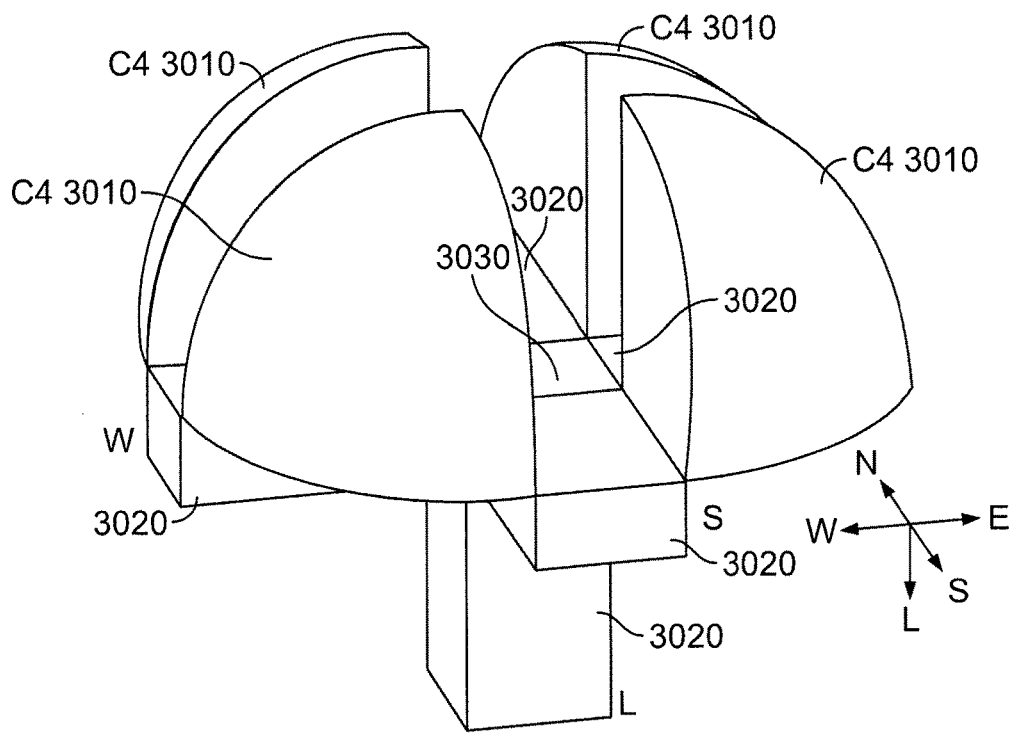
FIG. 30 is a perspective view of regions for a "sliced half-shell" method.
FIG. 31 is a computation schedule for the decomposition shown in FIG. 30.

A class of methods for the range $0.64 < \alpha_R < 1.20$ may be well matched to the optimization priorities. Referring to FIG. 30, a Sliced Half Shell (SHS) consists of 4 corner import subregions 3010 (denoted as a single zone C4) in a sliced hemisphere arrangement and 5 face imports 3020 (denoted as the 5 zones N, S, E, W, L). Note that the S and W face imports can be rounded further than the N and E face imports as they do not interact with the homebox 3030. A schedule corresponding to FIG. 30 is given in FIG. 31.

7.3 Multiple Zone NT and SNT Methods

Figures 32, 33:
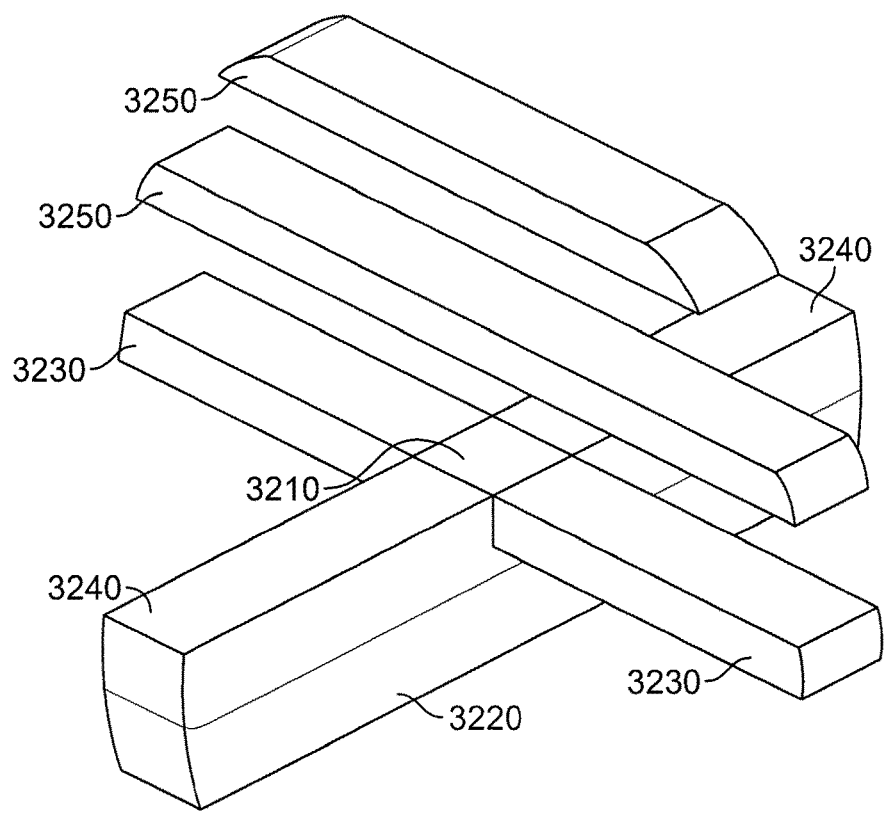
FIG. 32 is a perspective view of regions for the (SNT) method with rounding.
FIG. 33 is a computation schedule for the decomposition shown in FIG. 32.

The schedule for the multiple zone NT method presented above, and shown in FIG. 24. Referring to FIG. 32, a multiple zone of the two-zone SNT method illustrated in FIG. 18, consists of an extended base extended base 3220, which is below the homebox 3210. The comb 3230 and the portion 3240 of the base that are level with the homebox form four import regions. The remainder of the comb 3250 forms remaining import regions. The multiple zone SNT method has a relatively complicated schedule shown in FIG. 33.

As for the NT method, multiple zone version of the SNT method eliminates redundant interactions and allows for some additional rounding opportunities. If the multiple zone SNT method is further generalized to include methods where there is no spacing between the bars of the comb, then the extended base disappears and the +x import subregion becomes unnecessary as it only interacts with the extended base. The remaining set of import subregions exactly correspond to the NT method. It can be shown that if one has the freedom to optimize the aspect ratio of a homebox in addition to the spacing between the bars in the SNT method, the SNT method is optimized by turning it into an NT method.

Figures 34, 35:
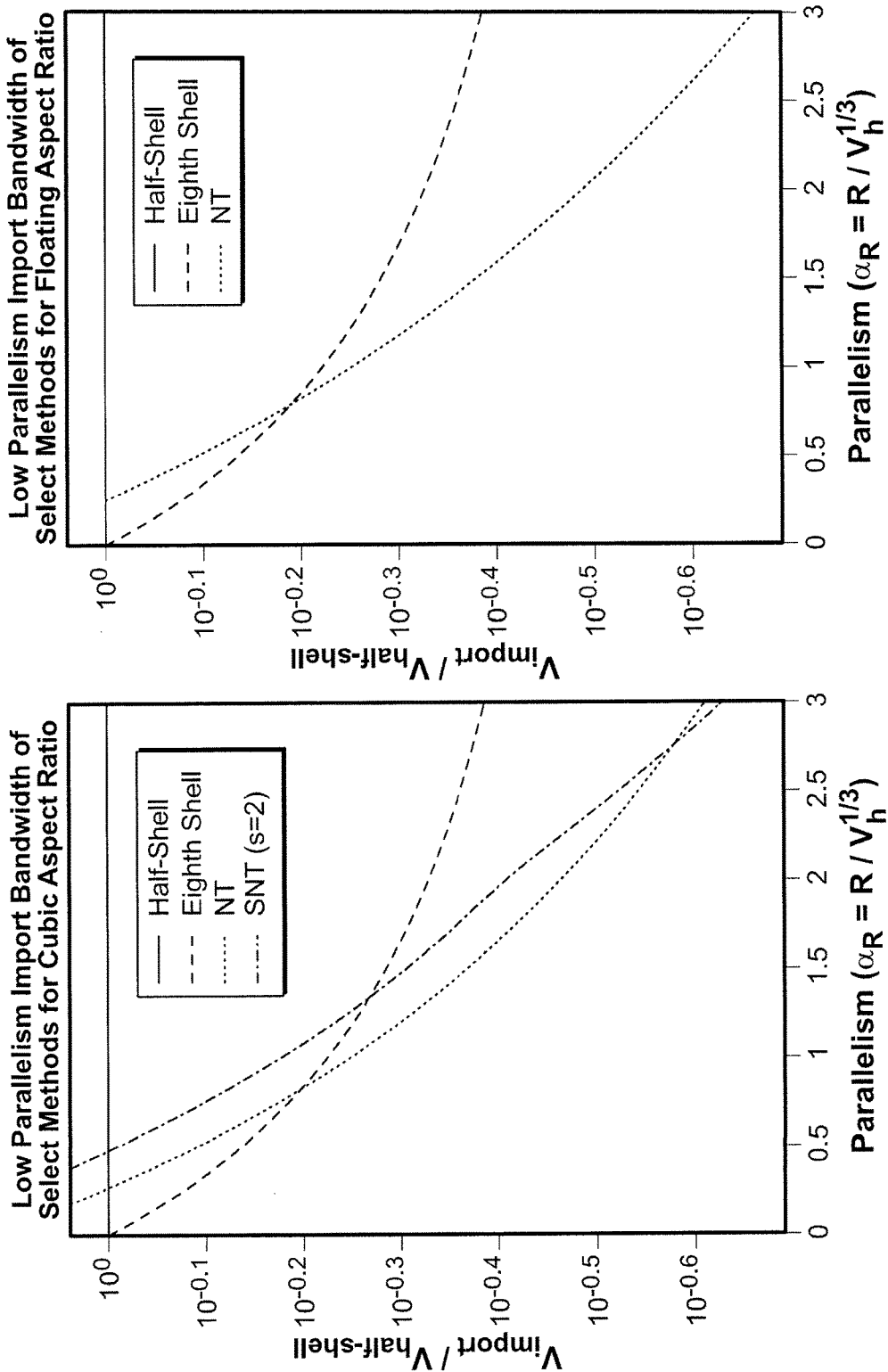
FIG. 34 is a graph of import volume versus degree of parallelism.
FIG. 35 is a graph of import volume versus degree of parallelism.

At sufficiently high parallelization parameters when the homebox aspect ratio is fixed, an SNT method with judiciously chosen periodicity will be superior bandwidth wise to the NT method. This can be understood by considering the optimization priorities. Appropriate for the higher parallelization regimes, both methods do not import any corner subregions. Further, both import the same number of edge-like areas. However, for a fixed aspect ratio, the NT method optimizes the number of face imports at the expense of balance of volume between the outer tower and outer plate. The SNT optimizes for balance of volume between the extended base and partial comb at the expense of the number of face imports. Asymptotically, the face imports are negligible contributions to the import volume so that for fixed aspect ratio, the SNT method achieves lower import bandwidth than the NT method. Based on the optimization priorities, the NT method is expected to be most viable in the parallelization regime $1.20 < \alpha_R < 2.25$, while the SNT method is expected to become viable beyond $\alpha_R > 2.25$. Accordingly, the crossover is at $\alpha_R \sim 2.7$ for cubic homeboxes as can be seen in FIG. 34

7.4 Foam Method

The foam method is the three-dimensional generalization of the method shown in FIG. 15. This variant of the foam method has the many rounding opportunities and imports a brick of homeboxes of dimension s×s×s centered in the x and y directions on the homebox whose top is level with the top of the homebox. The homebox also imports a foam of homeboxes with a periodicity of s×s×s. The bottom of the foam is level with the bottom of the homebox and the foam is rounded against the brick to form a hemispherical structure. (In the low parallelism limit, the brick can be rounded as well but the method is not competitive in that limit.) Asymptotically, the import volume of this method is:

$$V_{import,foam} \sim s^3 V_h + \frac{2\pi R^3}{3s^3}$$

Optimizing the periodicity to minimize the import volume yields:

$$s^6 \sim \frac{2\pi R^3}{3V_h}$$

Thus, the asymptotic import volume of an optimal foam method is:

$$V_{import,foam} \sim \sqrt{\frac{8\pi R^3 V_h}{3}} = \sqrt{\frac{8\pi \alpha_R^3 V_h^2}{3}}$$

The foam method achieves the exact lower bound asymptotically for a method with two remote zones. Practically, this method is best matched to situations in which the parallelization parameter is large. As can be seen in FIG. 34, foam only becomes competitive at parallelization parameters in excess of ~14. This is a consequence of the fact that as the number of processors increase, the relative contribution of the overhead of foam faces and foam corners to the import volume only declines very slowly.

Implementations of foam methods can be coupled with zone scheduling on a homebox-by-homebox level to "hide" import latencies from more distant homeboxes. Since the number of homeboxes imported is large when foam is practical, a zone interaction schedule is omitted for brevity. Conceptually, the key elements of the schedule are that the homebox is interacted with both the foam and the brick, while the foam and brick are interacted with one another.

7.5 Comparison of Communication Bandwidth Requirements

FIGS. 34 and 35 summarize the import volumes of a number of methods described above over a range of parallelization parameters. For cubic homeboxes, the ES method is best among these methods for $\alpha_R < 0.8$. The NT method is best between $0.8 < \alpha_R < 2.7$. The SNT method is best from $2.7 < \alpha_R \sim 14$. Beyond, foam methods are increasingly competitive. These transitions can be related to the number of processors used for parallelization. For example, consider a molecular dynamics simulation with N=25,000 atoms and R=12 Å. Biological systems have a density of atoms of roughly D=0.1/Å³. Assuming cubic homeboxes are being employed and that each atom is represented by a single particle, the parallelization parameter can be written in terms of these parameters:

$$\alpha_R = \frac{R}{V_h^{1/3}} = \frac{RD^{1/3}p^{1/3}}{N^{1/3}} \rightarrow p = \frac{\alpha_R^3 N}{R^3 D} \sim 145\alpha_R^3$$

The graph in FIG. 34 indicates that when using below ~75 processors, the eighth-shell method will minimize communication bandwidth (moderate sized clusters). Between ~75 and ~2,800 processors (large clusters), the NT method is best. Beyond ~2,800 processors (for example, in the range of ultra parallel hardware such as in BlueGene or QCDOC), more elaborate methods are preferable, beginning with the SNT method with a spacing of 2. The foam methods begin to become preferable at the extreme half a million processor level.

The relative import volumes of the various methods are different if the homebox aspect ratio is allowed to float. FIG. 35 shows the relative import volumes when each method is allowed to optimize the homebox aspect ratio, assuming a fixed global cell volume and number of processors. In this case, the eighth-shell is still optimal for $\alpha_R < \sim 0.8$, followed by the NT method, followed by the foam method at extreme parallelization levels. The floating homebox aspect ratio is particularly important for fully interconnected networks and in the massive parallelism limit. In practice, the global cell aspect ratio is usually fixed by phenomena being simulated. The set of available potential homebox aspect ratios is then set by the network topology and/or the number of ways the global cell can be partitioned among the processors. On fully interconnected networks though, the topology does not bias in favor of a particular homebox mesh. Similarly, if there are a large number of processors available for the simulation, the mesh may be partitioned very flexibly, especially if the exact number of processors used is not fixed. As a result, on such hardware, communication schemes may be improved by optimizing homebox aspect ratio on a per method basis.

7.6 Multiple-Particle Interactions

In the description above, various approaches are described in the context of computing pairwise interactions. The approaches are also applicable to computing interactions between sets of greater than two particles. For example, forces between atoms in a molecule can be arranged using these approaches. In the multiple zone approaches, for example using the ES method, particular combinations of more than two zones can be scheduled in order to arrange such multiple particle interactions.

For a midpoint method for interactions that involve three or more particles, computing the center of the smallest sphere containing m particles is computationally nontrivial when m≥3. One option for avoiding this computation is to use midpoint-ensured methods that do not require computation of a midpoint. Another is to use an efficient approximation for the midpoint. Two such approximations are:
 a. For each of the coordinate dimensions, approximate the coordinate of the midpoint as the arithmetic mean of the coordinates of the particles.
 b. For each of the coordinate dimensions, approximate the coordinate of the midpoint as the arithmetic mean of the coordinates of the particles.

When using either approximation, one needs to expand the import region slightly to ensure that the box containing the approximate midpoint of a set of interacting particles will import all remote particles in that set. In the absence of any restrictions on the spatial distribution of particles, use of approximation 1 requires that the import region contain all particles within a distance $$R\left(1 - \frac{1}{m}\right)$$

of the interaction box boundary, implying a substantial increase in import volume (if m−1 particles are collocated inside the interaction box at a distance $$\frac{R}{m}$$

from the boundary and the mth point is located outside the interaction box at a distance just under $$R\left(1 - \frac{1}{m}\right)$$

from the boundary, then the midpoint will fall within the boundary). In MD simulations using common biomolecular force fields, however, a smaller increase in import volume may be sufficient, because the spatial arrangement of the particles involved in a bonded term is not arbitrary; for example, any pair of atoms must maintain some minimal distance from one another under normal conditions.

A sufficient import volume for use of approximation 2 is that enclosed by a rectangular parallelepiped extending a distance R/2 beyond the interaction box in the positive and negative directions along each coordinate axis. One can show that a somewhat smaller volume suffices, one that includes all remote particles within a rectangular parallelepiped extending a distance R/4 beyond the interaction box in each dimension as well as all particles within a distance R/4 of that parallelepiped. In three or fewer dimensions, for m≥3, this import volume is always smaller than that required by approximation 1 in the absence of restrictions on the spatial distribution of particles.

8 Serialized Implementation

One approach to computation of particle interactions, which can include one or more of the algorithmic techniques described above, make use of a serialized software implementation. In such an implementation, a processing node performs computations for homeboxes in a serialized manner. For example, for each homebox, a multiple zone method is implemented in which interactions between pairs of particles in respective pairs of zones are computed by the processor. In one version of such a serialized implementation, a single processing node performs all the computations for all the homeboxes in a serialized manner. In another version, a single processing node of a set of multiple processing nodes is responsible for a set of homeboxes, for example, that together define a region of space (e.g., a cube). The processing node may have a number of processors that share at least some common memory. For example, each of the processors at a node may have a private cache memory and access a shared memory that is local to the node as a whole. There may be further level of memory, for example, shared between processing nodes, but that is not directly significant to the discussion below.

Figure 45:
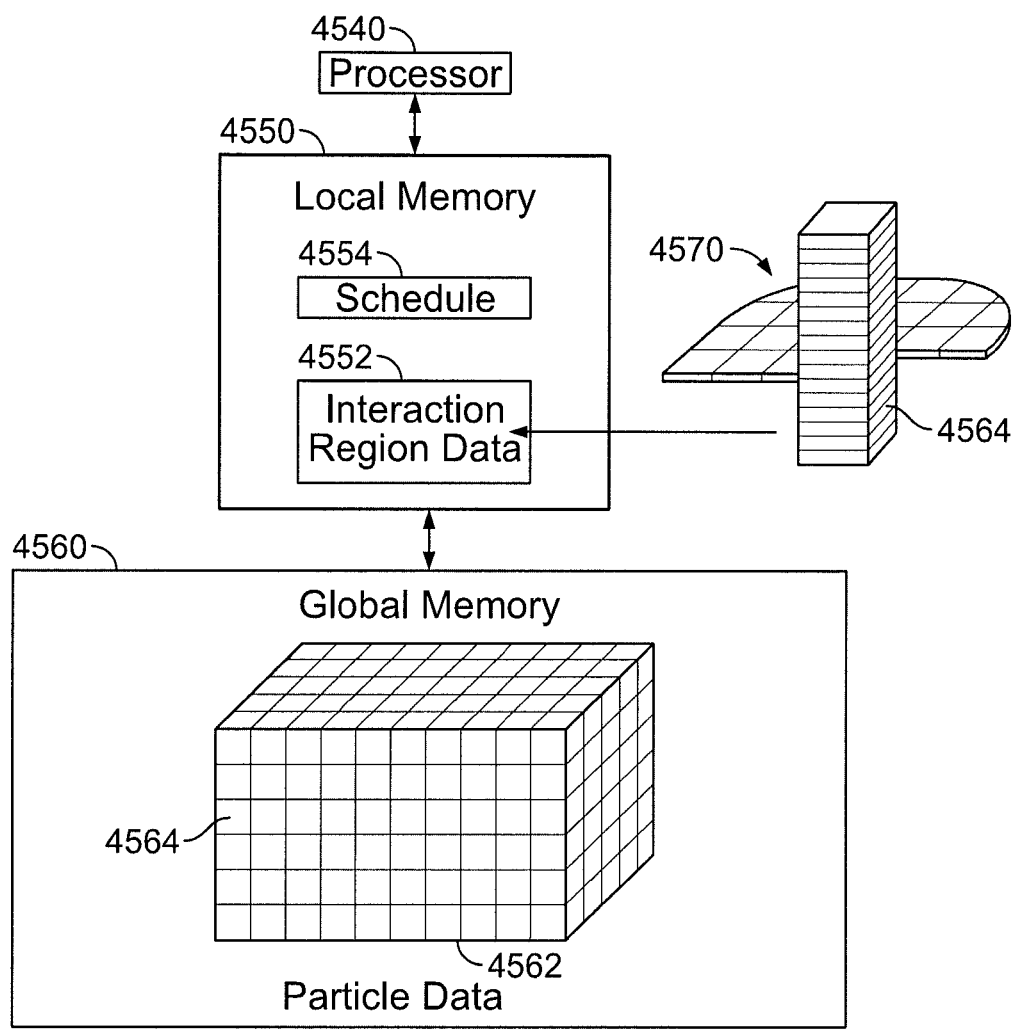
FIG. 45 is a block diagram of a serialized implementation.

Referring to FIG. 45, in one version of a serialized implementation, a processor 4540 uses a local memory 4550. For example, the local memory 4550 may be a fast cache memory that is associated with the processor 4540, and which provides local copies of data in a global memory 4560. The global memory 4560 holds the particle data 4562 for the entire global cell being simulated by the system.

One aspect of local or cache memories is that they are typically faster than larger memories, but are limited in size. Some arrangements of the computational iterations may result in relatively larger numbers of memory access to the global memory 4560 than others. To the extent that the number of global memory accesses is a significant factor that determines the overall time required for the overall computation, such arrangements of the iterations may require relatively more overall computation time.

There are speed advantages to maintaining all or most of the data required for a computation in the local memory 4550 if that data can be used multiple times. This reduces the overall memory latency in that an initial fetch of the data may be relatively slow, but subsequent accesses to the data that can use the cached copy of the data are relatively fast.

One way of making effective use of limited size caches is to "cache block" the near interactions. The term "cache block" is used as an analogy to cache blocking techniques used to accelerate matrix-matrix multiplication. Naïve implementations of large matrix-matrix multiplications require $O(N^3)$ data transferred to and from main memory (bandwidth) when the entire matrices being multiplied do not fit in the cache memory. Generally, this results from the entries in the matrix being repeatedly flushed and then reloaded into the cache as the computation continues. However, by breaking each matrix into a collection of "cache blocks" and determining an appropriate schedule cache blocks are loaded, processed and stored, matrix-matrix multiplication can be structured to have $O(N^2)$ bandwidth.

In computation of pairwise interactions, in a worst-case use of the local memory, computation of every interaction between a pair of particles requires accessing the global memory 4560 for at least one of the particles. For example, this may result if the order in which particles are interacted is not performed with regard to their locations, or if a method such as the half-shell method is used but the particle data for an entire half shell of data does not fit in the cache. In such a worst-case situation, the number of such global memory accesses is $O((DV)(DR^3)) = O(D^2 V R^3)$, where V is the volume being simulates, D is the density of particles, and R is the interaction radius. That is, DV is the total number of particles, and the average number of particles in with the interaction radius of a particle is proportional to $DR^3$. On average, for every load data for a particle into the cache, essentially only a single pairwise computation is performed.

In a cache block arrangement of the computation of pairwise interactions the number of global memory accesses can be reduced to $O(D\ V^{1/2}\ R^{3/2}\ N_v^{1/2})$, where $N_v$ is the number of "voxels" used. Specifically, the volume V being simulated is partitioned into $N_v$ voxels, in general, each being the same shape. In general, each voxel is analogous to a homebox in the decomposition approaches described above.

Referring to FIG. 45, the general approach to arranging the computation of the pairwise interactions involves loading the particle data for an import region 4570 and its associated homebox (i.e., the interaction zones associated with the homebox) into an interaction region data portion 4552 of the local memory 4550. The size of the import region, which depends on the volume and geometry of voxels, is chosen such that the data for the particles in the interaction region fits in the local memory 4550. Once this data is loaded into the local memory, any pairs of interactions between a particle in the interaction region can be computed without necessarily accessing the global memory.

The saving in access to the global memory can generally be understood by the number of times the data for each particle is used in a pairwise computation. In the case of two interaction zone, if the local memory is sufficiently large to hold the particle data for 2M particles (M from each of equal volume interaction zones), then up to $M^2$ interactions can be computed. That is, there are M/2 pairwise computations for every particle loaded into the cache, resulting in a M/2 speedup with respect to memory access time using a naïve worst-case method.

As one example of a type of interaction region, an NT approach, as described in Section 2.2 and illustrated in FIG. 3, is used. The interaction region 4570 is partitioned into voxels (voxel 4564 being indicated as a representative voxel). The local memory 4550 also includes a schedule that identifies the pairs of voxels that are to be interacted. For example, each voxel in the tower portion of the interaction region 4570 is interacted with each voxel in the plate portion. For each pair of voxels that are interacted, all the pairs of particles, one particle from each voxel, can be considered.

In other examples, the entire import region associated with a homebox does not necessarily fit in the local memory. However, if the import region is divided into multiple zones such that pairs of the multiple zones fit in the local memory, they can be loaded in the local memory according to a multiple-zone schedule and all the pairs of particles interacted while the data remains in the local memory. In other examples, subsets of zones are loaded into the local memory and all scheduled combinations of pairs of the loaded zones are interacted while the data for those zones remains in the local memory. In these examples, generally, an M/2 speedup is also achieved to the extent that 2M particles are loaded and $M^2$ interactions are computed.

For an optimal choice of height of voxel (i.e. a square cross-section tower, and a relatively thin plate), the volume of the import region is $O(R^{3/2})$ rather than $O(R^2)$ as with cubic voxels. For the NT method, the geometry of the voxels can be chose by optimizing the height of the voxel (the thickness of the plate) such that bandwidth scales as the total number of particles times the square root of the expected number of particles in an interaction region. Often, there are 200-400 particles expected in an interaction region so this square root reduction can be significant.

Various architectures of local memory can be used with these approaches. In one example, the local memory is a cache memory that uses the same address space as the global memory, and a cache controller maintains copies of the most recently accessed data from the global memory in the cache. As another example, a non-uniform memory architecture can be used in which the local memory uses a distinct address space than the global memory, and the processor explicitly copies the particle data from the global memory to the local memory as needed.

The approach can be extended to a multiple level cache structure in which a first level cache may have space to hold two subzones, which are read from a second level cache that holds more data, for example, the entire import region for a homebox.

The loading of data into the local memory may be aided by a special-purpose memory controller. For example, loading the data from one voxel can use a regular and generally relatively large memory structure that is performed using hardware external to the processor (e.g., special purpose FGPAs).

A multiple processor implementation can also be used in which each processor has its own local memory, and all the local memories are coupled to a shared global memory. The schedule of voxel pairs to interact is then split among the processors so that together all the required interactions are performed.

Between interactions, the particle data is reassigned to the voxels in which the are located (as a result of motion of the particles caused by the forces computed in the previous iteration). This partitioning of the data is performed using an efficient O(N) algorithm, where N is the number of particles. During the partitioning process, a data structure (an array) is built that allows efficient access to strips of adjacent voxels along one or the orthogonal axes are needed when loading an interaction zone into the local memory.

The order of voxels processed is chosen so that in addition to reduced memory bandwidth, particles loaded into the cache blocks for the interaction zones for one voxel will substantially overlap the particles for the interaction zones of the next voxel. This further accelerates the operations by increasing temporal hardware cache locality.

As described above, the computation involves computing interactions between pairs of particles loaded into the local memory in a schedule-based loop. One alternative it to defer computation of the interactions in this loop and rather computing a list of pairs of indexes of the particles to be interacted. Then this list is processed in a second loop to actually compute the interactions. This second loop may be accelerated using special-purpose hardware. Because the list of pairs is already computed, such special-purpose hardware may be relatively simple.

Non-commutative (e.g., grid-particle) interactions can be organized so that the zones and voxel sequencing is such that multiple processors can write without conflict to the same output arrays. For example, in computations where the output is a charge density array, this can eliminate the need to use one charge array per processor and the need to reduce these partial charge arrays into a single output array.

A specific instance of a highly optimized cache-blocking method is the dual of the NT method described above and has four cache block zones. The first zone is a single homebox voxel. The next zone is a "tower" of voxels. It consists of all non-homebox voxels along an axis-aligned voxel ray that starts on the homebox voxel and that contain at least one point within R of the closest point in the homebox voxel. The last two zones form an approximately circular plate of radius ~R. These two zones consist of all non-homebox voxels that contain at least one point within R of the closest point in the homebox voxel in the plane perpendicular to the tower that contains the homebox voxel. These two zones are split evenly into a "yin" zone and a "yang" zone. These were so named as the most convenient division of the plate results in symmetric zones that fit together like a yin-yang symbol.

The cache block zones are interacted as follows: homebox-homebox, homebox-tower, homebox-yin, tower-yin, tower-yang. The inner loop takes advantage of the packing of the cache blocks to merge these interactions into two composite interactions: homebox-(homebox,tower,yin) and tower-(yin,yang). It also sets up the inner loop such that no redundant pairs from the homebox-homebox interaction are considered. The only matchmaking criteria required is a distance check.

The zones are oriented such that the voxel strips used to encode the import region run parallel to long direction of the two plate zones. As a result, very few strips are needed to encode the import region. The outer loop is arranged to traverse the homebox voxels such that the plate needed for each outer loop voxel significantly overlaps the plates needed for the previous and next outer loop voxels, which improves temporal locality.

The serialized computation described above can be combined with a parallel architecture, for example, using cache blocking techniques with the processor at each node, while performing computations in parallel at different nodes and communicating the results between the nodes after the computation is completed.

9 Cluster architecture

Another approach to computation of particle interactions, which can include one or more of the algorithmic techniques described above, make use of a cluster architecture. In this architecture, a number of computers are coupled by a communication network, for example by one or more Gigabit Ethernet segments. Each computer can be a general purpose computer, for example, executing an operating system (e.g., Linux).

In one example, each computer in the cluster is assigned a particular set of homeboxes of the simulation region, for example, assigning computers to homeboxes in a one-to-one manner. Each computer includes storage for data for particles associated with its homebox. At the start of each iteration, the computers exchange particle data, for example, sufficient to implement a midpoint method for computing range-limited interactions. Other computations are also performed using this exchanged data, for example, using the communication sharing approach described in Section 4. Some computations are performed in a distributed manner over multiple computers. For example, FFT computations that are part of the GSE method can be implemented in a distributed manner.

10 Parallel Implementation

Another approach to computation of particle interactions, which can include one or more of the algorithmic techniques described above, makes use of special-purpose hardware that is particularly suitable for various computations necessary for computing particle interactions. The special purpose hardware is arranged in a parallel architecture that includes multiple processing nodes, with each processing node being responsible for the computations associated with one homebox. The architecture permits internode communication. One arrangement of nodes is in a three-dimensional array in which each node communicates directly with its six neighbors along three orthogonal axes, and communication of particle data can involve passing the data through multiple nodes to reach its destination.

Figure 37:
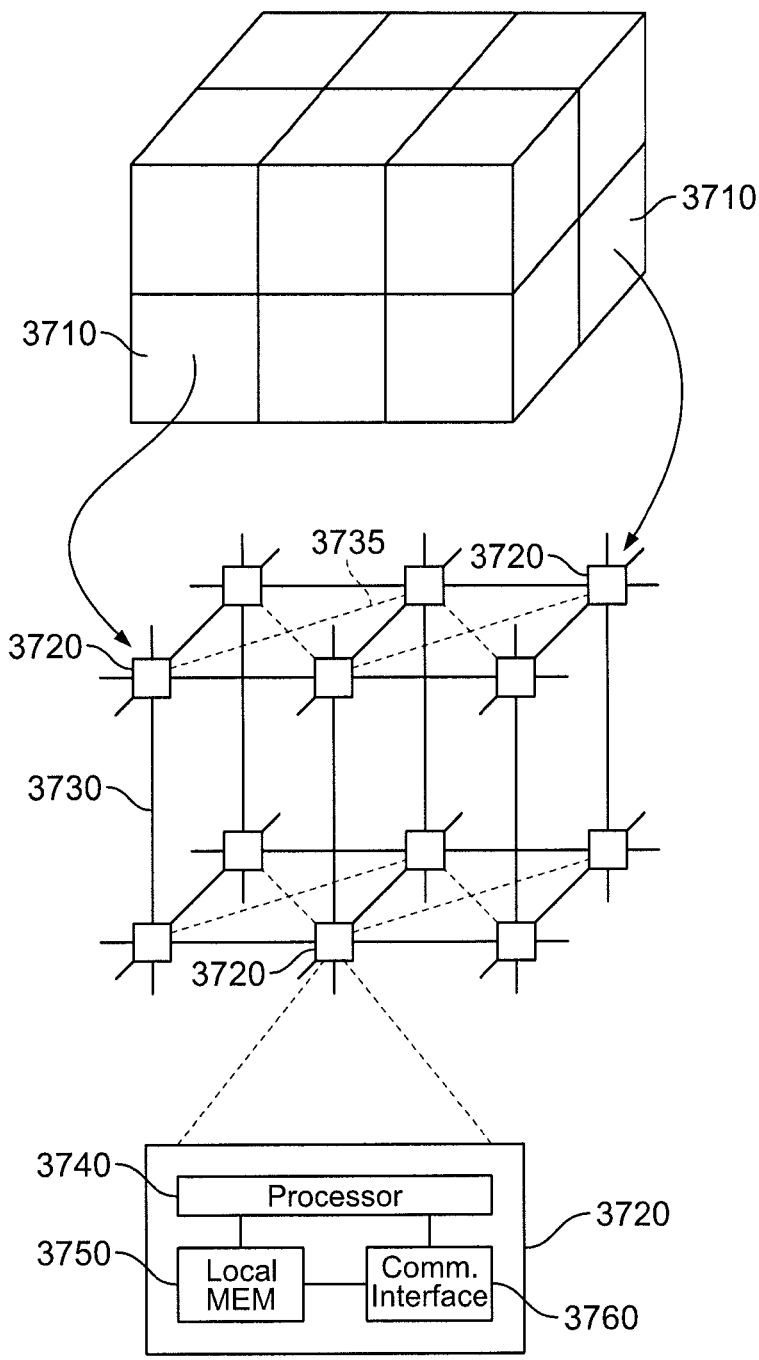
FIG. 37 is a block diagram of a parallel implementation.

Referring to FIG. 37, a representative three-dimensional array of computation nodes 3720 is arranged such that each node performs the computation for a corresponding homebox 3710. The nodes are linked by communication paths 3730 along the orthogonal axes, and optionally by diagonal communication paths 3735. Each processing node 3720 includes a processor 3720, which performs numerical calculations associated with the particle interactions, and a communication interface 3750, which is responsible for sending and receiving particle data over communication links 3730, 3735 linking the node to its neighboring nodes.

Figure 38:
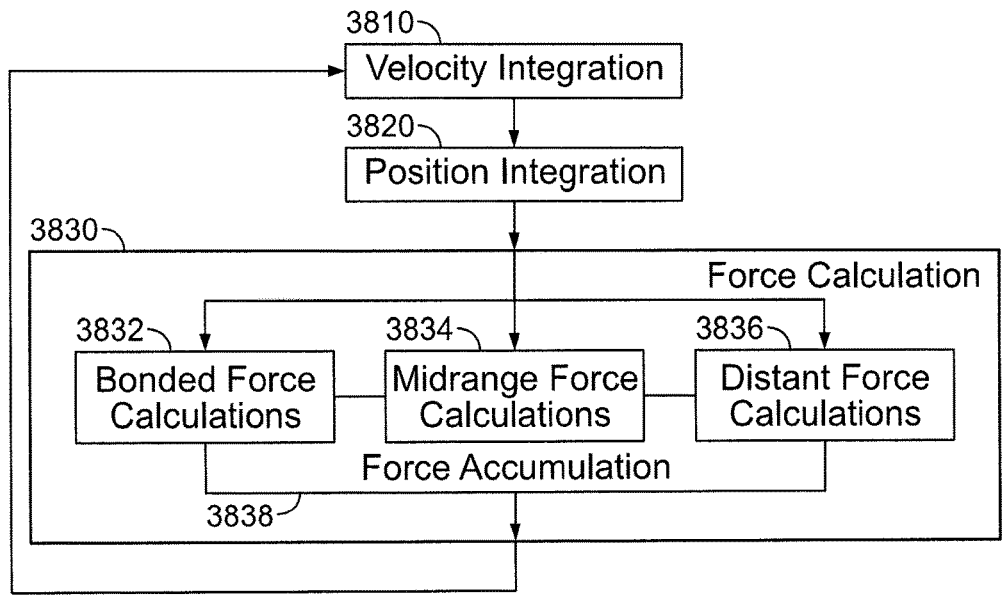
FIG. 38 is a flowchart.

Before discussing the details of the hardware implementation, the computation performed by the hardware can be understood with reference to FIG. 38. The computation involves a loop that is performed at each time step of the simulation, with each time step representing a simulated time such as 1 or 2 femtoseconds (abbreviated fs, equal to $10^{-15}$ seconds). Generally, each iteration involves three basic step. Velocity integration 3810 uses the calculated forces on each particle to update the velocity of that particle. Position integration 3820 uses the updated velocities to calculate the updated positions of the particles. Force calculation 3830 uses the new positions of the particles to calculate forces on the particles, thereby allowing the iteration to repeat.

Force calculation involves calculations at different spatial scales. These calculations are performed independently. There calculations include bonded force calculation 3832, midrange force calculation 3834, and distant force calculation 3836. As part of each of these calculations, force accumulation 3838 determines the total force on each particle, with the force on any particular particle potentially including components that are determined by computations at each of the spatial scales. It is not necessary to perform the force calculations at each of the spatial scales at each time step. The distant force computations may be performed less frequently than the midrange computations, which are performed less frequently than the bonded force calculations, for example, using a MTS (Multiple Time Scale) and/or RESPA (REference System Propagator Algorithm) approach.

Another aspect of the parallel implementation involves dedicating different hardware elements to various types or spatial scales of computations. For example, hardware elements are dedicated to computations involving pairwise particle interactions that are part of the midrange force calculation step 3834 (or particle-grid computations that form part of the distant force calculations 3836), and to computations of near interactions such that are part of the bonded force calculations 3832. In addition the force accumulation step 3838 makes use of a memory system that incorporates numeric value accumulation functionality. In the multiple node architecture introduced above, each node includes such dedicated hardware elements for the various types of computations.

Figure 39:
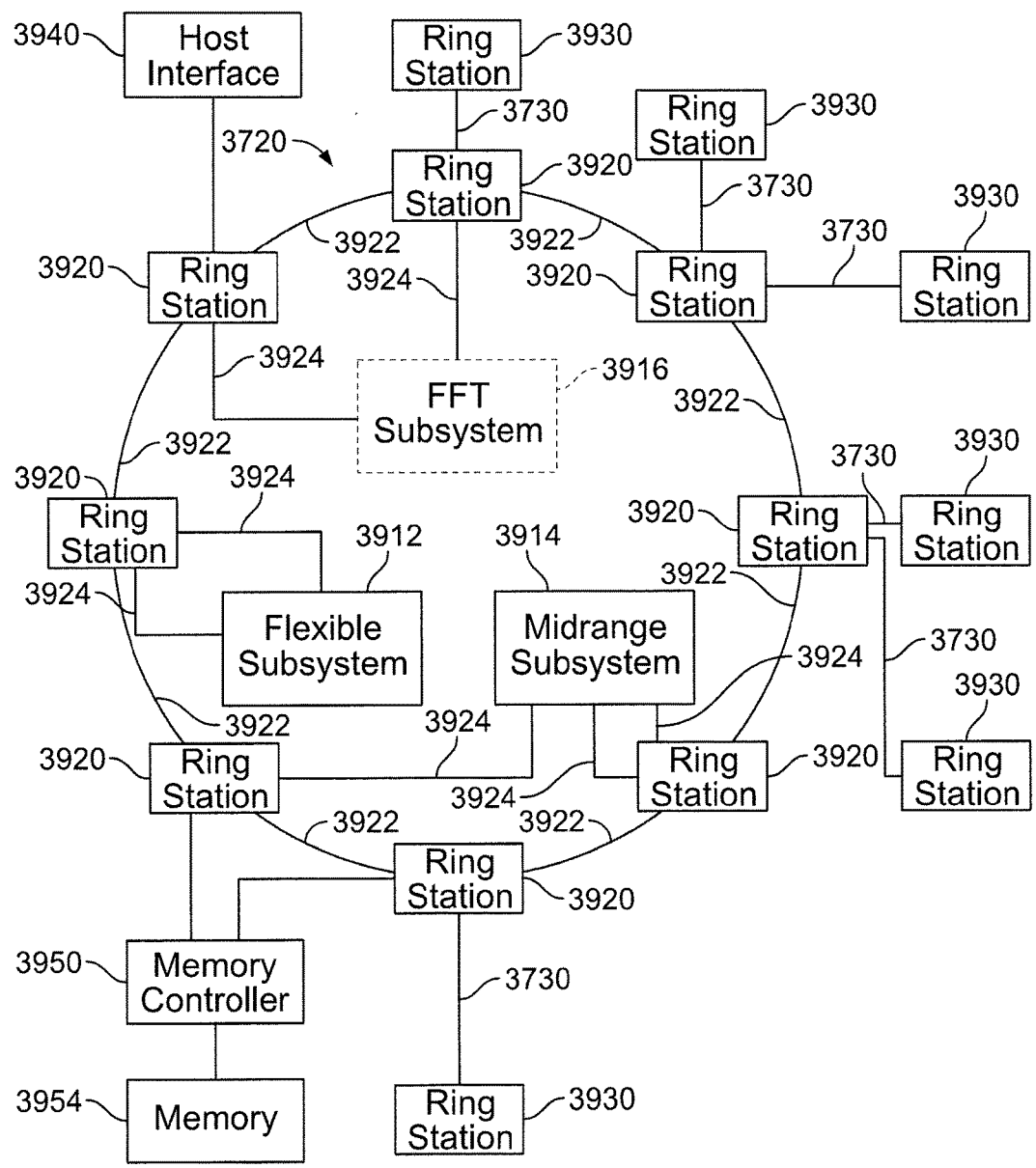
FIG. 39 is a block diagram including elements of a processing node.

Referring to FIG. 39, each computation node 3720 includes a number of computation and communication elements. A flexible subsystem 3912 includes one or more programmable processors. A midrange system 3914 includes special-purpose circuitry that is adapted to perform pairwise computations, for example, between pairs of particles. An FFT (Fast Fourier Transform) subsystem 3924 is used in some embodiments to perform computations related to distant force computations. Yet other embodiments may include additional or fewer specialized or general purpose computations elements.

Communication within one processing node makes use of a ring communication architecture that includes a number of ring stations 3920 coupled by communication links 3922. In this version of the system, there are eight ring stations per node, and the links are high speed serial communication links. Each ring station has additional links. For example links 3924 couple the ring stations to the computation elements of the node. Other links 3730 couple ring stations for this node to ring stations 3930 of the six neighboring processing nodes 3720 of the torroidal mesh of processors. Other links couple the ring stations to a memory controller 3950, which provides access to a memory 3954, and to a host interface 3940, which is used for example for administrative functions such as loading programs to be executed on the computation elements.

The communication architecture, which is made up of the interconnected communication rings on each node, supports a global addressing approach by which each computation or communication element coupled to a ring station can address a data packet to any other element in the system, which may be on the same node, or may be on another node. Also, as is described further below, the communication architecture supports forms of limited multicast that allows data packets sent from a source to be distributed to multiple destinations without necessarily broadcasting the packet to all nodes in the system or sending multiple copies of the data packet from the source node.

In general, implementation of the iteration illustrated in the flowchart of FIG. 38 using the node architecture illustrated in FIG. 39 involves partitioning tasks among nodes, and partitioning the processing steps among the computation elements of each node. Furthermore, each of the subsystems takes advantage of internal parallelism. Overall, the implementation provides parallel processing and pipelining of computations at multiple levels of the architecture.

Figure 40:
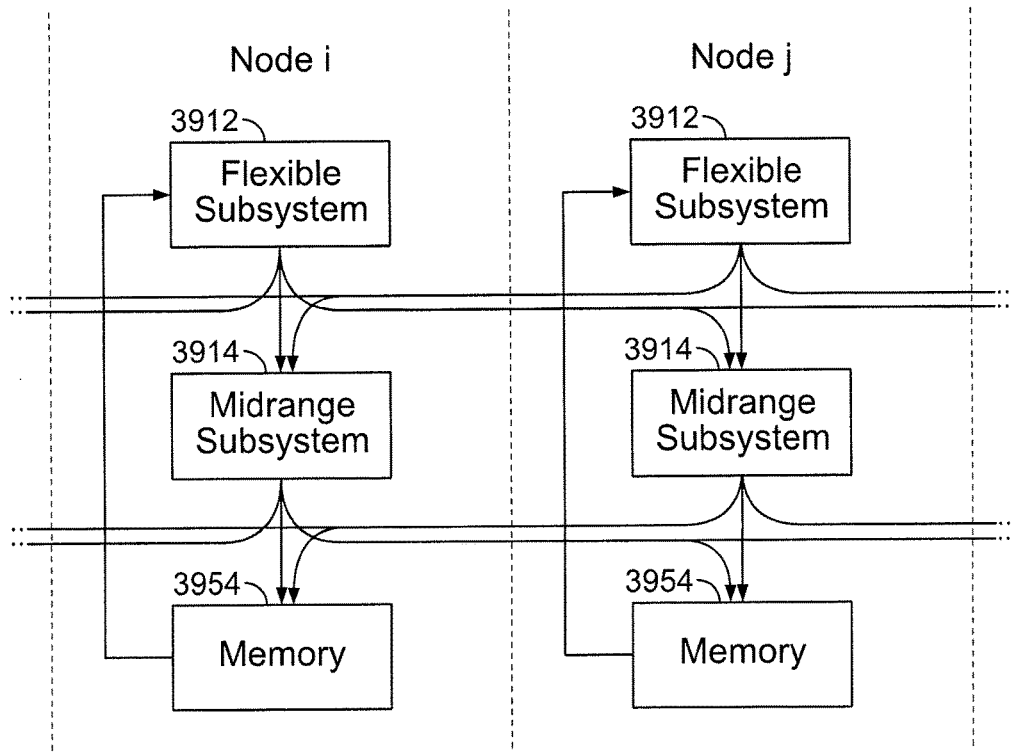
FIG. 40 is a diagram illustrating data flow in a processing iteration.

Referring to FIG. 40, computation elements for two nodes are illustrated, with indications of some of the data flows between the elements in a computation iteration. The communication links within a node and between nodes are not illustrated. The data flow that is illustrated relates to execution of the velocity and position integration steps (3810, 3820 in FIG. 38) as well as the midrange force calculation 3834. Other data flows, for example, related to distant forces and bonded forces are not illustrated in this figure.

Generally, at one point of the iteration time step, the flexible subsystem 3912 on each node retrieves particle force data for particles it is responsible for from its own memory 3954. Using the force data, it performs the integration steps required to determine the new particle positions. This particle position data does not have to be returned to the memories 3954. Rather, each flexible subsystem 3912 multicasts its position data, and this position data is passed to those midrange systems 3914 that will use the data to compute pairwise particle interactions, for example, using the NT method described above. In particular, the multicast approach ensures that the midrange subsystem of each node receives the particle data for the entire import region needed for the decomposition approach being used. Furthermore, data is "pushed" to the consumer of the data without necessarily requiring requests or acknowledgements for the data, thereby reducing communication load and delay associated with such communication.

In a pipelined manner, the midrange subsystems 3914 begins computing pairwise interactions as they receive the required particle data. For example, the midrange subsystem 3914 at a node may receive the particle position data for particles in that node's homebox relatively quickly over on-node communication paths, and then start receiving position data from neighboring nodes.

As the midrange system 3914 computes force contributions for particles, it distributes these contribution terms to the memories 3954 at the nodes responsible for those particles. The memories include accumulation functionality that allows the memory on sum the force contributions on each particle as the force contributions for that particle are received from various nodes. Using the accumulation function of the memories, different processors can compute components of a sum (e.g., of forces) and send them to a memory where the components are accumulated. Because the communication of the components does not require acknowledgement from the memories to the processors that produced the components, efficient accumulation is achieved. The memories implement the accumulation so that it is not order-dependent so that the identical result is obtained regardless of the order in which components to be summed together arrive at the memory.

Not illustrated in FIG. 40 are similar pipelined parallel procedures for the distance force computations, which involve grid-based computations that make use of Fast Fourier Transform (FFT) techniques that use multiple interchanges of data between nodes, and in some embodiments makes use of the specialized FFT subsystem 3916 to implement the FFT computations.

Referring again to FIG. 39, the communication system supports packet-based message interchange between elements on the same or on different nodes. Packets can represent operations including read, write, accumulate, and read-modify-write with the packet header specifying the operation and the packet body carrying operands (e.g., values to the written). A global address space is used for registers, memory locations, etc. in any node, with a 48-bit address space having 16 bits reserved for node number and the remaining 32 bits for 4G address locations (e.g., bytes) at each node. Different address ranges at a node map to different ring stations on the node based on routing information stored in the ring stations, and at each ring station, different address ranges are mapped to different subsystems coupled to the ring station. Packets are variable length having between one (i.e., a header only) and nine units of length (a header plus eight units of data), with each unit being, for example, 256 bits.

Each ring station is programmable with respect to routing, and is configured for a particular routing pattern before the simulation iterations are started. Each ring station includes a configuration table that is loaded before processing begins. In some examples, this table specifies a set of production rules that are applied to each incoming data packet. In general, the table in each ring stations specifies how packets that arrive at that ring station should be handled. Each packet that comes in is passed on one (or more) of the other ports (which can send the data off to another node, or on its way to a module on the same node) according to the table based on the source or destination address, and optionally based on a packet type. The configuration table can also specify an address translation function to be performed on the data before it is forwarded. Every ring station in this embodiment has two ports for communication on the ring, and two client ports, for example, for connecting to ring stations at other nodes or for connecting to computation elements at the node.

Typically, messages that are sent from client to client are not acknowledged. However, for some communication an acknowledgement may be generated by the destination element and used for synchronization purposes. This embodiment does not perform error correction if there are communication errors for example by retransmission. Rather, the computation is restarted from a previously checkpointed timestep. Checkpoints are generated periodically, for example, with a period ranging from approximately one second to one minute of real time.

One use of the multicast mechanism is for distribution of various types of data to nodes according to the type of data. For example, depending on the import region for particle data, the processors that need copies of particle data from one processor is determined by the geometry of the import region. The ring stations of the communication system are configured such that the source processor for the particle data does not need to be aware to the communication interconnections across which the particle data must pass, or where copies of the data are to be made. Rather the source processor tags the data with a group id corresponding to the type of data, and the communication system distributes it to all processors that need to import than data according to the configuration of the communication system.

A multicast mechanism is provided for distributing position data, for example, in the implementation of the NT method discussed above. Multicast is implemented using a limited range of destination addresses, each corresponding to a different class of multicast communication, referred to as the multicast group id. A flag elsewhere in the header of a packet indicates that the message is a multicast rather than a unicast packet. When a multicast packet is received at a ring station, the multicast group id and the source node address, which is also in the header, are examined and based on those values and on the address of the receiving node, the packet may be replicated and sent on one or more output ports of the ring station according to the ring stations routing tables. Therefore, a different pattern of multicast can be configured for each different multicast group id. Note that acknowledgements are not required. The configuration of the multicast pattern is distributed among the ring stations, each of which has a limited view of the overall routing pattern.

Inside each client module (e.g., a computational subsystem), interface hardware monitors "writes" from the ring station and based on pre-specified writes generates signals (e.g., flags, event codes) that may initiate appropriate computations within the client, for example, as a result of polling the generated signals.

In addition to the toroidal-mesh interconnect network, the system can optionally have additional other interconnect topologies for different patterns of communication. For instance, certain global quantities such as the temperature or pressure of the system may need to be computed. Global communication patterns may also be required to synchronize the nodes. Options for the additional topologies include a low-latency but not necessarily high-bandwidth tree structure. In the present implementation, routing protocols are layered on top of the mesh interconnect to provide a virtual topology of the required type for the different communication patterns.

Each subsystem at a node in general includes its own internal memories, which are separate from the memory 3954. The memory controller 3950 includes a cache (e.g., that uses fast static RAM), which for many simulation scenarios is sufficiently large to hold the data for all the particles being handled by the node. The memory 3954 includes a larger storage space, which may be DRAM, which can be used for larger problems where each node is responsible for more particles. The interchange of data between the SRAM cache and the DRAM is coordinated in a buffering arrangement in which data in one buffer is being transferred while data in another buffer in the SRAM is being used for a computation.

For many of simulated systems (e.g., those of dimensions roughly 128 Å cubed, or smaller), it is expected that the memory 3954 managed by the memory controller 3950 will not necessarily be used. In these cases, the primary purpose of the memory controller is the accumulation of force data. The cache of the memory controller is designed for high bandwidth accumulation of force data produced by the midrange or distant interactions in the midrange subsystems and the bond terms and corrections produced by the flexible subsystems. The memory subsystem of any specific node is responsible for accumulating force data for the particles owned by that node.

For large scale systems, the memory 3954 includes 1 to 2 GB of DRAM at each node. In modes that use this DRAM, the system may be partitioned system is sub-partitioned— each box partitioned into sub-boxes—and the algorithms described above are implemented on a sub-box by sub-box basis, with the required sub-boxes being pulled out of DRAM to the memory controller cache as necessary. Note also that such a sub-box mode can in fact be used on smaller systems, before data exceeds the capacity of the memory controller cache, and there may be cases where this yields a performance advantage.

The subsystems described above and shown in FIG. 39 cooperate in the evaluation of a force field, the parameters of which are provisioned at the beginning of any simulation run. At the beginning of a simulation, the parameters of the force field, together with the description of the system—the particles (e.g., atoms) involved, their connectivity (e.g., covalent bonds), their positions in space and their current velocities—are all known and partitioned appropriately among nodes of the system. Specifically, the particle data (positions and velocities) reside in the flexible subsystem of an particle's homebox. In addition, each bonded term has an "owner" node, responsible for its computation.

The flexible subsystem 3912 is the "choreographer" of each simulation timestep. While most of the remaining subsystems are responsible for computation of the force field, the flexible subsystem implements the integration algorithm, which computes accelerations from forces, and increments velocities and positions incrementally from timestep to timestep. The integrator that is implemented for any particular type of simulation may require more than just simple integration: it may, for example, implement a constant temperature simulation—which generally requires the periodic calculation of temperature throughout the simulation. This in turn requires calculation of kinetic energy from velocity data, and the synthesis of a global scalar, the temperature, from this data. Such a particular computation, and others like it (pressure control, for example), are implemented by programming the flexible subsystem for these specific tasks; in this particular example, the flexible subsystems of all nodes must cooperate in computing a global reduction to compute this global scalar.

Before continuing with a detailed discussion of the overall computation timestep, or the architecture of the flexible subsystem, it is useful to consider the function and implementation of the midrange subsystem 3914.

The midrange subsystem 3914 can be thought of as a generic implementation of the NT Method that supports a much broader range of algorithms and decompositions. The subsystem is designed to efficiently calculate all pairwise interactions among point objects, whether particles or grid points, locally within a specified cutoff radius. One of its chief tasks is the computation of midrange non-bonded interactions through full pairwise summation. It is also used in the real-space components of the distant force calculation, for charge spreading and force interpolation.

Figure 41:
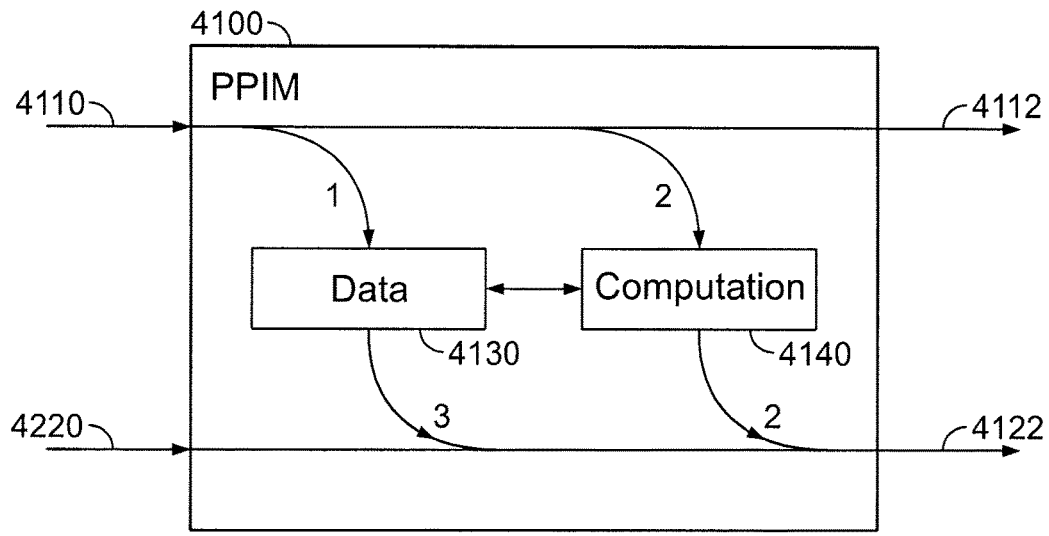
FIG. 41 is a functional block diagram of a particle-particle interaction module (PPIM).

Referring to FIG. 41, operation of the midrange subsystem can be understood by considering a single particle-particle interaction module (PPIM) 4100. Generally, for computation of interactions between particles, during each iteration, memory in PPIM is first loaded with particle data for one set of particles at the beginning of the iteration. Then, particles in another set are streamed past the PPIM producing force contributions on the particles being streamed past. At the end of the iteration, force contributions for the particles that were resident in the PPIM is streamed out.

In some examples of computations performed by a PPIM, the PPIM operates in three phases. In the first phase (indicated by the circled numeral 1 in the figure), data for a first set of points, such as particles in the "tower" region for the NT method, are received over an input 4110 and stored in a memory 4130 of the PPIM. In a second phase, data for a second set of points, such as for particles in the "plate" region for the NT method, are received over input 4110 and passed to a computation element 4140. For each received particle, the computation element computes the total force (or other accumulation of pairwise computed quantities) on the particle from all stored particles, which were loaded in the first phase. This accumulated force is passed on an output 4122. In this second phase, there is one force send on output 4122 for each particle received on input 4110, with the ordering preserved. During the second phase, forces on the particles stored in memory 4130 are also accumulated. In the third phase, these forces are sent on output 4122, with one force sent for each particle receive on input 4110 in the first phase.

The PPIM includes storage for a number, for example three, different computations. In this way, different computations can be performed by the PPIM without reloading data, for example, allowing the first phase (data loading) phase of a second computation to be performed during the third phase (result unloading) phase of a first computation.

Figure 42:
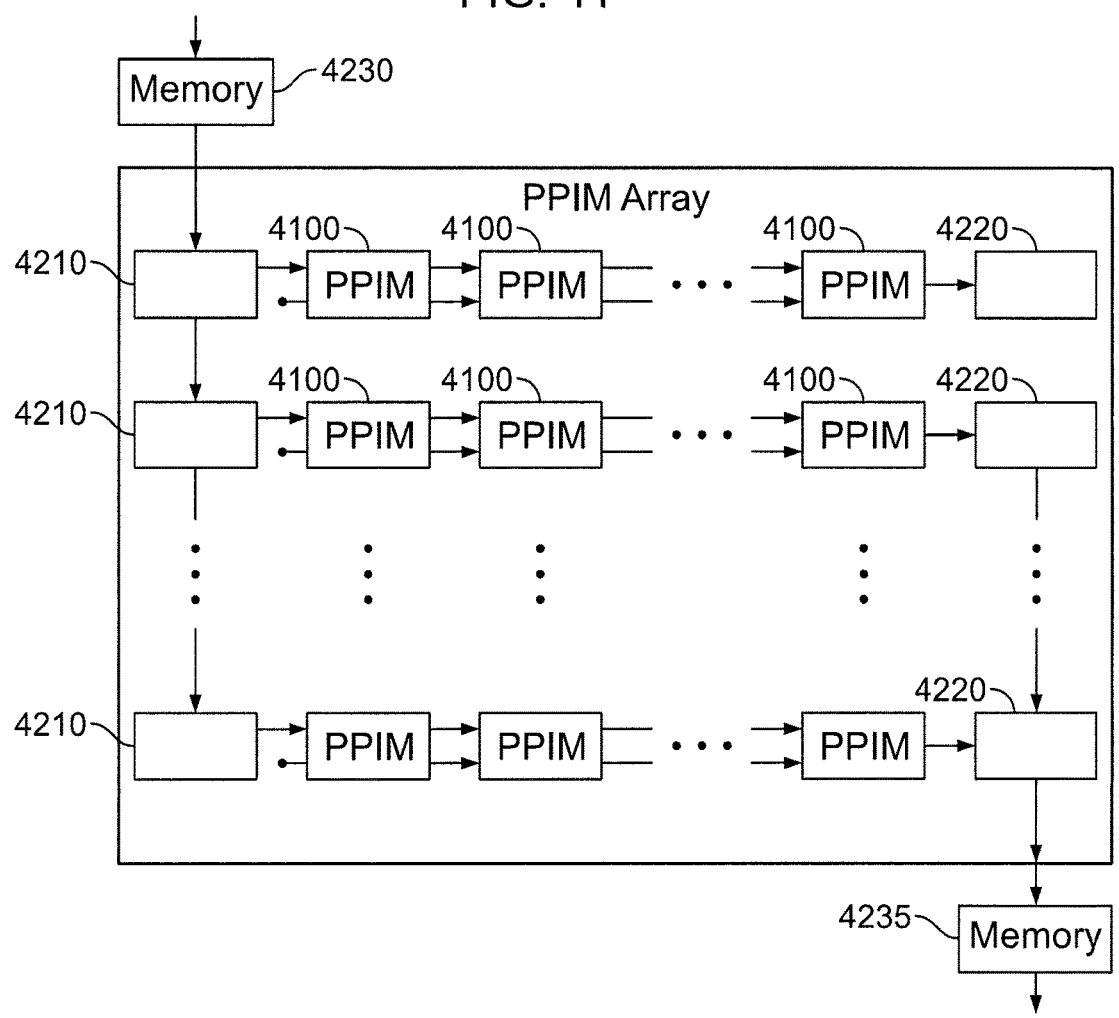
FIG. 42 is a block diagram of a portion of a midrange subsystem.

Referring to FIG. 42, the midrange subsystem implements a degree of parallelism by replicating the PPIM 4100 illustrated in FIG. 41 so that each PPIM performs only a subset of the required computations. In general, during the first phase, each PPIM receives only a portion of the first set of particle data, and in the second phase receives all the data in the second set. The outputs of all the PPIMs are then merged to yield the same result as would have been obtained by a single PPIM acting serially.

The midrange subsystem includes an array PPIMs 4100, as well as memories on the input 4230 and output 4235 of the array. The PPIMs are arranged into multiple rows, each with multiple PPIMs. In the present implementation, each row has eight PPIMs and there are four rows, but other arrangements can also be used.

Considering first one row of PPIMs, each PPIM passes data on its input 4110 (see FIG. 41) to its output 4112 without modification so that in the second phase of computation, each PPIM in a row receives data for the same set of particles. During the first phase, the data for the particles in the first set are also passed from PPIM to PPIM, but each PPIM stores only a separate portion of the data. During the second phase, the output 4122 of each PPIM includes one accumulated force for each particle input on its input 4110. At each PPIM (after the first, left-most) the PPIM receives a partially accumulated force for each particle on its input 4220, and internally sums the input contribution for that particle with the contribution computed by its computation element 4140, so that the output 4122 again has one force for each particle on its input 4110. Therefore, each row of PPIMs functions as a single PPIM, but performs more computations in parallel and therefore achieves higher throughput.

During the third phase, each PPIM streams out the accumulated forces for each point in the first set that was loaded to that PPIM, with "downstream" PPIMs in the row passing that force data without modification, with the overall order produced by the row matching the order the particles were loaded into the PPIM row during the first phase.

Considering the multiple rows of PPIMs, the data for the first set of particles is partitioned as it is read in so that each row has a separate portion of the first set. The data is passed through a set of distribution units 4210 to achieve this partitioning. The result is that each PPIM holds in its memory 4130 a different portion of the first set of points, with the PPIMs together holding all the points.

During the second phase, the distribution units 4210 replicate the particle data such that the same sequence of particles are sent to each row of PPIMs, and therefore also to each PPIM in that row. This results in each row of PPIMs producing a force for each particle in the second set, and these forces must be accumulated across the rows. This accumulation is performed by the accumulation units 4220.

During the third phase, the accumulation units 4220 concatenate the force data for the particles in the first set, so that at the output of the last accumulation unit 4220, the forces for the particles in the first set exit in the same order as the particle data was passed to the array in the first phase.

The midrange subsystem includes a front-end memory 4320, which received the particle data multicast from the flexible subsystems. A controller (not shown) monitors the writes to this memory and coordinates the passing of data to the array when the required data is available. The subsystem includes a back-end memory 4235, which is used to stage the computed forces (or other data). Note that this data is sent to the memory subsystem without waiting for completion of the processing so that some forces are being sent to the memory while other forces have not yet been computed.

Figure 43:
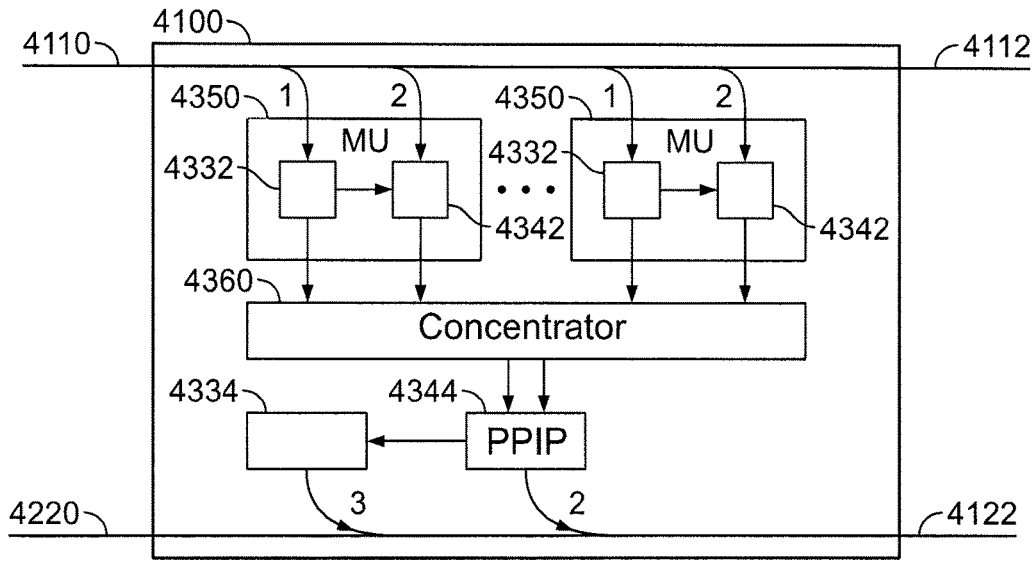
FIG. 43 is a block diagram of an implementation of a PPIM.

Referring to FIG. 43, each PPIM implements a further level of parallelism. Each PPIM contains several matchmaking units (MUs) 4350. In the present implementation, each PPIM includes eight MUs. The particle data distributed to the PPIM during the first phase, described above as being stored in memory 4130 (see FIG. 41), is actually distributed to memories 4332 in the MUs. That is, the particles in the first set are partitioned among the MUs. During the second phase, all the particles received by the PPIM are steamed past each matchmaking unit. For each received particle in the second set, a computation element 4342 of an MU determines which points stored in that MU's memory 4332 should interactions be computed, based primarily (but not exclusively) on the distance between the particles. The computation element 4342 passes the selected pairs to a concentrator 4360, which receives such selected pairs from each of the MUs, and acts essentially as an arbitrator for passing the selected pairs in a serial manner to a particle-particle interaction pipeline (PPIP) 4344. The PPIP then computes either the force on each particle due to the other or the potential energy contribution from the pair. The PPIP can be configured to compute a rather general function of the particles, based on their identities and inter-particle distance, and calculated by table-lookup and interpolation. For example, the PPIP is implemented or preconfigured to support a number of different functional forms, with data loaded into the PPIP determining the specific function within that functional form. The PPIP accumulates the forces for each particle in the second set for different of the stored particles, and passes the accumulated forces on output 4122 while storing the forces on the stored particles in a memory 4334. In the third phase, these stored forces in memory 4334 are streamed out on output 4122.

In some implementations of the PPIP, the functions that can be computed by the PPIP are represented as piecewise analytic functions. That is, within each of a set of ranges of argument value, a parametric analytic function is used to determine the function of the argument. A data structure stores the parameters of the analytic functions for the corresponding different ranges of argument values. A variable precision approach is used such that in different sizes of ranges of argument value can correspond to different parameters of the analytic function, for example, giving higher precision or greater accuracy in some ranges of argument value than in others. The selection of coefficients is performed in two stages. First, the argument range is divided into N coarse ranges, each of which can have a different size. Each of the coarse ranges is divided into the same number n of subranges, such that within each coarse range the subranges have the same size. For a particular input argument, first the coarse range is determined, and then the subrange within that coarse range is determined in order to look up the appropriate parameters of the analytic function. Therefore, there are N times n sets of coefficients. Given a limited number of sets of coefficients that can be used, the accuracy of the function to an ideal function can be chosen according to the argument range. An example of such a ideal function is erfc(1/R) and an example of the analytic functions are quadratic functions.

The PPIM array of the midrange subsystem in also used for charge spreading and force interpolation computations of the GSE methods described earlier in this document. For both charge spreading and force interpolation (the first and last thirds of the distant computation) particles are distributed to the PPIMs in a first phase, and the grid locations are streamed past the PPIMs in a second phase. Note that grid locations for the homeboxes of neighboring nodes streamed, as well as grid locations of the current node's homebox. Note that for this computation using an NT method, a "full plate" is needed because there is an ordering for the particle interaction so two equal and opposite forces are not computed at one time. During the charge spreading, no data needs to be accumulated by the PPIMs and streamed out in the third phase, while in force interpolation, the PPIMs do not need to provide outputs during the second phase, with the interpolated forces being accumulated during the second phase and streamed out of the PPIMs in the third phase.

Figure 44:
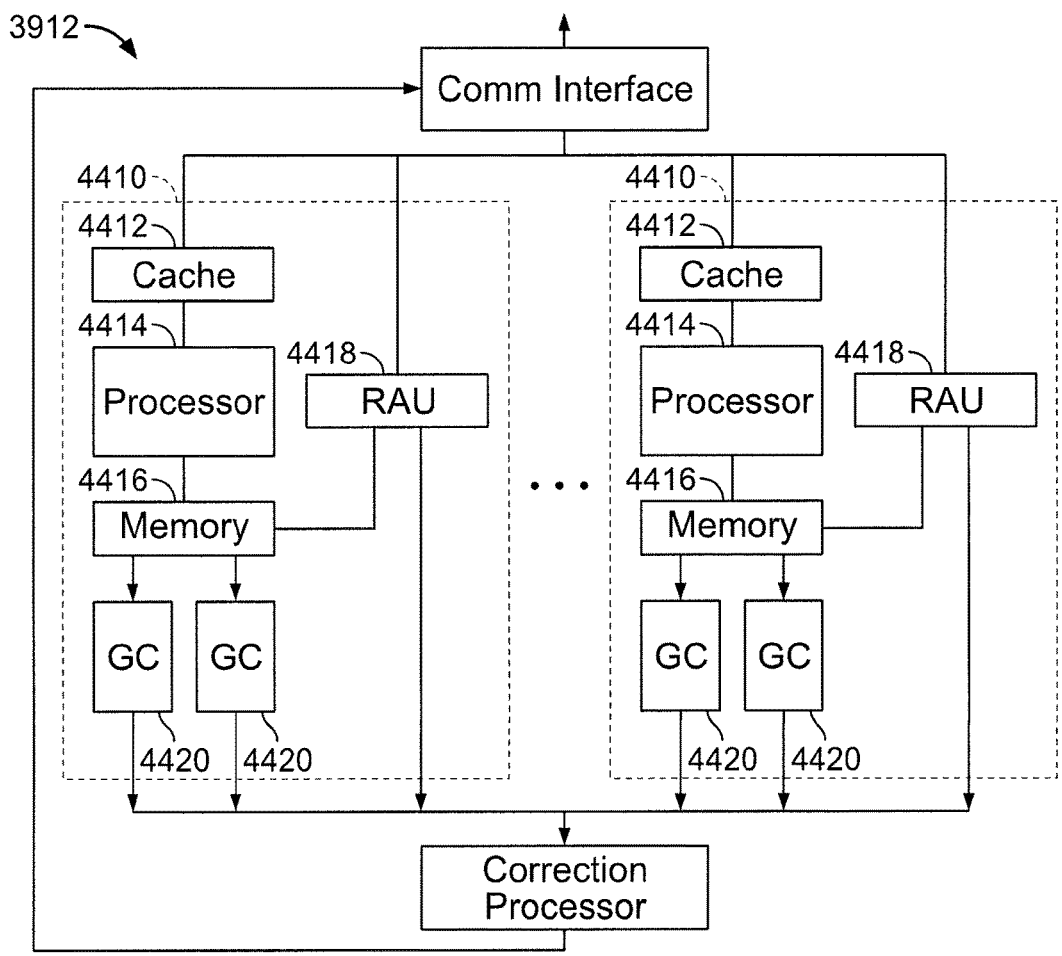
FIG. 44 is a block diagram of a flexible subsystem.

The flexible subsystem 3912 also implements parallelism within the subsystem. Referring to FIG. 44, a groups of computational elements 4410 function relatively independently in parallel. Not only is each particle assigned to a particular node within the system (i.e., the node associated with the homebox holding the particle) each particle is assigned to a particular group 4410 within the flexible subsystem of that node. In the present implementation, there are four groups of computation elements 4410.

Each group 4410 includes a processor 4414. Each processor has data and instruction caches (32 KB) 4412 that are backed by the memory system accessed over the communication ring. In many applications the caches 4412 are sufficiently large to be able to hold all the data needed for an iteration. Each processor has a remote access unit (RAU) 4418, which implements functions including direct memory access (DMA) functions for transferring data from the memory over the communication ring to a memory 4416, which is accessible to the processor 4414. The particle data that is the responsibility of processor is held in memory 4416, and the RAU 4418 retrieves force data for those particles from the memory subsystem using a DMA approach without loading the processor 4414. The RAU is coupled to a ring station through a communication interface, which aggregates outputs and distributes inputs to the flexible subsystem to the appropriate elements (e.g., based on the addresses of received packets).

Each processor has a number of slave special-purpose co-processors 4420, referred to below as "geometry cores" (GCs). In the present implementation, there are two GCs per processor. Each GC has a four-way SIMD architecture, dual issue VLIW pipelined ALU, and includes "geometric" primitives including computation of inner ("dot") products. Each GC uses a vector/scalar register architecture in which registers can be addressed in an interleaved manner as either n vector registers or as 4n scalar registers, and where scalar results can be placed directly in a portion of a register where needed for subsequent computations. There are inbound queues for the GCs that are fed by its processor, and outputs from the GC can be fed back to the memory system without requiring handling by the processor.

The GCs are used to compute bonded force terms. Each bond is assigned to a particular GC, and the processors exchange particle position data so that each processor has the data it needed to have its GC compute bonded force contributions. Note that a processor that computes a bonded force contribution may not be responsible for any of the particles in that bonded pair. Periodically (e.g., every 2000 time steps) a reassignment of bonds to processors and GCs may be performed as an optimization that may reduce communication requirements.

In a computation iteration, particle position data is distributed among the memories 4416 of the processors of the flexible subsystems of the nodes of the overall system. From there, the particle locations are sent to the midrange subsystems for computation of the pairwise interactions, and to other processors for computation of bonded terms.

The flexible subsystem 3912 also includes a correction processor 4430 which is used to add correction terms to values computed by the GCs. The correction processor implements an example of a general computational approach. In its general form, if one computation is to be performed on a large part A of a data set and a second computation is to be performed on a small part b of the data set, where A and b form a partition of the complete data set, and the results of the computations are to be accumulated (or more generally reduced) over the data set, then it may be efficient to perform and accumulate the first computation over the entire data set, and then for the small part b recompute and subtract the result of the first computation and compute and add the result of the first computation. For example, by not having to make exceptions for elements of the data set in part b, the first computation may be made efficient by regular (i.e., condition or exception free) iteration. In the context of particle interactions the entire data set (i.e. A plus b) can correspond to a set of particle pairs that are within an interaction radius, the first computation can be a unbonded interaction, for example, as computed in the PPIM array, and the second computation can be a bonded interaction as computed in the GCs. So rather than having to exclude bonded pairs of particles that are within the interaction radius from force computations in the PPIM array, when a bonded interaction between particles is computed a GC, the correction processor 4430 computes the negative to the unbonded term that is computed in the PPIM for that pair of particles, and adds it to the bonded term before it is sent to the memory where it is accumulated. In some implementations, the correction processor includes the same computational structure as a PPIP 4344, further ensuring that exactly the same unbonded term is computed for subtraction from the total.

There are generally three major computations that are hosted in the flexible subsystem: bonded force terms, constrain terms and integration (performed without the constraints), and finally updated positions accounting for the constraints. During the computation of distant forces, the processors and the GCs also perform performing the FFT calculations in versions of the system that do not include a dedicated FFT subsystem.

In versions of the system that use the flexible subsystem to perform the FFT computations, the distant forces are computed by first distributing charges to the grid locations using the midrange subsystem. These distributed charges are returned to the flexible subsystem, which implements a distributed FFT computation for the grid spanning the entire simulation volume. The FFT is distributed among the processors (and their associated GCs) and requires multiple phases of exchange of intermediate results between the nodes. At the end of the FFT iteration, the transformed data, which represents potentials at grid locations, is passed back to the midrange subsystem, where it is used to compute interpolated forces on the particles. These interpolated forces are then sent to the memory subsystem whether the distant force terms are combined with the other force terms computed for each particle.

In the present system, each node is implemented using an application specific integrated circuit (ASIC) that includes all the computation and communication subsystems shown in FIG. 39, with the exception of the memory 3954 and remote ring stations 3930. Multiple ASICs are arranged one each of multiple circuit boards that are interconnected through a backplane. The internode communication links 3730 are therefore either local to a circuit board or are routed through the backplane.

11 Applications

The algorithmic techniques, or the hardware or software techniques, described above may be applicable to a variety of applications, some of which are related to biomolecular simulation while others are not. The applications may include, for example, the following:

Biomolecular simulation applications related to use of molecular dynamics, Monte Carlo simulation, or other sampling technique, can include without limitation: ab initio protein structure prediction, refinement of homology models of protein structure, modeling of protein folding kinetics, computation of protein-ligand binding free energies, determining whether a pair of proteins will interact; determining their binding site and their binding free energy; toxicology studies; computation of hydration free energies; protein design; modeling allosteric changes and protein function; simulation of membrane proteins; simulation of nucleic acids; simulation of carbohydrates; simulation of combinations of the above and interactions between them; predicting membrane penetration, including blood-brain barrier penetration; molecular force field development; and simulations of crystal structures Applications may also involve other fields, such as material science applications, weather simulations, hydrodynamic simulations, equation of state simulations, astrophysics simulations, etc.

12 Alternatives

A variety of arrangements of distributed processing nodes can alternatively be used with the computation decompositions described above.

It is also not necessary that there be a one-to-one correspondence between processing nodes and homeboxes. For example, each node may be responsible for a set of homeboxes, such as a n×n×n cube of homeboxes. One use of such a finer-grain definition of homeboxes is in multiple-zone scheduling approaches in which the schedule of zone-to-zone interactions can be used to avoid a need to test for duplicate computations or can be used to reduce the amount of communication through improved rounding. Another use of such finer-grain homeboxes is in serializing the computation involved with each pair of interacting zones to make better use of local memory, such as local cache memory, at each of the processing nodes. Aspects of memory utilization are discussed further below in the context of serial implementations.

In one alternative version of a parallel implementation, each node maintains data for more particles than those that are located within its homebox. A "clone buffer" approach is used in conjunction with a midpoint assignment rule approach. In particular, each node stores particle data from a region that extends a distance R/2 beyond the boundaries of its homebox. After each computation phase, the forces for all the particles in the extended region are sent to that node allowing it to redundantly compute the new locations of the particles. During the computation phase, further importing of particle data is not necessary, for example, using the midpoint assignment rule or the pseudo-random assignment rule, because the extended region includes all the particles needed.

The approaches described above can be implemented in software, in hardware, or using a combination of hardware and software. For example, alternative versions of the system can be implemented in software, in firmware, in digital electronic circuitry, in computer hardware, in other modes of implementation, or in combinations of such modes. The system can include a computer program product tangibly embodied in a machine-readable storage device, such as on a magnetic or an optical disc or in a semiconductor memory, for execution by a programmable processor or by a system that includes multiple programmable processors. The programmable processors can be general-purpose processors, or can be special-purpose processors, for example, designed for computations of the types described above. Parallel implementation can, for example, use special-purpose interconnection networks, or can use more general purpose data networking approaches. Method steps can be performed by a programmable processor executing a program of instructions to perform functions by operating on input data and generating output. The system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired. Such language can be either a compiled or interpreted language. Suitable processors include, by way of example, either (or both) general and special purpose microprocessors. Generally, a processor will receive instructions and data from read-only memory and/or random access memory. Generally, a computer will include one or more mass storage devices for storing data files. Such devices include magnetic disks such as internal hard disks and removable disks, magneto-optical disks, or optical disks. Storage devices suitable for tangibly embodying computer program instructions and data include all forms of non-volatile memory, including by way of example semiconductor memory devices such as EPROM, EEPROM, and flash memory devices; magnetic disks such as internal hard disks and removable disks; magneto-optical disks; and CD-ROM disks. Any of the foregoing can be incorporated in or supplemented application-specific hardware, such as application-specific integrated circuits (ASICs).

Other embodiments are also within the scope of the appended claims. Reference numerals in the claims, which are provided in parentheses to increase intelligibility, should not be construed as limiting the claim.

What is claimed is:

1. A computation system for computing interactions in a multiple-body simulation, said system comprising an array of processing nodes that are connected to each other, wherein each processing node of said array of processing nodes comprises an array of processing modules arranged into one or more serially interconnected processing groups of the processing modules, wherein each of said groups is serially interconnected in only one dimension, wherein processing modules in each group are not connected to processing modules in other groups, wherein each of the processing modules includes a storage element for data elements and circuitry for performing pairwise computations between data elements each associated with a spatial location, each of the pairwise computations making use of a data element from the storage element of the processing module and a data element passing through the serially interconnected processing modules, and circuitry for selecting the pairs of data elements according to separations between spatial locations associated with the data elements.

2. The system of claim 1, wherein the array of processing modules includes two or more serially interconnected processing groups.

3. The system of claim 1, wherein at least one of the groups of the processing modules includes a serial interconnection of two or more of the processing modules.

4. The system of claim 1, further comprising distribution modules for distributing data elements among the processing groups.

5. The system of claim 1, further comprising combination modules for combining results of the pairwise computations produced by each of the processing groups.

6. A first processing module that is a constituent element of a first processing node from an array of processing nodes, wherein said first processing node comprises an array of processing modules, wherein said first processing module is one of a plurality of identical processing modules within said array, wherein said array comprises a plurality of groups of said processing modules, wherein each group comprises a plurality of processing modules that are serially connected along at most one dimension such that no processing module in a group is connected to a processing module in another group, wherein said first processing module is configured for computing particle interactions in a multiple-body simulation, wherein said first processing module is configured to perform pairwise computations between data elements, each of which is associated with a corresponding spatial location, each of the pairwise computations using one data element from a first set of data elements and one data element from a second set of data elements, wherein said first processing module comprises a plurality of matching units, each matching unit being associated with a storage element for a different part of a first set of data elements, each matching unit being configured to select pairs of data elements according to separations between the locations associated with the data elements, wherein for each pair, one data element is from the first set of data elements and one data element is from a second set of data elements, an input for receiving the second set of data elements, the input being coupled to each of the matching units for passing the received data elements to the matching units, a computation unit coupled to the matching units for receiving pairs of data elements selected by the matching units according to the separations, and an output for transmitting results produced by the computation unit.

7. The first processing module of claim 6, further comprising an output for transmitting the received series of data elements to another processing module.

8. The first processing module claim 6, further comprising an input for receiving results produced by other processing modules, and a merging unit for combining the results produced by the computation unit and the results received on the input for receiving results.

9. The first processing module claim 8, wherein the merging unit includes circuitry for merging results according to a data element of the first set of data elements that is associated with each of the results.

* * * * *